United States Patent
Blake et al.

(10) Patent No.: US 9,763,942 B2
(45) Date of Patent: Sep. 19, 2017

(54) SERINE/THREONINE KINASE INHIBITORS

(71) Applicants: Array BioPharma Inc., Boulder, CO (US); Genentech, Inc., South San Francisco, CA (US)

(72) Inventors: James F. Blake, Boulder, CO (US); Adam Cook, Boulder, CO (US); Indrani W. Gunawardana, Boulder, CO (US); Kevin W. Hunt, Boulder, CO (US); Michael Lyon, Boulder, CO (US); Andrew T. Metcalf, Boulder, CO (US); Peter J. Mohr, Boulder, CO (US); David A. Moreno, Boulder, CO (US); Brad Newhouse, Boulder, CA (US); Li Ren, Boulder, CO (US); Tony P. Tang, Boulder, CO (US); Allen A. Thomas, Boulder, CO (US); Jacob Schwarz, South San Francisco, CA (US); Jane Schmidt, South San Francisco, CA (US); Lewis Gazzard, South San Francisco, CA (US); Huifen Chen, South San Francisco, CA (US)

(73) Assignees: Genentech, Inc., South San Francisco, CA (US); Array BioPharma Inc., Boulder, CO (US)

( * ) Notice: Subject to any disclaimer, the term of this patent is extended or adjusted under 35 U.S.C. 154(b) by 41 days.

(21) Appl. No.: 15/197,479

(22) Filed: Jun. 29, 2016

(65) Prior Publication Data

US 2016/0303126 A1    Oct. 20, 2016

Related U.S. Application Data

(63) Continuation of application No. PCT/US2014/072547, filed on Dec. 29, 2014.

(60) Provisional application No. 61/922,045, filed on Dec. 30, 2013.

(51) Int. Cl.
| | |
|---|---|
| C07D 403/14 | (2006.01) |
| C07D 471/04 | (2006.01) |
| C07D 417/14 | (2006.01) |
| C07D 403/04 | (2006.01) |
| C07D 401/14 | (2006.01) |
| A61K 31/506 | (2006.01) |
| A61K 31/4439 | (2006.01) |
| A61K 31/444 | (2006.01) |
| A61K 45/06 | (2006.01) |
| C07D 405/14 | (2006.01) |

(52) U.S. Cl.
CPC ......... *A61K 31/506* (2013.01); *A61K 31/444* (2013.01); *A61K 31/4439* (2013.01); *A61K 45/06* (2013.01); *C07D 401/14* (2013.01); *C07D 403/04* (2013.01); *C07D 403/14* (2013.01); *C07D 405/14* (2013.01); *C07D 417/14* (2013.01); *C07D 471/04* (2013.01)

(58) Field of Classification Search
CPC .. C07D 403/14; C07D 403/04; C07D 471/04; C07D 471/14; C07D 405/14; C07D 417/14

See application file for complete search history.

(56) References Cited

U.S. PATENT DOCUMENTS

| | | | |
|---|---|---|---|
| 8,697,715 B2 | 4/2014 | Blake et al. | |
| 9,133,187 B2 | 9/2015 | Blake et al. | |
| 9,187,462 B2 | 11/2015 | Blake et al. | |
| 9,259,470 B2 | 2/2016 | Blake et al. | |
| 9,388,171 B2 | 7/2016 | Blake et al. | |
| 2003/0044021 A1* | 3/2003 | Wilkinson | A61B 5/0002 381/56 |
| 2015/0182537 A1 | 7/2015 | Kolesnikov et al. | |

(Continued)

FOREIGN PATENT DOCUMENTS

| | | |
|---|---|---|
| WO | 2012118850 A1 | 9/2012 |
| WO | 2013020062 A1 | 2/2013 |
| WO | 2013130976 A1 | 9/2013 |

OTHER PUBLICATIONS

Hohno, et al., "Pharmacological inhibitors of the ERK signaling pathway: application as anticancer drugs", Prog in Cell Cycle Res 5, 219 (2003).

(Continued)

*Primary Examiner* — Yong Chu
(74) *Attorney, Agent, or Firm* — Viksnins Harris Padys Malen LLP

(57) ABSTRACT

Compounds of Formula I or a stereoisomer, tautomer or pharmaceutically acceptable salt thereof are provided, which are useful for the treatment of hyperproliferative, pain and inflammatory diseases. Methods of using compounds of Formula I or a stereoisomer, tautomer or pharmaceutically acceptable salt thereof, for in vitro, in situ, and in vivo diagnosis, prevention or treatment of such disorders in mammalian cells, or associated pathological conditions are disclosed.

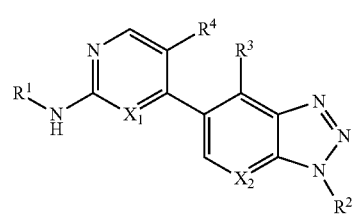

18 Claims, No Drawings

(56) References Cited

U.S. PATENT DOCUMENTS

2016/0122316 A1 5/2016 Blake et al.
2016/0304519 A1 10/2016 Blake et al.

OTHER PUBLICATIONS

Ma, et al., "The ERK/MAPK pathway, as a target for the treatment of neuropathic pain", Expert Opin. Ther. Targets, 9 (4), 699-713 (2005).
Patent Cooperation Treaty, International Searching Authority, Search Report and Written Opinion for PCT/US2014/072547, 9 pages, Mar. 11, 2015.
Sommer, et al., "Resolvins and inflammatory pain", F1000 Medicine Reports, 3, 19, 6 pages (2011).

* cited by examiner

SERINE/THREONINE KINASE INHIBITORS

PRIORITY OF INVENTION

This application is a continuation of International Patent Application No. PCT/US2014/072547, filed Dec. 29, 2014, which claims priority to U.S. Provisional Application No. 61/922,045 that was filed on Dec. 30, 2013 both of which are incorporated herein by reference in their entirety.

BACKGROUND OF THE INVENTION

Field of the Invention

The present invention relates to compounds that inhibit serine/threonine kinases and are useful for treating hyperproliferative and neoplastic diseases by inhibiting signal transduction pathways, which are commonly overactive or overexpressed in cancerous tissue. The present compounds are selective inhibitors of ERK (extracellular-signal regulated kinase). The present invention further relates to methods for treating cancer or hyperproliferative diseases with compounds of the present invention.

Description of the State of the Art

The processes involved in tumor growth, progression, and metastasis are mediated by signaling pathways that are activated in cancer cells. The ERK pathway plays a central role in regulating mammalian cell growth by relaying extracellular signals from ligand-bound cell surface receptor tyrosine kinase ("RTK's"), such as ErbB family, PDGF, FGF, and VEGF receptor tyrosine kinase. Activation of an RTK induces a cascade of phosphorylation events that begins with activation of Ras. Activation of Ras leads to the recruitment and activation of Raf, a serine-threonine kinase. Activated Raf then phosphorylates and activates MEK1/2, which then phosphorylates and activates ERK1/2. When activated, ERK1/2 phosphorylates several downstream targets involved in a multitude of cellular events, including cytoskeletal changes and transcriptional activation. The ERK/MAPK pathway is one of the most important for cell proliferation, and it is believed that the ERK/MAPK pathway is frequently activated in many tumors. Ras genes, which are upstream of ERK1/2, are mutated in several cancers, including colorectal, melanoma, breast and pancreatic tumors. The high Ras activity is accompanied by elevated ERK activity in many human tumors. In addition, mutations of BRAF, a serine-threonine kinase of the Raf family, are associated with increased kinase activity. Mutations in BRAF have been identified in melanomas (60%), thyroid cancers (greater than 40%) and colorectal cancers. These observations indicate that the ERK1/2 signaling pathway is an attractive pathway for anti-cancer therapies in a broad spectrum of human tumors (M. Hohno and J. Pouyssegur, Prog. in Cell Cycle Res. 2003 5:219).

The ERK pathway has also been cited as a promising therapeutic target for the treatment of pain and inflammation (Ma, Weiya and Remi Quirion. "The ERK/MAPK pathway, as a target for the treatment of neuropathic pain." *Expert Opin. Ther. Targets.* 9(4) (2005): pp. 699-713, and Sommer, Claudia and Frank Birklein. "Resolvins and inflammatory pain." *F1000 Medicine Reports.* 3:19 (2011)).

International Patent Application Publications WO 2012/118850, WO 2013/020062 and WO 2013/130976 disclose ERK inhibitors.

Therefore, small-molecular inhibitors of ERK activity (i.e., ERK1 and/or ERK2 activity) would be useful for treating a broad spectrum of cancers, such as, for example, melanoma, pancreatic cancer, thyroid cancer, colorectal cancer, lung cancer, breast cancer, and ovarian cancer, as well as a treatment for pain and inflammation, such as arthritis, low back pain, inflammatory bowel disease, and rheumatism. Such a contribution is provided herein.

SUMMARY OF THE INVENTION

There is a continuing need for new and novel therapeutic agents that can be used for cancer and hyperproliferative conditions. The Raf/MEK/ERK pathway is an important signaling pathway, which is frequently overexpressed and/or overactive in many cancerous tissues. Design and development of new pharmaceutical compounds is essential.

More specifically, one aspect provides compounds of Formula I:

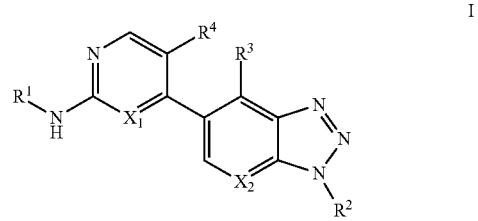

or a stereoisomer, tautomer or pharmaceutically acceptable salt thereof, wherein $X_1$, $X_2$, $R^1$, $R^2$, $R^3$ and $R^4$ are as defined herein.

Another aspect provides compounds of Formulas II, III, IV, V, VI, VII, VIII, IX or X, or a stereoisomer, tautomer or pharmaceutically acceptable salt thereof.

Another aspect provides a method for treating a hyperproliferative disorder by administering a therapeutically effective quantity of a compound according to Formula I, II, III, IV, V, VI, VII, VIII, IX or X, or a stereoisomer, tautomer or pharmaceutically acceptable salt thereof, to a patient in need thereof. The compound can be administered alone or co-administered with at least one other anti-hyperproliferative or chemotherapeutic compound.

Another aspect provides a method of inhibiting ERK protein kinase activity in a cell comprising treating the cell with a compound according to Formula I, II, III, IV, V, VI, VII, VIII, IX or X, or a stereoisomer, tautomer or pharmaceutically acceptable salt thereof, in an amount effective to attenuate or eliminate ERK kinase activity.

Another aspect provides methods of treating or preventing a disease or disorder modulated by ERK, comprising administering to a mammal in need of such treatment an effective amount of a compound of Formula I, II, III, IV, V, VI, VII, VIII, IX or X, or a stereoisomer, tautomer or pharmaceutically acceptable salt thereof. Examples of such diseases and disorders include, but are not limited to, hyperproliferative disorders, such as cancer.

Another aspect provides methods of treating or preventing cancer, comprising administering to a mammal in need of such treatment an effective amount of a compound of Formula I, II, III, IV, V, VI, VII, VIII, IX or X, or a stereoisomer, tautomer or pharmaceutically acceptable salt thereof, alone or in combination with one or more additional compounds having anti-cancer properties.

Another aspect provides a method of treating a hyperproliferative disease in a mammal comprising administering a therapeutically effective amount of a compound of Formula I, II, III, IV, V, VI, VII, VIII, IX or X, or a stereoisomer, tautomer or pharmaceutically acceptable salt thereof, to the mammal.

Another aspect provides the use of a compound of Formula I, II, III, IV, V, VI, VII, VIII, IX or X, or a stereoisomer, tautomer or pharmaceutically acceptable salt thereof, in the manufacture of a medicament for the treatment of a hyperproliferative disease.

Another aspect provides a compound of Formula I, II, III, IV, V, VI, VII, VIII, IX or X, or a stereoisomer, tautomer or pharmaceutically acceptable salt thereof, for use in the treatment of hyperproliferative diseases.

Another aspect provides a pharmaceutical composition comprising a compound of Formula I, II, III, IV, V, VI, VII, VIII, IX or X, or a stereoisomer, tautomer or pharmaceutically acceptable salt thereof, and a pharmaceutically acceptable carrier, diluent or excipient.

Another aspect provides intermediates for preparing compounds of Formula I, II, III, IV, V, VI, VII, VIII, IX or X. Certain compounds of the Formulas may be used as intermediates for other compounds of the Formulas.

Another aspect includes processes for preparing, methods of separation, and methods of purification of the compounds described herein.

DETAILED DESCRIPTION OF THE INVENTION

Reference will now be made in detail to certain embodiments, examples of which are illustrated in the accompanying structures and formulas. While enumerated embodiments will be described, it will be understood that they are not intended to limit the invention to those embodiments. On the contrary, the invention is intended to cover all alternatives, modifications, and equivalents, which may be included within the scope of the present invention as defined by the claims. One skilled in the art will recognize many methods and materials similar or equivalent to those described herein, which could be used in the practice of the present invention. The present invention is in no way limited to the methods and materials described. In the event that one or more of the incorporated literature and similar materials differs from or contradicts this application, including but not limited to defined terms, term usage, described techniques, or the like, this application controls.

Definitions

The phrase "a" or "an" entity as used herein refers to one or more of that entity; for example, a compound refers to one or more compounds or at least one compound. As such, the terms "a" (or "an"), "one or more", and "at least one" can be used interchangeably herein.

The phrase "as defined herein" refers to the broadest definition for each group as provided in the Detailed Description of the Invention or the broadest claim. In all other embodiments provided below, substituents that can be present in each embodiment, and which are not explicitly defined, retain the broadest definition provided in the Detailed Description of the Invention.

As used in this specification, whether in a transitional phrase or in the body of the claim, the terms "comprise(s)" and "comprising" are to be interpreted as having an open-ended meaning. That is, the terms are to be interpreted synonymously with the phrases "having at least" or "including at least". When used in the context of a process, the term "comprising" means that the process includes at least the recited steps, but may include additional steps. When used in the context of a compound or composition, the term "comprising" means that the compound or composition includes at least the recited features or components, but may also include additional features or components. Additionally, the words "include," "including," and "includes" when used in this specification and in the following claims are intended to specify the presence of stated features, integers, components, or steps, but they do not preclude the presence or addition of one or more other features, integers, components, steps, or groups thereof.

The term "independently" is used herein to indicate that a variable is applied in any one instance without regard to the presence or absence of a variable having that same or a different definition within the same compound. Thus, in a compound in which R" appears twice and is defined as "independently carbon or nitrogen", both R"s can be carbon, both R"s can be nitrogen, or one R" can be carbon and the other nitrogen.

When any variable (e.g., $R^1$, $R^{4a}$, Ar, $X_1$ or Het) occurs more than one time in any moiety or formula depicting and describing compounds employed or claimed in the present invention, its definition on each occurrence is independent of its definition at every other occurrence. Also, combinations of substituents and/or variables are permissible only if such compounds result in stable compounds.

The term "optional" or "optionally" as used herein means that a subsequently described event or circumstance may, but need not, occur, and that the description includes instances where the event or circumstance occurs and instances in which it does not. For example, "optionally substituted" means that the optionally substituted moiety may incorporate a hydrogen or a substituent.

The term "about" is used herein to mean approximately, in the region of, roughly, or around. When the term "about" is used in conjunction with a numerical range, it modifies that range by extending the boundaries above and below the numerical values set forth. In general, the term "about" is used herein to modify a numerical value above and below the stated value by a variance of 20%.

As used herein, the recitation of a numerical range for a variable is intended to convey that the invention may be practiced with the variable equal to any of the values within that range. Thus, for a variable that is inherently discrete, the variable can be equal to any integer value of the numerical range, including the end-points of the range. Similarly, for a variable that is inherently continuous, the variable can be equal to any real value of the numerical range, including the end-points of the range. As an example, a variable that is described as having values between 0 and 2, can be 0, 1 or 2 for variables that are inherently discrete, and can be 0.0, 0.1, 0.01, 0.001, or any other real value for variables that are inherently continuous.

Certain compounds of Formula I, II, III, IV, V, VI, VII, VIII, IX or X may exhibit tautomerism. Tautomeric compounds can exist as two or more interconvertible species. Prototropic tautomers result from the migration of a covalently bonded hydrogen atom between two atoms. Tautomers generally exist in equilibrium and attempts to isolate an individual tautomers usually produce a mixture whose chemical and physical properties are consistent with a mixture of compounds. The position of the equilibrium is dependent on chemical features within the molecule. For example, in many aliphatic aldehydes and ketones, such as acetaldehyde, the keto form predominates; while in phenols, the enol form predominates. Common prototropic tautomers include keto/enol (—C(=O)—CH2-↔ -C(—OH)=CH—), amide/imidic acid (—C(=O)—NH-↔-C(—OH)=N—) and amidine (—C(=NR)—NH-↔-C(—NHR)=N—) tautomers. The latter two are particularly common in heteroaryl and heterocyclic rings, and the present invention encompasses all tautomeric forms of the compounds.

It will be appreciated by the skilled artisan that some of the compounds of Formula I, II, III, IV, V, VI, VII, VIII, IX or X may contain one or more chiral centers and therefore exist in two or more stereoisomeric forms. The racemates of these isomers, the individual isomers and mixtures enriched in one enantiomer, as well as diastereomers when there are two chiral centers, and mixtures partially enriched with specific diastereomers are within the scope of the present invention. The present invention includes all the individual stereoisomers (e.g., enantiomers), racemic mixtures or partially resolved mixtures of the compounds of Formula I, II, III, IV, V, VI, VII, VIII, IX or X and, where appropriate, the individual tautomeric forms thereof.

The compounds of Formula I, II, III, IV, V, VI, VII, VIII, IX or X may contain a basic center and suitable acid addition salts are formed from acids that form non-toxic salts. Examples of salts of inorganic acids include the hydrochloride, hydrobromide, hydroiodide, chloride, bromide, iodide, sulfate, bisulfate, nitrate, phosphate, and hydrogen phosphate. Examples of salts of organic acids include acetate, fumarate, pamoate, aspartate, besylate, carbonate, bicarbonate, camsylate, D and L-lactate, D and L-tartrate, esylate, mesylate, malonate, orotate, gluceptate, methylsulfate, stearate, glucuronate, 2-napsylate, tosylate, hibenzate, nicotinate, isethionate, malate, maleate, citrate, gluconate, succinate, saccharate, benzoate, esylate, and pamoate salts. For a review on suitable salts, see Berge, Stephen M., et al. "Pharmaceutical salts." *J. Pharm. Sci.* Vol. 66, No. 1 (1977): 1-19, and Paulekuhn, G. Steffen, et al. "Trends in Active Pharmaceutical Ingredient Salt Selection based on Analysis of the Orange Book Database." *J. Med. Chem.* Vol. 50, No. 26 (2007): 6665-6672.

Technical and scientific terms used herein have the meaning commonly understood by one of skill in the art to which the present invention pertains, unless otherwise defined. Reference is made herein to various methodologies and materials known to those of skill in the art. A standard reference work setting forth the general principles of pharmacology include Hardman, Joel Griffith, et al. *Goodman & Gilman's The Pharmacological Basis of Therapeutics*. New York: McGraw-Hill Professional, 2001. The starting materials and reagents used in preparing these compounds generally are either available from commercial suppliers, such as Sigma-Aldrich (St. Louis, Mo.), or are prepared by methods known to those skilled in the art following procedures set forth in references. Materials, reagents and the like to which reference are made in the following description and examples are obtainable from commercial sources, unless otherwise noted. General synthetic procedures have been described in treatises, such as Louis F. Fieser and Mary Fieser, *Reagents for Organic Synthesis*. v. 1-23, New York: Wiley 1967-2006 ed. (also available via the Wiley InterScience® website); LaRock, Richard C., *Comprehensive Organic Transformations: A Guide to Functional Group Preparations*. New York: Wiley-VCH, 1999; B. Trost and I. Fleming, eds. *Comprehensive Organic Synthesis*. v. 1-9, Oxford: Pergamon 1991; A. R. Katritzky and C. W. Rees, eds. *Comprehensive Heterocyclic Chemistry*. Oxford: Pergamon 1984; A. R. Katritzky and C. W. Rees, eds. *Comprehensive Heterocyclic Chemistry II*. Oxford: Pergamon 1996; and Paquette, Leo A., ed. *Organic Reactions*. v. 1-40, New York: Wiley & Sons 1991; and will be familiar to those skilled in the art.

The definitions described herein may be appended to form chemically-relevant combinations, such as "heteroalkylaryl," "haloalkylheteroaryl," "arylalkylheterocyclyl," "alkylcarbonyl," "alkoxyalkyl," and the like. When the term "alkyl" is used as a suffix following another term, as in "phenylalkyl," or "hydroxyalkyl," this is intended to refer to an alkyl group, as defined above, being substituted with at least one substituent selected from the other specifically-named group. Thus, for example, "phenylalkyl" refers to an alkyl group having at least one phenyl substituent, and thus includes benzyl and phenylethyl. An "alkylaminoalkyl" is an alkyl group having at least one alkylamino substituent. "Hydroxyalkyl" includes 2-hydroxyethyl, 2-hydroxypropyl, 1-(hydroxymethyl)-2-methylpropyl, 2-hydroxybutyl, 2,3-dihydroxybutyl, 2-(hydroxymethyl), 3-hydroxypropyl, and so forth. Accordingly, as used herein, the term "hydroxyalkyl" is used to define a subset of heteroalkyl groups defined below. The term -(ar)alkyl refers to either an unsubstituted alkyl or an aralkyl group. The term (hetero)aryl or (het)aryl refers to a moiety that is either an aryl or a heteroaryl group.

The term "$C_1$-$C_4$ acyloxy-$C_1$-$C_2$ alkyl" as used herein denotes a group of formula —$(CH_2)_{1-2}OC(O)(CH_2)_{0-3}H$. The term "$C_1$-$C_4$ acyloxy" as used herein denotes the radical —OC(O)R, wherein R contains 1 to 4 carbon atoms (e.g., $C_1$ is formyl).

The term "alkyl" includes linear or branched-chain radicals of carbon atoms. Some alkyl moieties have been abbreviated, for example, methyl ("Me"), ethyl ("Et"), propyl ("Pr") and butyl ("Bu"), and further abbreviations are used to designate specific isomers of compounds, for example, 1-propyl or n-propyl ("n-Pr"), 2-propyl or isopropyl ("i-Pr"), 1-butyl or n-butyl ("n-Bu"), 2-methyl-1-propyl or isobutyl ("i-Bu"), 1-methylpropyl or s-butyl ("s-Bu"), 1,1-dimethylethyl or t-butyl ("t-Bu") and the like. The abbreviations are sometimes used in conjunction with elemental abbreviations and chemical structures, for example, methanol ("MeOH") or ethanol ("EtOH").

Additional abbreviations used throughout the application may include, for example, benzyl ("Bn"), phenyl ("Ph") and acetate ("Ac").

The terms "alkenyl" and "alkynyl" also include linear or branched-chain radicals of carbon atoms.

The term "haloalkyl" as used herein denotes an unbranched or branched chain alkyl group as defined above, wherein 1, 2, 3 or more hydrogen atoms are substituted by a halogen. Examples are 1-fluoromethyl, 1-chloromethyl, 1-bromomethyl, 1-iodomethyl, difluoromethyl, trifluoromethyl, trichloromethyl, 1-fluoroethyl, 1-chloroethyl, 2-fluoroethyl, 2-chloroethyl, 2-bromoethyl, 2,2-dichloroethyl, 3-bromopropyl, 2,2,2-trifluoroethyl, 2-chloro-3-fluoropropyl and 1,1,2,2,2-pentafluoroethyl (perfluoroethyl).

The term "heteroalkyl" as used herein means an alkyl radical as defined herein, wherein one or two hydrogen atoms have been replaced with a substituent independently selected from the group consisting of —$OR^\alpha$ and —$NR^\beta R^\gamma$, with the understanding that the point of attachment of the heteroalkyl radical is through a carbon atom. $R^\alpha$ is hydrogen or alkyl and $R^\beta$ and $R^\gamma$ are independently of each other hydrogen, acyl, alkyl, or $R^\beta$ and $R^\gamma$ together with the nitrogen to which they are attached form a cyclic amine. Hydroxyalkyl, alkoxyalkyl, aminoalkyl, alkylaminoalkyl and dialkylaminoalkyl moieties are subgenera encompassed by the term "heteroalkyl". Representative examples include, but are not limited to, 2-hydroxyethyl, 3-hydroxypropyl, 2-hydroxy-1-hydroxymethylethyl, 2,3-dihydroxypropyl, 1-hydroxymethylethyl, 3-hydroxybutyl, 2,3-dihydroxybutyl, 2-hydroxy-1-methylpropyl, 2-aminoethyl, 3-methylaminopropyl, and the like.

The term "heteroaryl" includes five to six membered monocyclic and nine to ten membered bicyclic aromatic rings containing one, two, three or four heteroatoms selected from the group consisting of oxygen, nitrogen and sulfur, with the proviso that the ring does not contain two adjacent O or S atoms. In certain instances, these terms may be specifically further limited, such as, five to six membered heteroaryl, wherein the heteroaryl contains one or two nitrogen heteroatoms. As well known to those skilled in the art, heteroaryl rings have less aromatic character than their all-carbon counter parts. Thus, for the purposes of the invention, a heteroaryl group need only have some degree of aromatic character.

Heteroaryl groups may include, for example, pyrrolyl, thiophenyl (thienyl), furanyl (furyl), imidazolyl, pyrazolyl, thiazolyl, isothiazolyl, oxazolyl, isoxazolyl, triazolyl, thiadiazolyl, oxadiazolyl, tetrazolyl, thiatriazolyl, oxatriazolyl, pyridinyl (pyridyl), pyrimidyl, pyrazinyl, pyridazinyl, thiazinyl, oxazinyl, triazinyl, thiadiazinyl, oxadiazinyl, dithiazinyl, dioxazinyl, oxathiazinyl, tetrazinyl, thiatriazinyl, oxatriazinyl, dithiadiazinyl, imidazolinyl, benzofuranyl, benzothiophenyl, indolyl, benzimidazolyl, indazolyl, benzotriazolyl, pyrrolopyridinyl, imidazopyridinyl, pyrazolopyridine, isoindolyl, indazolyl, purinyl, indolininyl, pyrrolopyridazinyl, imidazopyrimidinyl, quinolinyl, isoquinolinyl, cinnolinyl, quinazolinyl, quinoxalinyl, phthalazinyl, napthyridinyl, pyridopyrimidinyl, pyridopyrazinyl, pyrimidopyrimidinyl and pyraziniopyrazinyl.

The terms "heterocycle", "heterocyclic" and "heterocyclyl" include three to seven membered monocyclic saturated or partially unsaturated rings containing one, two or three heteroatoms selected from the group consisting of oxygen, nitrogen, sulfur, S(=O) and S(=O)$_2$, with the proviso that the ring does not contain two adjacent O or S atoms. In certain instances, these terms may be specifically further limited, such as, "five to six membered heterocyclyl" only including five and six membered rings. Bicyclic heterocyclic groups include five to fourteen membered bicyclic saturated or partially unsaturated rings containing one, two or three heteroatoms selected from the group consisting of oxygen, nitrogen, sulfur, S(=O) and S(=O)$_2$. In certain instances, these terms may be specifically further limited, such as, "seven to ten membered heterocyclyl" only including seven to ten membered bicyclic rings.

Heterocyclic groups may include, for example, oxiranyl, thiaranyl, aziridinyl, oxetanyl, thiatanyl, azetidinyl, tetrahydrofuranyl, tetrahydrothiophenyl, pyrrolidinyl, tetrahydropyranyl, tetrahyrdothiopyranyl, piperidinyl, dioxanyl, oxathianyl, morpholinyl (morpholino), dithianyl, piperazinyl, azathianyl, oxepanyl, thiepanyl, azepanyl, dioxepanyl, oxathiepanyl, oxaazepanyl, dithiepanyl, thieazepanyl, diazepanyl, dihydrofuranyl, dihydropyranyl, pyranyl and tetrahydropyridinyl. Further examples of the 5- and 6-membered ring systems discussed above can be found in U.S. Pat. No. 4,278,793.

The terms "hydroxyalkyl" and "alkoxyalkyl" as used herein denotes alkyl radical as herein defined, wherein one to three hydrogen atoms on different carbon atoms is/are replaced by hydroxyl or alkoxy groups respectively. A $C_1$-$C_3$ alkoxy-$C_1$-$C_6$ alkyl moiety refers to a $C_1$-$C_6$ alkyl substituent in which one to three hydrogen atoms are replaced by a $C_1$-$C_3$ alkoxy and the point of attachment of the alkoxy is the oxygen atom.

A bond drawn into ring system (as opposed to connected at a distinct vertex) indicates that the bond may be attached to any of the suitable ring atoms.

Methods of this invention encompass methods of treating, preventing and/or managing various types of cancer and diseases and disorders associated with, or characterized by, undesired angiogenesis. As used herein, unless otherwise specified, the term "treating" or "treat" refers to the administration of a compound of the invention or other additional active agent after the onset of symptoms of the particular disease or disorder. The terms "treat" or "treatment" also refer to therapeutic or palliative measures. Beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. "Treatment" can also mean prolonging survival as compared to expected survival if not receiving treatment. Those in need of treatment include those already with the condition or disorder, as well as those prone to have the condition or disorder. As used herein, unless otherwise specified, the term "preventing" refers to the administration prior to the onset of symptoms, particularly to patients at risk of cancer, and other diseases and disorders associated with, or characterized by, undesired angiogenesis. The term "prevention" includes the inhibition of a symptom of the particular disease or disorder. Patients with familial history of cancer and diseases and disorders associated with, or characterized by, undesired angiogenesis are preferred candidates for preventive regimens. As used herein and unless otherwise indicated, the term "managing" encompasses preventing the recurrence of the particular disease or disorder in a patient who had suffered from it, and/or lengthening the time a patient who had suffered from the disease or disorder remains in remission.

The phrases "therapeutically effective amount" or "effective amount" mean an amount of a compound described herein that, when administered to a mammal in need of such treatment, sufficient to (i) treat or prevent the particular disease, condition, or disorder, (ii) attenuate, ameliorate, or eliminate one or more symptoms of the particular disease, condition, or disorder, or (iii) prevent or delay the onset of one or more symptoms of the particular disease, condition, or disorder described herein. The amount of a compound that will correspond to such an amount will vary depending upon factors such as the particular compound, disease condition and its severity, the identity (e.g., weight) of the mammal in need of treatment, but can nevertheless be routinely determined by one skilled in the art.

The terms "cancer" and "cancerous" refer to or describe the physiological condition in mammals that is typically characterized by abnormal or unregulated cell growth. A "tumor" comprises one or more cancerous cells. Examples of cancer include, but are not limited to, carcinoma, lymphoma, blastoma, sarcoma, and leukemia or lymphoid malignancies. More particular examples of such cancers include squamous cell cancer (e.g., epithelial squamous cell cancer), lung cancer including small-cell lung cancer, non-small cell lung cancer ("NSCLC"), adenocarcinoma of the lung and squamous carcinoma of the lung, cancer of the peritoneum, hepatocellular cancer, gastric or stomach cancer including gastrointestinal cancer, pancreatic cancer, glioblastoma, cervical cancer, ovarian cancer, liver cancer, bladder cancer, hepatoma, breast cancer, colon cancer, rectal cancer, colorectal cancer, endometrial or uterine carcinoma, salivary gland carcinoma, kidney or renal cancer, prostate cancer, vulval cancer, thyroid cancer, hepatic carcinoma, anal carcinoma, penile carcinoma, skin cancer, including melanoma, as well as head and neck cancer.

A "chemotherapeutic agent" is a chemical compound useful in the treatment of cancer. Examples of chemotherapeutic agents include erlotinib (TARCEVA®, Genentech/OSI Pharm.), bortezomib (VELCADE®, Millennium Pharm.), fulvestrant (FASLODEX®, AstraZeneca), sunitib (SUTENT®, Pfizer/Sugen), letrozole (FEMARA®, Novartis), imatinib mesylate (GLEEVEC®, Novartis), finasunate (VATALANIB®, Novartis), oxaliplatin (ELOXATIN®, Sanofi), 5-FU (5-fluorouracil), leucovorin, Rapamycin (Sirolimus, RAPAMUNE®, Wyeth), Lapatinib (TYKERB®, GSK572016, Glaxo Smith Kline), Lonafamib (SCH 66336), sorafenib (NEXAVAR®, Bayer Labs), gefitinib (IRESSA®, AstraZeneca), AG1478, alkylating agents such as thiotepa and CYTOXAN® cyclosphosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, triethylenephosphoramide, triethylenethiophosphoramide and trimethylomelamine; acetogenins (especially bullatacin and bullatacinone); a camptothecin (including the synthetic analog topotecan); bryostatin; callystatin; CC-1065 (including its adozelesin, carzelesin and bizelesin synthetic analogs); cryptophycins (particularly cryptophycin 1 and cryptophycin 8); dolastatin; duocarmycin (including the synthetic analogs, KW-2189 and CB1-TM1); eleutherobin; pancratistatin; a sarcodictyin; spongistatin; nitrogen mustards such as chlorambucil, chlomaphazine, chlorophosphamide, estramustine, ifosfamide, mechlorethamine, mechlorethamine oxide hydrochloride, melphalan, novembichin, phenesterine, prednimustine, trofosfamide, uracil mustard; nitrosoureas such as carmustine, chlorozotocin, fotemustine, lomustine, nimustine, and ranimnustine; antibiotics such as the enediyne antibiotics (e.g., calicheamicin, especially calicheamicin γ1I and calicheamicin ω1I (Angew Chem. Intl. Ed. Engl. 1994 33:183-186); dynemicin, including dynemicin A; bisphosphonates, such as clodronate; an esperamicin; as well as neocarzinostatin chromophore and related chromoprotein enediyne antibiotic chromophores), aclacinomysins, actinomycin, authramycin, azaserine, bleomycins, cactinomycin, carabicin, caminomycin, carzinophilin, chromomycinis, dactinomycin, daunorubicin, detorubicin, 6-diazo-5-oxo-L-norleucine, ADRIAMYCIN® (doxorubicin), morpholinodoxorubicin, cyanomorpholino-doxorubicin, 2-pyrrolinodoxorubicin and deoxydoxorubicin), epirubicin, esorubicin, idarubicin, marcellomycin, mitomycins such as mitomycin C, mycophenolic acid, nogalamycin, olivomycins, peplomycin, porfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogs such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elfomithine; elliptinium acetate; an epothilone; etoglucid; gallium nitrate; hydroxyurea; lentinan; lonidainine; maytansinoids such as maytansine and ansamitocins; mitoguazone; mitoxantrone; mopidamnol; nitraerine; pentostatin; phenamet; pirarubicin; losoxantrone; podophyllinic acid; 2-ethylhydrazide; procarbazine; PSK® polysaccharide complex (JHS Natural Products, Eugene, Oreg.); razoxane; rhizoxin; sizofuran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; taxoids, e.g., TAXOL (paclitaxel; Bristol-Myers Squibb Oncology, Princeton, N.J.), ABRAXANE® (Cremophor-free), albumin-engineered nanoparticle formulations of paclitaxel (American Pharmaceutical Partners, Schaumberg, Ill.), and TAXOTERE® (docetaxel, doxetaxel; Sanofi-Aventis); chloranmbucil; GEMZAR® (gemcitabine); 6-thioguanine; mercaptopurine; methotrexate; platinum analogs such as cisplatin and carboplatin; vinblastine; etoposide (VP-16); ifosfamide; mitoxantrone; vincristine; NAVELBINE® (vinorelbine); novantrone; teniposide; edatrexate; daunomycin; aminopterin; capecitabine (XELODA®); ibandronate; CPT-11; topoisomerase inhibitor RFS 2000; difluoromethylomithine (DMFO); retinoids such as retinoic acid; and pharmaceutically acceptable salts, acids and derivatives of any of the above.

Also included in the definition of "chemotherapeutic agent" are: (i) anti-hormonal agents that act to regulate or inhibit hormone action on tumors such as anti-estrogens and selective estrogen receptor modulators (SERMs), including, for example, tamoxifen (including NOLVADEX®; tamoxifen citrate), raloxifene, droloxifene, 4-hydroxytamoxifen, trioxifene, keoxifene, LY117018, onapristone, and FARESTON® (toremifine citrate); (ii) aromatase inhibitors that inhibit the enzyme aromatase, which regulates estrogen production in the adrenal glands, such as, for example, 4(5)-imidazoles, aminoglutethimide, MEGASE® (megestrol acetate), AROMASIN® (exemestane; Pfizer), formestanie, fadrozole, RIVISOR® (vorozole), FEMARA® (letrozole; Novartis), and ARIMIDEX® (anastrozole; AstraZeneca); (iii) anti-androgens such as flutamide, nilutamide, bicalutamide, leuprolide, and goserelin; as well as troxacitabine (a 1,3-dioxolane nucleoside cytosine analog); (iv) protein kinase inhibitors; (v) lipid kinase inhibitors; (vi) antisense oligonucleotides, particularly those which inhibit expression of genes in signaling pathways implicated in aberrant cell proliferation, such as, for example, PKC-alpha, Raf and H-Ras; (vii) ribozymes such as VEGF expression inhibitors (e.g., ANGIOZYME®) and HER2 expression inhibitors; (viii) vaccines such as gene therapy vaccines, for example, ALLOVECTIN®, LEUVECTIN®, and VAXID®; PROLEUKIN®, rIL-2; a topoisomerase 1 inhibitor such as LURTOTECAN®; ABARELIX® rmRH; (ix) anti-angiogenic agents such as bevacizumab (AVASTIN®, Genentech); and (x) pharmaceutically acceptable salts, acids and derivatives of any of the above.

The phrase "pharmaceutically acceptable" indicates that the substance or composition is compatible chemically and/or toxicologically, with the other ingredients comprising a formulation, and/or the mammal being treated therewith.

The phrase "pharmaceutically acceptable salt," as used herein, refers to pharmaceutically acceptable organic or inorganic salts of a compound described herein.

The compounds described herein also include other salts of such compounds that are not necessarily pharmaceutically acceptable salts, and which may be useful as intermediates for preparing and/or purifying compounds described herein and/or for separating enantiomers of compounds described herein.

The term "mammal" means a warm-blooded animal that has or is at risk of developing a disease described herein and includes, but is not limited to, guinea pigs, dogs, cats, rats, mice, hamsters, and primates, including humans.

ERK Compounds

Provided herein are compounds, and pharmaceutical formulations thereof, that are potentially useful in the treatment of diseases, conditions and/or disorders modulated by ERK.

One embodiment provides compounds of Formula I:

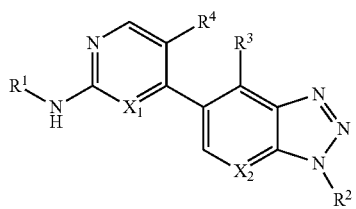

I or a stereoisomer, tautomer or pharmaceutically acceptable salt thereof, wherein:

$X_1$ is selected from CH and N;
$X_2$ is selected from CH and N;
$R^1$ is selected from $C_1$-$C_{12}$ alkyl, $C_2$-$C_{12}$ alkenyl, $C_2$-$C_{12}$ alkynyl, $C_3$-$C_7$ cycloalkyl, phenyl, a 3 to 7 membered saturated or partially unsaturated heterocyclyl, a 5 to 6 membered heteroaryl, $C_5$-$C_{14}$ bicyclic cycloalkyl, naphthyl, a 5 to 14 membered bicyclic saturated or partially unsaturated heterocycle and a 9 to 10 membered bicyclic heteroaryl, wherein the alkyl, alkenyl, alkynyl, cycloalkyls, phenyl, heterocyclyls, heteroaryls and naphthyl may be optionally substituted with one or more groups independently selected from halogen, $OR^a$e, $NR^bR^c$, oxo, oxide, CN, $C_3$-$C_6$ cycloalkyl, cyclopropylmethyl, a 3 to 7 membered heterocycle, $C_1$-$C_6$ haloalkyl, $C_1$-$C_3$ hydroxyalkyl, $C_1$-$C_4$ acyloxy-$C_1$-$C_2$ alkyl, phenyl and $C_1$-$C_6$ alkyl optionally substituted with one or more groups independently selected from oxo and $OR^d$;

$R^2$ is selected from hydrogen, $C_1$-$C_{12}$ alkyl, $C_2$-$C_{12}$ alkenyl, $C_2$-$C_{12}$ alkynyl, $C_3$-$C_7$ cycloalkyl, a 3 to 7 membered saturated or partially unsaturated heterocyclyl, phenyl, a 5 to 6 membered heteroaryl, $C_5$-$C_{14}$ bicyclic cycloalkyl, naphthyl, a 5 to 14 membered bicyclic saturated or partially unsaturated heterocyclyl, and a 9 to 10 membered bicyclic heteroaryl, wherein the alkyl, alkenyl, alkynyl, cycloalkyls, phenyl, heterocyclyls, heteroaryls and naphthyl may be optionally substituted with one or more groups independently selected from halogen; hydroxy; $C_1$-$C_6$ alkyl optionally substituted with one or more groups independently selected from halogen, $C_1$-$C_3$ alkoxy, or phenyl optionally substituted with two groups selected from halogen and $C_1$-$C_3$ alkoxy; $C_1$-$C_6$ alkoxy optionally substituted with one or more groups selected from halogen; $NR^kR^m$; $C_3$-$C_6$ cylcoalkyl optionally substituted with one or more groups independently selected from halogen, $C_1$-$C_3$ alkyl, $C_1$-$C_3$ alkoxy and phenyl optionally substituted with $C_1$-$C_3$ alkoxy, wherein the alkyl, alkoxys and phenyl may be optionally substituted with halogen; a 4 to 6 membered heterocyclyl optionally substituted with one or more groups independently selected from halogen, $C_1$-$C_3$ alkoxy, $C_1$-$C_3$ alkyl optionally substituted with halogen, —C(=O)O($C_1$-$C_6$ alkyl) and phenyl; phenyl optionally substituted with one or more groups independently selected from halogen, $C_1$-$C_3$ alkyl and $C_1$-$C_3$ alkoxy, wherein the alkyl and alkoxy may be optionally substituted with halogen; a 5 to 6 membered heteroaryl optionally substituted with one or more groups independently selected from halogen, $C_1$-$C_3$ alkyl, $C_1$-$C_3$ alkoxy and a 5 to 6 membered heteroaryl, wherein the alkyl and alkoxy may be optionally substituted with halogen;

$R^3$ is selected from hydrogen and halogen;
$R^4$ is selected from hydrogen and halogen;
each $R^a$, $R^b$, $R^c$ and $R^d$ are independently selected from hydrogen, $C_1$-$C_6$ alkyl and $C_1$-$C_6$ haloalkyl; and
each $R^k$ and $R^m$ are independently selected from hydrogen, $C_1$-$C_3$ alkyl and $C_1$-$C_6$ haloalkyl.

One embodiment provides compounds of Formula I and stereoisomers and pharmaceutically acceptable salts thereof, wherein:

$X_1$ is selected from CH and N;
$X_2$ is selected from CH and N;
$R^1$ is selected from (a) $C_1$-$C_6$ alkyl optionally substituted with one or more groups independently selected from halogen, $OR^a$, $NR^bR^c$, oxo, CN, $C_3$-$C_6$ cycloalkyl and a 3 to 7 membered heterocycle; (b) $C_3$-$C_7$ cycloalkyl optionally substituted with one or more groups independently selected from halogen, $OR^a$, CN and $C_1$-$C_3$ alkyl optionally substituted with one or more groups independently selected from halogen and $OR^d$; (c) phenyl optionally substituted with one or more groups independently selected from halogen, $OR^a$, CN, $C_3$-$C_6$ cycloalkyl and $C_1$-$C_3$ alkyl optionally substituted with one or more groups independently selected from halogen and $OR^d$; (d) a 3 to 7 membered saturated or partially unsaturated heterocyclyl optionally substituted with one or more groups independently selected from halogen, $OR^a$, oxo, CN, $C_3$-$C_6$ cycloalkyl and $C_1$-$C_3$ alkyl optionally substituted with one or more groups independently selected from halogen and $OR^d$; (e) a 5 to 6 membered heteroaryl optionally substituted with one or more groups independently selected from halogen, $OR^e$, oxide, CN, $C_3$-$C_6$ cycloalkyl and $C_1$-$C_3$ alkyl optionally substituted with one or more groups independently selected from halogen, oxo and $OR^d$; and (f) a 7 to 10 membered bicyclic heterocycle optionally substituted with one or more groups independently selected from halogen, $OR^a$, oxo, CN, $C_3$-$C_6$ cycloalkyl and $C_1$-$C_3$ alkyl optionally substituted with one or more groups independently selected from halogen and $OR^d$;

$R^2$ is selected from (a) $C_1$-$C_{10}$ alkyl optionally substituted with one to four $R^f$ groups; (b) $C_3$-$C_6$ cycloalkyl optionally substituted with halogen, $C_1$-$C_3$ alkyl and $C_1$-$C_3$ alkoxy; (c) a 4 to 6 membered heterocyclyl containing one to three heteroatoms selected from N, O and S, wherein the heterocyclyl may be optionally substituted with one to four $R^g$ groups; (d) phenyl optionally substituted with one to four groups selected from halogen, $C_1$-$C_3$ alkyl and $C_1$-$C_3$ alkoxy; (e) a 5 to 6 membered heteroaryl containing one to four heteroatoms selected from N, O and S, wherein the heteroaryl may be optionally substituted with one to four groups selected from halogen, $C_1$-$C_3$ alkyl, $C_1$-$C_3$ alkoxy and a 5 to 6 membered heteroaryl containing one to four heteroatoms selected from N, O and S; (f) $C_8$-$C_{10}$ bicyclic cycloalkyl optionally substituted with halogen, $C_1$-$C_3$ alkyl and $C_1$-$C_3$ alkoxy; and (g) a 9 to 10 membered bicyclic heterocyclyl containing one to three heteroatoms selected from N, O and S, wherein the heterocyclyl may be optionally substituted with halogen, $C_1$-$C_3$ alkyl and $C_1$-$C_3$ alkoxy;

$R^3$ is selected from hydrogen and halogen;
$R^4$ is selected from hydrogen and halogen;

each $R^a$, $R^b$, $R^c$, $R^d$ and $R^e$ are independently selected from hydrogen and $C_1$-$C_6$ alkyl;

each $R^f$ is selected from (a) halogen; (b) hydroxy; (c) $C_1$-$C_3$ alkoxy; (d) $NR^kR^m$; (e) $C_3$-$C_6$ cylcoalkyl optionally substituted with one or more $R^h$ groups; (f) a 4 to 6 membered heterocyclyl containing one to three heteroatoms selected from N, O and S, wherein the heterocyclyl may be optionally substituted with one or more groups selected from halogen, $C_1$-$C_3$ alkoxy, $C_1$-$C_3$ alkyl optionally substituted with halogen, —C(=O)O($C_1$-$C_6$ alkyl) and phenyl; (g) phenyl optionally substituted with one or more $R^j$ groups; and (h) a 5 to 6 membered heteroaryl containing one to four heteroatoms selected from N, O and S, wherein the heteroaryl may be optionally substituted with one or more $R^j$ groups;

each $R^g$ is selected from (a) halogen; (b) $C_1$-$C_3$ alkyl optionally substituted with halogen, $C_1$-$C_3$ alkoxy, or phenyl optionally substituted with two groups selected from halogen and $C_1$-$C_3$ alkoxy; (c) $C_1$-$C_3$ alkoxy optionally substituted with halogen; (d) phenyl optionally substituted with halogen or $C_1$-$C_3$ alkoxy; and (e) a 5 to 6 membered heteroaryl containing one to four heteroatoms selected from N, O and S, wherein the heteroaryl may be optionally substituted with one or two groups selected from halogen and $C_1$-$C_3$ alkoxy;

each $R^h$ is selected from halogen, $C_1$-$C_3$ alkyl, $C_1$-$C_3$ alkoxy and phenyl optionally substituted with $C_1$-$C_3$ alkoxy, wherein the alkyl, alkoxys and phenyl may be optionally substituted with halogen;

each $R^j$ is selected from halogen, $C_1$-$C_3$ alkyl and $C_1$-$C_3$ alkoxy, wherein the alkyl and alkoxy may be optionally substituted with halogen; and each $R^k$ and $R^m$ are independently selected from hydrogen and $C_1$-$C_3$ alkyl.

In certain embodiments of Formula I:
$X_1$ is selected from CH and N;
$X_2$ is selected from CH and N;
$R^1$ is selected from (a) $C_1$-$C_5$ alkyl optionally substituted with one or two groups selected from OH, cyclopropyl, oxetanyl and morpholino; (b) $C_3$-$C_4$ cycloalkyl; (c) a 4 to 6 membered heterocyclyl containing one O heteroatom optionally substituted with halogen or methyl; and (d) a 5 membered heteroaryl containing two to four heteroatoms selected from N and S substituted with one to three groups selected from methyl and cyclopropyl;
$R^2$ is selected from (a) $C_1$-$C_6$ alkyl optionally substituted with one or two $R^f$ groups; (b) $C_3$-$C_6$ cycloalkyl optionally substituted with one or two halogens; (c) a 4 to 6 membered heterocyclyl containing one to three heteroatoms selected from N, O and S, wherein the heterocyclyl may be optionally substituted with one to three $R^g$ groups; (d) a 5 to 6 membered heteroaryl containing one to four heteroatoms selected from N, O and S, wherein the heteroaryl may be optionally substituted with one or two groups selected from $C_1$-$C_3$ alkyl and a 5 to 6 membered heteroaryl containing one to four heteroatoms selected from N, O and S; and (e) $C_8$-$C_{10}$ bicyclic cycloalkyl optionally substituted with halogen;
$R^3$ and $R^4$ are hydrogen;
each $R^f$ is independently selected from (a) halogen; (b) hydroxy; (c) $C_1$-$C_3$ alkoxy; (d) $NR^kR^m$; (e) $C_3$-$C_6$ cylcoalkyl optionally substituted with one or two $R^h$ groups; (f) a 4 to 6 membered heterocyclyl containing one to three heteroatoms selected from N, O and S, wherein the heterocyclyl may be optionally substituted with one group selected from $C_1$-$C_3$ alkyl optionally substituted with halogen, —C(=O)O($C_1$-$C_6$ alkyl) and phenyl; (g) phenyl optionally substituted with one or two $R^j$ groups; and (h) a 5 to 6 membered heteroaryl containing one to four heteroatoms selected from N, O and S, wherein the heteroaryl may be optionally substituted with one or two $R^j$ groups;

each $R^g$ is selected from (a) halogen; (b) $C_1$-$C_3$ alkyl optionally substituted with phenyl optionally substituted with two groups selected from halogen and $C_1$-$C_3$ alkoxy; (c) $C_1$-$C_3$ alkoxy; (d) phenyl optionally substituted with halogen; and (e) a 5 to 6 membered heteroaryl containing one N heteroatom optionally substituted with one or two groups selected from halogen and $C_1$-$C_3$ alkoxy;

each $R^h$ is selected from halogen, $C_1$-$C_3$ alkyl, $C_1$-$C_3$ alkoxy and phenyl optionally substituted with $C_1$-$C_3$ alkoxy optionally substituted with halogen;

each $R^j$ is selected from halogen, $C_1$-$C_3$ alkyl and $C_1$-$C_3$ alkoxy, wherein the alkyl and alkoxy may be optionally substituted with halogen; and each $R^k$ and $R^m$ are independently $C_1$-$C_3$ alkyl.

In certain embodiments, $X_1$ is CH (such compound have the structure of Formula II). In certain embodiments, $X_1$ is N (such compounds have the structure of Formula III).

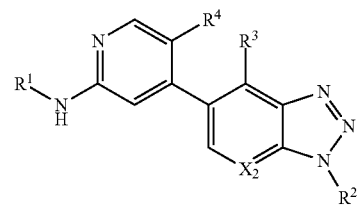

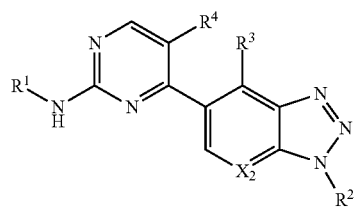

In certain embodiments, $X_2$ is CH (such compounds have the structure of Formula IV). In certain embodiments, $X_2$ is N (such compounds have the structure of Formula V).

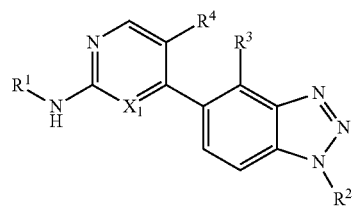

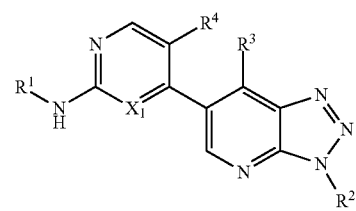

In certain embodiments, $X_1$ is CH and $X_2$ is CH (such compounds have the structure of Formula VI). In certain embodiments, $X_1$ is CH and $X_2$ is N (such compounds have the structure of Formula VII). In certain embodiments, $X_1$ is N and $X_2$ is CH (such compounds have the structure of Formula VIII). In certain embodiments, $X_1$ is N and $X_2$ is N (such compounds have the structure of Formula IX).

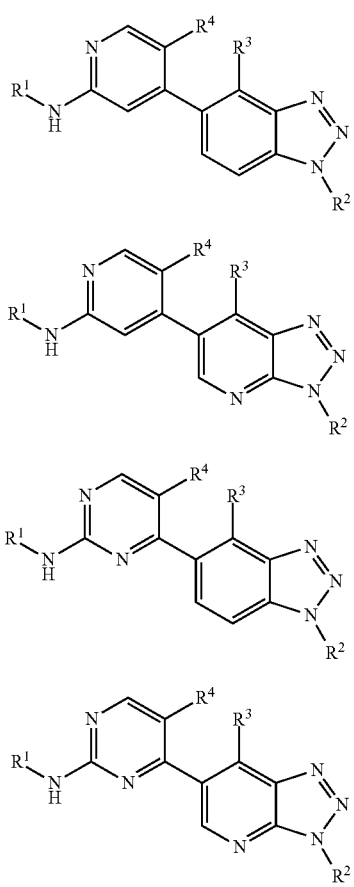

In certain embodiments, $X_1$ is CH and $X_2$ is CH; $X_1$ is CH and $X_2$ is N; or $X_1$ is N and $X_2$ is CH.

International Patent Application Publications WO 2012/118850 (—NH—$R^b$ of Formula I), WO 2013/020062 (—NH—$R^2$ of Formula I) and WO 2013/130976 (—NH—$R^1$) disclose amines that may be used in the instant application at the —NH—$R^1$ position of Formula I, II, III, IV, V, VI, VII, VIII, IX or X.

In certain embodiments, $R^1$ is selected from (a) $C_1$-$C_6$ alkyl optionally substituted with one or more groups independently selected from halogen, $OR^a$, $NR^bR^c$, oxo, CN, $C_3$-$C_6$ cycloalkyl and a 3 to 7 membered heterocycle; (b) $C_3$-$C_7$ cycloalkyl optionally substituted with one or more groups independently selected from halogen, $OR^a$, CN and $C_1$-$C_3$ alkyl optionally substituted with one or more groups independently selected from halogen and $OR^d$; (c) phenyl optionally substituted with one or more groups independently selected from halogen, $OR^a$, CN, $C_3$-$C_6$ cycloalkyl and $C_1$-$C_3$ alkyl optionally substituted with one or more groups independently selected from halogen and $OR^d$; (d) a 3 to 7 membered saturated or partially unsaturated heterocyclyl optionally substituted with one or more groups independently selected from halogen, $OR^a$, oxo, CN, $C_3$-$C_6$ cycloalkyl and $C_1$-$C_3$ alkyl optionally substituted with one or more groups independently selected from halogen and $OR^d$; (e) a 5 to 6 membered heteroaryl optionally substituted with one or more groups independently selected from halogen, $OR^e$, oxide, CN, $C_3$-$C_6$ cycloalkyl and $C_1$-$C_3$ alkyl optionally substituted with one or more groups independently selected from halogen, oxo and $OR^d$; and (f) a 7 to 10 membered bicyclic heterocycle optionally substituted with one or more groups independently selected from halogen, $OR^a$, oxo, CN, $C_3$-$C_6$ cycloalkyl and $C_1$-$C_3$ alkyl optionally substituted with one or more groups independently selected from halogen and $OR^d$; wherein each $R^a$, $R^b$, $R^c$, $R^d$ and $R^e$ are independently selected from hydrogen and $C_1$-$C_6$ alkyl.

In certain embodiments, $R^1$ is selected from (a) $C_1$-$C_6$ alkyl optionally substituted with one or more groups independently selected from halogen, $OR^a$, $NR^bR^c$, oxo, CN, $C_3$-$C_6$ cycloalkyl and a 3 to 7 membered heterocycle, wherein the heterocycle contains one, two or three heteroatoms selected from the group consisting of O, N, S, S(═O) and S(═O)$_2$, (b) $C_3$-$C_7$ cycloalkyl optionally substituted with one or more groups independently selected from halogen, $OR^a$, CN and $C_1$-$C_3$ alkyl optionally substituted with one or more groups independently selected from halogen and $OR^d$, (c) phenyl optionally substituted with one or more groups independently selected from halogen, $OR^a$, CN, $C_3$-$C_6$ cycloalkyl and $C_1$-$C_3$ alkyl optionally substituted with one or more groups independently selected from halogen and $OR^d$, (d) a 3 to 7 membered saturated or partially unsaturated heterocycle optionally substituted with one or more groups independently selected from halogen, $OR^a$, oxo, CN, $C_3$-$C_6$ cycloalkyl and $C_1$-$C_3$ alkyl optionally substituted with one or more groups independently selected from halogen and $OR^d$, wherein the heterocycle contains one, two or three heteroatoms selected from the group consisting of O, N, S, S(═O) and S(═O)$_2$, (e) a 5 to 6 membered heteroaryl optionally substituted with one or more groups independently selected from halogen, $OR^e$, oxide, CN, $C_3$-$C_6$ cycloalkyl and $C_1$-$C_3$ alkyl optionally substituted with one or more groups independently selected from halogen, oxo and $OR^d$, wherein the heteroaryl contains one, two, three or four heteroatoms selected from the group consisting of O, N and S, and (f) a 7 to 10 membered bicyclic heterocycle optionally substituted with one or more groups independently selected from halogen, $OR^a$, oxo, CN, $C_3$-$C_6$ cycloalkyl and $C_1$-$C_3$ alkyl optionally substituted with one or more groups independently selected from halogen and $OR^d$, wherein the heterocycle contains one, two or three heteroatoms selected from the group consisting of O, N, S, S(═O) and S(═O)$_2$; wherein each $R^a$, $R^b$, $R^c$, $R^d$ and $R^e$ are independently selected from hydrogen and $C_1$-$C_6$ alkyl.

In certain embodiments, $R^1$ is selected from (a) $C_1$-$C_6$ alkyl optionally substituted with one to six groups independently selected from halogen, $OR^a$, $NR^bR^c$, $C_3$-$C_6$ cycloalkyl and a 3 to 7 membered heterocycle, wherein the heterocycle contains one, two or three heteroatoms selected from the group consisting of O, N, S, S(═O) and S(═O)$_2$, (b) $C_3$-$C_7$ cycloalkyl optionally substituted with one to four groups independently selected from halogen and $OR^a$, (c) phenyl optionally substituted with one to four groups independently selected from halogen and $C_1$-$C_3$ alkyl, (d) a 3 to 7 membered saturated or partially unsaturated heterocycle optionally substituted with one to four groups independently selected from halogen, oxo, $OR^a$ and $C_1$-$C_3$ alkyl optionally substituted with $OR^d$, wherein the heterocycle contains one, two or three heteroatoms selected from the group consisting of O, N, S, S(═O) and S(═O)$_2$, (e) a 5 to 6 membered heteroaryl optionally substituted with one to four groups independently selected from halogen, CN, $OR^e$, $C_3$-$C_6$ cycloalkyl, oxide and $C_1$-$C_3$ alkyl optionally substituted with one to three groups independently selected from hydroxyl, methoxy, oxo and halogen, wherein the heteroaryl contains one, two, three or four heteroatoms selected from the group consisting of O, N and S, and (f) a 7 to 10 membered bicyclic heterocycle optionally substituted with one or two groups selected from $C_1$-$C_3$ alkyl and oxo, wherein the heterocycle contains one, two or three heteroatoms selected from the group consisting of O, N, S, S(=O) and S(=O)$_2$; wherein each $R^a$, $R^b$, $R^c$, $R^d$ and $R^e$ are independently selected from hydrogen and $C_1$-$C_6$ alkyl.

In certain embodiments, $R^1$ is selected from optionally substituted $C_1$-$C_{10}$ alkyl; optionally substituted aryl or aryl-$C_1$-$C_6$ alkyl; optionally substituted heteroaryl or heteroaryl-$C_1$-$C_6$ alkyl, wherein said heteroaryl is selected from the group consisting of isoxazole, pyridinyl, pyridone, pyrimidinyl, pyrazinyl, pyrazole, thiazolyl, triazolyl, N—$C_1$-$C_6$ alkyl-pyrazolyl, N-benzylpyrazolyl, N—$C_1$-$C_6$ alkyl triazolyl and 2-oxo-tetrahydroquinolin-6-yl; heterocyclyl or heterocyclyl-$C_1$-$C_6$ alkyl, wherein said heterocyclyl is selected from the group consisting of tetrahydropyranyl, tetrahydrofuranyl, piperidinyl, pyrrolidinyl, morpholinyl, N—$C_1$-$C_6$ alkyl-piperidinyl and N—$C_1$-$C_6$ alkyl-2-oxo-pyrrolidinyl; and $C_3$-$C_7$ cycloalkyl or $C_3$-$C_7$ cycloalkyl-$C_1$-$C_6$ alkyl; wherein the alkyl, aryl, heteroaryl, heterocyclyl and cycloalkyl are optionally substituted with OH, oxo (except not on aromatic rings), halogen, CN, $C_1$-$C_4$ alkyl, $C_1$-$C_4$ hydroxyalkyl, $C_1$-$C_6$ alkoxy, benzyl, phenyl, $C_3$-$C_7$ cycloalkyl, 3 to 6 membered heterocyclyl or 5 to 6 membered heteroaryl, wherein the phenyl, cycloalkyl, heterocyclyl and heteroaryl are optionally substituted with halogen or $C_1$-$C_4$ alkyl.

In certain embodiments, $R^1$ is in the (S) configuration. In certain embodiments, $R^1$ is in the (R) configuration.

In certain embodiments, $R^1$ is selected from methyl, ethyl, isopropyl, tert-butyl, isobutyl, 2-hydroxyethyl, 1-hydroxymethylpropyl, 2-hydroxy-1-methyl-ethyl (or 1-hydroxypropan-2-yl), 2-methoxy-1-methyl-ethyl, 2-hydroxypropyl, 2-hydroxy-1-hydroxymethyl-ethyl, 1-hydroxy-2,2-dimethylpropan-3-yl, 2-hydroxy-2-methylpropan-1-yl, 1,2-dihydroxypropan-3-yl, acetyl, 2,2,2-trifluoro-1-methyl-ethyl, 2,2,2-trifluoro-1-hydroxymethyl-ethyl, 2-fluoro-1-methyl-ethyl, 2-fluoro-1-fluoromethyl-ethyl, 2,2,2-trifluoroethyl, 3,3,3-trifluoropropyl, cyclopropylmethyl, 2-morpholin-4-yl-ethyl, 2,2-difluoro-1-methyl-ethyl, oxetan-3-ylmethyl, 2-methyl-1-morpholinopropan-2-yl, 4-fluorophenyl, 3-chloro-4-fluorophenyl, 4-chloro-3-fluorophenyl, 2-o-tolyl, 4-fluoro-2-methylphenyl, 2-chlorophenyl, 2-chloro-4-fluorophenyl, 4-fluoro-2-trifluoromethylphenyl, 4-cyano-2-fluorophenyl, pyrimidin-5-yl, 4-methylpyrimidin-5-yl, 2-methylpyrimidin-4-yl, 6-methylpyrimidin-4-yl, 2-oxo-1,2,3,4-tetrahydroquinolin-6-yl, 3,5-dimethylisoxazol-4-yl, 2-methylpyridin-4-yl, 4-chloropyridin-2-yl, 2-methylpyridin-3-yl, 2-methylpyridin-4-yl, 2-ethoxypyridin-4-yl, 2-cyclopropylpyridin-4-yl, 1-methyl-1H-pyrazol-4-yl, 1-ethyl-1H-pyrazol-4-yl, 1-methyl-1H-pyrazol-3-yl, 2-ethyl-2H-pyrazol-3-yl, 1-benzyl-1H-pyrazol-4-yl, 2-methyl-2H-pyrazol-3-yl, 2-isopropyl-2H-pyrazol-3-yl, 1-methyl-1H-pyrazol-5-yl, 1,3-dimethyl-1H-pyrazol-4-yl, 1,3,5-trimethyl-1H-pyrazol-4-yl, 3-cyclopropyl-1-methyl-1H-pyrazol-5-yl, 1-methyl-6-oxo-1,6-dihydropyridin-3-yl, 4-methylthiazol-2-yl, 1-methyl-1H-[1,2,4]triazol-3-yl, 2-methyl-2H-1,2,3-triazol-4-yl, 1-methyl-1H-1,2,4-triazol-5-yl, 5-chloropyrazin-2-yl, 1-methyl-1H-tetrazol-5-yl, 2-methyl-2H-tetrazol-5-yl, 5-methyl-1,3,4-thiadiazol-2-yl, oxetan-3-yl, 3-methyloxetan-3-yl, tetrahydropyran-4-yl, tetrahydro-2H-pyran-4-yl, tetrahydropyran-3-yl, 2-methyl-tetrahydropyran-4-yl, 2,2-dimethyl-tetrahydropyran-4-yl, 2-hydroxymethyltetrahydropyran-4-yl, 3-fluorotetrahydropyran-4-yl, 1-methylpiperidin-4-yl, 1-methyl-5-oxo-pyrrolidin-3-yl, tetrahydrofuran-3-yl, cyclopropyl, cyclopentyl, cyclobutyl, 3-hydroxycyclopentyl, 3,3-difluorocyclopentyl, 4-hydroxycyclohexyl, 3,3-difluorocyclobutyl, 3-hydroxycyclobutyl and 4,4-difluorocyclohexyl. In another embodiment, $R^1$ is selected from (S)-2-hydroxy-1-methyl-ethyl, (S)-1-hydroxymethyl-propyl, (1S,3S)-3-hydroxycyclopentyl and tetrahydropyran-4-yl. In another embodiment, $R^1$ is selected from (S)-2-hydroxy-1-methyl-ethyl, (S)-1-hydroxymethyl-propyl, (1S,3S)-3-hydroxycyclopentyl, tetrahydropyran-4-yl, isopropyl, 1-methyl-1H-pyrazol-5-yl, 1-methyl-1H-pyrazol-4-yl, 2-methyl-2H-1,2,3-triazol-4-yl and 1-methyl-1H-1,2,4-triazol-5-yl. In certain embodiments, $R^1$ is selected from 1-methyl-1H-pyrazol-5-yl, 1-methyl-1H-pyrazol-4-yl, tetrahydro-2H-pyran-4-yl, (S)-2-hydroxy-1-methyl-ethyl, (S)-1-hydroxymethyl-propyl and (1S,3S)-3-hydroxycyclopentyl.

In certain embodiments, $R^1$ is selected from methyl, ethyl, isopropyl, tert-butyl, isobutyl, 2-hydroxyethyl, 1-hydroxymethylpropyl, 2-hydroxy-1-methyl-ethyl (or 1-hydroxypropan-2-yl), 2-methoxy-1-methyl-ethyl, 2-hydroxypropyl, 2-hydroxy-1-hydroxymethyl-ethyl, acetyl, 2,2,2-trifluoro-1-methyl-ethyl, 2,2,2-trifluoro-1-hydroxymethyl-ethyl, 2-fluoro-1-methyl-ethyl, 2-fluoro-1-fluoromethyl-ethyl, 2,2,2-trifluoroethyl, 3,3,3-trifluoropropyl, cyclopropylmethyl, 2-morpholin-4-yl-ethyl, 2,2-difluoro-1-methyl-ethyl, 4-fluorophenyl, 3-chloro-4-fluorophenyl, 4-chloro-3-fluorophenyl, 2-o-tolyl, 4-fluoro-2-methylphenyl, 2-chlorophenyl, 2-chloro-4-fluorophenyl, 4-fluoro-2-trifluoromethylphenyl, 4-cyano-2-fluorophenyl, pyrimidin-5-yl, 4-methylpyrimidin-5-yl, 2-methylpyrimidin-4-yl, 6-methylpyrimidin-4-yl, 2-oxo-1,2,3,4-tetrahydroquinolin-6-yl, 3,5-dimethylisoxazol-4-yl, 2-methylpyridin-4-yl, 4-chloropyridin-2-yl, 2-methylpyridin-3-yl, 2-methylpyridin-4-yl, 2-ethoxypyridin-4-yl, 2-cyclopropylpyridin-4-yl, 1-methyl-1H-pyrazol-4-yl, 1-ethyl-1H-pyrazol-4-yl, 1-methyl-1H-pyrazol-3-yl, 2-ethyl-2H-pyrazol-3-yl, 1-benzyl-1H-pyrazol-4-yl, 2-methyl-2H-pyrazol-3-yl, 2-isopropyl-2H-pyrazol-3-yl, 1-methyl-1H-pyrazol-5-yl, 1-methyl-6-oxo-1,6-dihydropyridin-3-yl, 4-methylthiazol-2-yl, 1-methyl-1H-[1,2,4]triazol-3-yl, 2-methyl-2H-1,2,3-triazol-4-yl, 5-chloropyrazin-2-yl, tetrahydropyran-4-yl, tetrahydro-2H-pyran-4-yl, tetrahydropyran-3-yl, 2-methyl-tetrahydropyran-4-yl, 2,2-dimethyl-tetrahydropyran-4-yl, 2-hydroxymethyltetrahydropyran-4-yl, 3-fluorotetrahydropyran-4-yl, 1-methylpiperidin-4-yl, 1-methyl-5-oxo-pyrrolidin-3-yl, tetrahydrofuran-3-yl, cyclopentyl, 3-hydroxycyclopentyl, 3,3-difluorocyclopentyl, 4-hydroxycyclohexyl, 3,3-difluorocyclobutyl, 3-hydroxycyclobutyl and 4,4-difluorocyclohexyl. In another embodiment, $R^1$ is selected from (S)-2-hydroxy-1-methyl-ethyl, (S)-1-hydroxymethyl-propyl, (1S,3S)-3-hydroxycyclopentyl and tetrahydropyran-4-yl. In another embodiment, $R^1$ is selected from (S)-2-hydroxy-1-methyl-ethyl, (S)-1-hydroxymethyl-propyl, (1S,3S)-3-hydroxycyclopentyl, tetrahydropyran-4-yl, isopropyl, 1-methyl-1H-pyrazol-5-yl, 1-methyl-1H-pyrazol-4-yl and 1-methyl-1H-1,2,4-triazol-5-yl. In certain embodiments, $R^1$ is selected from 1-methyl-1H-pyrazol-5-yl, 1-methyl-1H-pyrazol-4-yl, tetrahydro-2H-pyran-4-yl, (S)-2-hydroxy-1-methyl-ethyl, (S)-1-hydroxymethyl-propyl and (1S,3S)-3-hydroxycyclopentyl.

In certain embodiments, $R^1$ is selected from the group consisting of (a) $C_1$-$C_{10}$ alkyl; (b) $C_1$-$C_6$ haloalkyl; (c) heterocyclyl or heterocyclyl-$C_1$-$C_6$ alkyl, wherein said heterocycle or heterocyclyl-$C_1$-$C_6$ alkyl is selected from the group consisting of tetrahydropyranyl, tetrahydrofuranyl, oxetanyl, piperidinyl, N—$C_1$-$C_6$ alkyl-piperidinyl and N—$C_1$-$C_6$ alkyl-2-oxo-pyrrolidinyl, and wherein said heterocycle or heterocyclyl-$C_1$-$C_6$ alkyl is optionally substituted by 1 to 3 groups independently selected from $C_1$-$C_6$ alkyl, $C_1$-$C_6$ haloalkyl, $C_1$-$C_4$ acyloxy-$C_1$-$C_2$ alkyl, halogen, hydroxyl, phenyl, $C_1$-$C_3$ hydroxyalkyl and oxo; (d) $C_3$-$C_7$ cycloalkyl or $C_3$-$C_7$ cycloalkyl-$C_1$-$C_6$ alkyl, wherein said cycloalkyl is optionally substituted by hydroxyl or halo; and (e) $C_1$-$C_6$ heteroalkyl.

In certain embodiments, $R^1$ is selected from the group consisting of (a) $C_1$-$C_{10}$ alkyl; (b) $C_1$-$C_6$ haloalkyl; (c) heterocyclyl or heterocyclyl-$C_1$-$C_6$ alkyl, wherein said heterocycle or heterocyclyl-$C_1$-$C_6$ alkyl is selected from the group consisting of tetrahydropyranyl, tetrahydrofuranyl, oxetanyl, piperidinyl, N—$C_1$-$C_6$ alkyl-piperidinyl and N—$C_1$-$C_6$ alkyl-2-oxo-pyrrolidinyl, and wherein said heterocycle or heterocyclyl-$C_1$-$C_6$ alkyl is optionally substituted by 1 to 3 groups independently selected from $C_1$-$C_6$ alkyl, $C_1$-$C_4$ acyloxy-$C_1$-$C_2$ alkyl, halogen, and $C_1$-$C_3$ hydroxyalkyl; (d) $C_3$-$C_7$ cycloalkyl or $C_3$-$C_7$ cycloalkyl-$C_1$-$C_6$ alkyl, wherein said cycloalkyl is optionally substituted by hydroxyl or halo; and (e) $C_1$-$C_6$ heteroalkyl.

In certain embodiments, each $R^a$ is independently selected from hydrogen and $C_1$-$C_6$ alkyl. In certain embodiments, each $R^a$ is independently selected from hydrogen and $C_1$-$C_3$ alkyl. In certain embodiments, each $R^a$ is independently selected from hydrogen and methyl.

In certain embodiments, each $R^b$ and $R^c$ are independently selected from hydrogen and $C_1$-$C_6$ alkyl. In certain embodiments, each $R^b$ and $R^c$ are independently selected from hydrogen and $C_1$-$C_3$ alkyl. In certain embodiments, each $R^b$ and $R^c$ are independently selected from hydrogen and methyl.

In certain embodiments, each $R^d$ is independently selected from hydrogen and $C_1$-$C_6$ alkyl. In certain embodiments, each $R^d$ is independently selected from hydrogen and $C_1$-$C_3$ alkyl. In certain embodiments, each $R^d$ is selected from hydrogen and methyl.

In certain embodiments, each $R^e$ is independently selected from hydrogen and $C_1$-$C_6$ alkyl. In certain embodiments, each $R^e$ is independently selected from hydrogen and $C_1$-$C_3$ alkyl. In certain embodiments, each $R^e$ is independently selected from methyl and ethyl.

In certain embodiments, $R^1$ is selected from 1-hydroxypropan-2-yl, isopropyl, 1-hydroxybutan-2-yl, 1-cyclopropylethyl, 1-hydroxy-3-methoxypropan-2-yl, 1,3-difluoropropan-2-yl, 1-cyclopropyl-2-hydroxyethyl, oxetan-3-ylmethyl, 4-methoxybutan-2-yl, 4,4,4-trifluoro-1-hydroxybutan-2-yl, 1-aminopropan-2-yl, 1-hydroxy-2,2-dimethylpropan-3-yl, 2-hydroxy-2-methylpropan-1-yl, 1,2-dihydroxypropan-3-yl, 3-hydroxycyclopentyl, 3,3-difluorocyclobutyl, 3-hydroxycyclobutyl, cyclopropylmethyl, 2-methyl-1-morpholinopropan-2-yl, 2-chloro-4-fluorophenyl, 4-fluoro-2-methylphenyl, tetrahydropyran-4-yl, 3-fluorotetrahydropyran-4-yl, tetrahydrodioxothiopyran-4-yl, 1,1-dioxotetrahydrothiophen-3-yl, oxetan-3-yl, 3-methyloxetan-3-yl, tetrahydrofuran-3-yl, 2,2-dimethyltetrahydropyran-4-yl, 2-methyltetrahydropyran-4-yl, pyrrolidin-3-yl, azetidin-3-yl, piperdin-3-yl, 2-(hydroxymethyl)tetrahydropyran-4-yl, 6-oxo-1,6-dihydropyridin-3-yl, 1-methylpyrazol-4-yl, 2-methylpyrimidin-4-yl, 6-methylpyrimidin-4-yl, 6-methoxypyrimidin-4-yl, 2-methylpyridin-4-yl, 1,3-dimethylpyrazol-4-yl, 2-methoxypyridin-4-yl, 1-methylpyrazol-3-yl, 6-methoxypyridin-3-yl, 2-ethylpyrimidin-4-yl, 6-methylpyridin-2-yl, 2-cyclopropylpyrimidin-4-yl, 5-fluoro-6-methylpyridin-2-yl, 5-cyclopropyl-1-methylpyrazol-4-yl, 5-bromo-2-methylpyridin-4-yl, 1,5-dimethylpyrazol-4-yl, 1,3-dimethylpyrazol-5-yl, 4-(2-hydroxypropan-2-yl)pyridin-2-yl, 1-ethyl-3-methypyrazol-4-yl, 5-ethoxy-2-methylpyridin-4-yl, 1-isopropylpyrazol-4-yl, 4-methylimidazol-5-yl, 1-methylimidazol-5-yl, 1-ethylpyrazol-4-yl, 2-(2-hydroxypropan-2-yl)pyridin-4-yl, 1-methyl-4-cyanopyrazol-5-yl, 3-methylpyridin-4-yl, 1-ethyl-3-methylpyrazol-5-yl, 1-methylpyrazol-5-yl, 1,4-dimethylpyrazol-5-yl, 1-ethylpyrazol-5-yl, 3-isopropyl-1-methylpyrazol-5-yl, 3-methylpyrazol-4-yl, 3-ethyl-1-methylpyrazol-4-yl, 1,3,5-trimethylpyrazol-4-yl, 3,5-dimethylpyrazol-4-yl, 2-cyclopropyl-5-methoxypyridin-4-yl, 5-ethyl-1-methylpyrazol-4-yl, 4-(2-methoxypyridine 1-oxide), 5-methoxy-2-methylpyridin-4-yl, 5-methyl-1,3,4-oxadizol-2-yl, 3-ethyl-1-methylpyrazol-5-yl, 1-(2-hydroxyethyl)-3-methylpyrazol-4-yl, 1-(2-hydroxyethyl)-5-methylpyrazol-4-yl, 1-methyl-3-(trifluoromethyl)pyrazol-4-yl, 1-methyl-3-(trifluoromethyl)pyrazol-5-yl, 1-methyl-1,2,3-triazol-5-yl, 2-methyl-1,2,3-triazol-4-yl, 1-methyl-1,2,4-triazol-5-yl, 2-methylpyridin-4-yl, 1-(2-hydroxyethyl)pyrazol-5-yl, methyl 4-picolinate, 4-picolinic acid, 1-cyclopropyl-5-methylpyrazol-4-yl, 1-cyclopropyl-3-methylpyrazol-4-yl, 2,3-dimethylpyridin-4-yl, 2,5-dimethylpyrazol-4-yl, 1,3,4-oxadizol-2-yl, 3-methylpyridazin-4-yl, pyridazin-4-yl, tetrazol-5-yl, 1-methyltetrazol-5-yl, 3-cyclopropyl-1-methylpyrazol-5-yl, 2-methyltetrazol-5-yl, 5-methyl-1,3,4-thiadiazol-2-yl, 2-methyl-2,4,5,6-tetrahydrocyclopentapyrazol-3-yl, 3-oxo-2-oxabicyclo[2.2.1]heptan-5-yl and 2-oxabicyclo[2.2.1]heptan-5-yl.

In certain embodiments, $R^1$ is selected from 1-hydroxypropan-2-yl, isopropyl, 1-hydroxybutan-2-yl, 1-cyclopropylethyl, 1-hydroxy-3-methoxypropan-2-yl, 1,3-difluoropropan-2-yl, 1-cyclopropyl-2-hydroxyethyl, oxetan-3-ylmethyl, 4-methoxybutan-2-yl, 4,4,4-trifluoro-1-hydroxybutan-2-yl, 1-aminopropan-2-yl, 1-hydroxy-2,2-dimethylpropan-3-yl, 2-hydroxy-2-methylpropan-1-yl, 1,2-dihydroxypropan-3-yl, 3-hydroxycyclopentyl, 3,3-difluorocyclobutyl, 3-hydroxycyclobutyl, cyclopropylmethyl, 2-methyl-1-morpholinopropan-2-yl, 2-chloro-4-fluorophenyl, 4-fluoro-2-methylphenyl, tetrahydropyran-4-yl, 3-fluorotetrahydropyran-4-yl, tetrahydrodioxothiopyran-4-yl, 1,1-dioxotetrahydrothiophen-3-yl, oxetan-3-yl, 3-methyloxetan-3-yl, tetrahydrofuran-3-yl, 2,2-dimethyltetrahydropyran-4-yl, 2-methyltetrahydropyran-4-yl, pyrrolidin-3-yl, azetidin-3-yl, piperdin-3-yl, 2-(hydroxymethyl)tetrahydropyran-4-yl, 6-oxo-1,6-dihydropyridin-3-yl, 1-methylpyrazol-4-yl, 2-methylpyrimidin-4-yl, 6-methylpyrimidin-4-yl, 6-methoxypyrimidin-4-yl, 2-methylpyridin-4-yl, 1,3-dimethylpyrazol-4-yl, 2-methoxypyridin-4-yl, 1-methylpyrazol-3-yl, 6-methoxypyridin-3-yl, 2-ethylpyrimidin-4-yl, 6-methylpyridin-2-yl, 2-cyclopropylpyrimidin-4-yl, 5-fluoro-6-methylpyridin-2-yl, 5-cyclopropyl-1-methylpyrazol-4-yl, 5-bromo-2-methylpyridin-4-yl, 1,5-dimethylpyrazol-4-yl, 1,3-dimethylpyrazol-5-yl, 4-(2-hydroxypropan-2-yl)pyridin-2-yl, 1-ethyl-3-methypyrazol-4-yl, 5-ethoxy-2-methylpyridin-4-yl, 1-isopropylpyrazol-4-yl, 4-methylimidazol-5-yl, 1-methylimidazol-5-yl, 1-ethylpyrazol-4-yl, 2-(2-hydroxypropan-2-yl)pyridin-4-yl, 1-methyl-4-cyanopyrazol-5-yl, 3-methylpyridin-4-yl, 1-ethyl-3-methylpyrazol-5-yl, 1-methylpyrazol-5-yl, 1,4-dimethylpyrazol-5-yl, 1-ethylpyrazol-5-yl, 3-isopropyl-1-methylpyrazol-5-yl, 3-methylpyrazol-4-yl, 3-ethyl-1-methylpyrazol-4-yl, 1,3,5-trimethylpyrazol-4-yl, 3,5-dimethylpyrazol-4-yl, 2-cyclopropyl-5-methoxypyridin-4-yl, 5-ethyl-1-methylpyrazol-4-yl, 4-(2-methoxypyridine 1-oxide), 5-methoxy-2-methylpyridin-4-yl, 5-methyl-1,3,4-oxadizol-2-yl, 3-ethyl- 1-methylpyrazol-5-yl, 1-(2-hydroxyethyl)-3-methylpyrazol-4-yl, 1-(2-hydroxyethyl)-5-methylpyrazol-4-yl, 1-methyl-3-(trifluoromethyl)pyrazol-4-yl, 1-methyl-3-(trifluoromethyl) pyrazol-5-yl, 1-methyl-1,2,3-triazol-5-yl, 2-methyl-1,2,3-triazol-4-yl, 2-methylpyridin-4-yl, 1-(2-hydroxyethyl) pyrazol-5-yl, methyl 4-picolinate, 4-picolinic acid, 1-cyclopropyl-5-methylpyrazol-4-yl, 1-cyclopropyl-3-methylpyrazol-4-yl, 2,3-dimethylpyridin-4-yl, 2,5-dimethylpyridin-4-yl, 1,3,4-oxadizol-2-yl, 3-methylpyridazin-4-yl, pyridazin-4-yl, tetrazol-5-yl, 1-methyltetrazol-5-yl, 3-cyclopropyl-1-methylpyrazol-5-yl, 2-methyltetrazol-5-yl, 5-methyl-1,3,4-thiadiazol-2-yl, 2-methyl-2,4,5,6-tetrahydro cyclopentapyrazol-3-yl, 3-oxo-2-oxabicyclo[2.2.1]heptan-5-yl and 2-oxabicyclo[2.2.1]heptan-5-yl.

In certain embodiments, $R^1$ is selected from the group consisting of (a) $C_1$-$C_{10}$ alkyl; (b) $C_1$-$C_6$ haloalkyl; (c) heterocyclyl or heterocyclyl-$C_1$-$C_6$ alkyl, wherein said heterocycle or heterocyclyl-$C_1$-$C_6$ alkyl is selected from the group consisting of tetrahydropyranyl, tetrahydrofuranyl and oxetanyl and wherein said heterocycle is optionally substituted by $C_1$-$C_6$ alkyl, halogen, $C_1$-$C_3$ hydroxyalkyl or $C_1$-$C_4$ acyloxy-$C_1$-$C_2$ alkyl; (d) $C_3$-$C_7$ cycloalkyl or $C_3$-$C_7$ cycloalkyl-$C_1$-$C_6$ alkyl, wherein said cycloalkyl is optionally substituted by hydroxyl; and (e) $C_1$-$C_6$ heteroalkyl.

In certain embodiments, $R^1$ is selected from the group consisting of (a) tetrahydropyranyl; (b) tetrahydrofuranyl; (c) oxetanyl; (d) 2-hydroxy-1-methyl-ethan-1-yl; (e) 2,2,2-trifluoro-1-methyl-ethan-1-yl; (f) 1-cyclopropyl-ethan-1-yl; (g) 2-methoxyethyl; (h) 3-fluoropropyl; (i) cyclopropylmethyl; (j) oxetanylmethyl; (k) 4-hydroxycyclohexyl; and (l) pyrazolyl;

wherein said (a) tetrahydropyranyl, (b) tetrahydrofuranyl and (c) oxetanyl are optionally substituted with one to three groups independently selected from $C_1$-$C_6$ alkyl, $C_1$-$C_6$ haloalkyl, $C_1$-$C_4$ acyloxy-$C_1$-$C_2$ alkyl, $C_1$-$C_3$ hydroxyalkyl and halogen; and wherein said (l) pyrazolyl moiety is optionally substituted with one to three groups independently selected from $C_1$-$C_6$ alkyl, $C_1$-$C_6$ haloalkyl and halogen.

In certain embodiments, $R^1$ is selected from the group consisting of 1-hydroxypropan-2-yl, isopropyl, 1-cyclopropylethyl, cyclopropylmethyl, 4-hydroxycyclohexyl, 1,1,1-trifluoropropan-2-yl, 3-fluoropropyl, tetrahydro-2H-pyran-4-yl, 3-fluorotetrahydropyran-4-yl, 2-(hydroxymethyl) tetrahydropyran-4-yl, (4-tetrahydro-2H-pyran-2-yl)methyl acetate, tetrahydrofuran-3-yl, 3-methyloxetan-3-yl, oxetany-3-ylmethyl, 2-methoxyethyl, 1-methyl-1H-pyrazol-5-yl, 1-methyl-1H-pyrazol-4-yl, 2-methylpyrazol-3-yl, 2,5-dimethylpyrazol-3-yl, 1,3-dimethylpyrazol-4-yl, 2-methyl-2H-1,2,3-triazol-4-yl and 1-methyl-1H-1,2,4-triazol-5-yl.

In certain embodiments, $R^1$ is selected from the group consisting of 1-hydroxypropan-2-yl, isopropyl, 1-cyclopropylethyl, cyclopropylmethyl, 4-hydroxycyclohexyl, 1,1,1-trifluoropropan-2-yl, 3-fluoropropyl, tetrahydro-2H-pyran-4-yl, 3-fluorotetrahydropyran-4-yl, 2-(hydroxymethyl) tetrahydropyran-4-yl, (4-tetrahydro-2H-pyran-2-yl)methyl acetate, tetrahydrofuran-3-yl, 3-methyloxetan-3-yl, oxetany-3-ylmethyl, 2-methoxyethyl, 1-methyl-1H-pyrazol-5-yl, 1-methyl-1H-pyrazol-4-yl, 2-methylpyrazol-3-yl, 2,5-dimethylpyrazol-3-yl, 1,3-dimethylpyrazol-4-yl and 2-methyl-2H-1,2,3-triazol-4-yl.

In certain embodiments, $R^1$ is selected from (a) $C_1$-$C_6$ alkyl optionally substituted with one to three groups selected from halogen, OH, cyclopropyl and a a 4 to 6 membered heterocyclyl containing one to three heteroatoms selected from N, O and S; (b) $C_3$-$C_6$ cycloalkyl optionally substituted with one to three groups selected from halogen, OH and $C_1$-$C_3$ alkyl; (c) a 4 to 6 membered heterocyclyl containing one to three heteroatoms selected from N, O and S, optionally substituted with one to three groups selected from halogen, OH and $C_1$-$C_3$ alkyl; and (d) a 5 to 6 membered heteroaryl containing one to four heteroatoms selected from N, O and S, optionally substituted with one to three groups selected from halogen, OH, $C_1$-$C_3$ alkyl and cyclopropyl. In certain embodiments, $R^1$ is selected from (a) $C_1$-$C_6$ alkyl optionally substituted with one or two groups selected from halogen, OH, cyclopropyl and a a 4 to 6 membered heterocyclyl containing one to three heteroatoms selected from N, O and S; (b) $C_3$-$C_6$ cycloalkyl optionally substituted with one or two groups selected from halogen, OH and methyl; (c) a 4 to 6 membered heterocyclyl containing one to three heteroatoms selected from N, O and S, optionally substituted with one or two groups selected from halogen, OH and methyl; and (d) a 5 to 6 membered heteroaryl containing one to four heteroatoms selected from N, O and S, optionally substituted with one to three groups selected from halogen, OH, methyl and cyclopropyl.

In certain embodiments, $R^1$ is selected from (a) $C_1$-$C_6$ alkyl optionally substituted with one or two groups selected from OH, cyclopropyl, oxetanyl and morpholino; (b) $C_3$-$C_6$ cycloalkyl; (c) a 4 to 6 membered heterocyclyl containing one to three heteroatoms selected from N, O and S, optionally substituted with halogen or methyl; and (d) a 5 to 6 membered heteroaryl containing one to four heteroatoms selected from N, O and S, optionally substituted with one to three groups selected from methyl and cyclopropyl. In certain embodiments, $R^1$ is selected from (a) $C_1$-$C_5$ alkyl optionally substituted with one or two groups selected from OH, cyclopropyl, oxetanyl and morpholino; (b) $C_3$-$C_4$ cycloalkyl; (c) a 4 to 6 membered heterocyclyl containing one O heteroatom optionally substituted with halogen or methyl; and (d) a 5 membered heteroaryl containing two to four heteroatoms selected from N and S substituted with one to three groups selected from methyl and cyclopropyl.

In certain embodiments, $R^1$ is selected from isopropyl, 1-hydroxy-2,2-dimethylpropan-3-yl, 2-hydroxy-2-methyl-propan-1-yl, 1-hydroxypropan-2-yl, 1,2-dihydroxypropan-3-yl, cyclopropylmethyl, oxetan-3-ylmethyl, 2-methyl-1-morpholinopropan-2-yl, cyclopropyl, cyclobutyl, oxetan-3-yl, 3-methyloxetan-3-yl, tetrahydro-2H-pyran-4-yl, 3-fluorotetrahydro-2H-pyran-4-yl, (3S,4R)-3-fluorotetrahydro-2H-pyran-4-yl, (3S,4S)-3-fluorotetrahydro-2H-pyran-4-yl, 1-methyl-1H-pyrazol-4-yl, 1,3-dimethyl-1H-pyrazol-4-yl, 1,3,5-trimethyl-1H-pyrazol-4-yl, 1-methyl-1H-pyrazol-5-yl, 3-cyclopropyl-1-methyl-1H-pyrazol-5-yl, 2-methyl-2H-1,2,3-triazol-4-yl, 1-methyl-1H-tetrazol-5-yl, 2-methyl-2H-tetrazol-5-yl and 5-methyl-1,3,4-thiadiazol-2-yl.

In certain embodiments, $R^2$ is selected from (a) $C_1$-$C_{10}$ alkyl optionally substituted with one to four $R^f$ groups; (b) $C_3$-$C_6$ cycloalkyl optionally substituted with halogen, $C_1$-$C_3$ alkyl and $C_1$-$C_3$ alkoxy; (c) a 4 to 6 membered heterocyclyl containing one to three heteroatoms selected from N, O and S, wherein the heterocyclyl may be optionally substituted with one to four $R^g$ groups; (d) phenyl optionally substituted with one to four groups selected from halogen, $C_1$-$C_3$ alkyl and $C_1$-$C_3$ alkoxy; (e) a 5 to 6 membered heteroaryl containing one to four heteroatoms selected from N, O and S, wherein the heteroaryl may be optionally substituted with one to four groups selected from halogen, $C_1$-$C_3$ alkyl, $C_1$-$C_3$ alkoxy and a 5 to 6 membered heteroaryl containing one to four heteroatoms selected from N, O and S; (f) $C_8$-$C_{10}$ bicyclic cycloalkyl optionally substituted with halogen, $C_1$-$C_3$ alkyl and $C_1$-$C_3$ alkoxy; and (g) a 9 to 10 membered bicyclic heterocyclyl containing one to three heteroatoms selected from N, O and S, wherein the heterocyclyl may be optionally substituted with halogen, $C_1$-$C_3$ alkyl and $C_1$-$C_3$ alkoxy.

In certain embodiments, $R^2$ is selected from (a) $C_1$-$C_6$ alkyl optionally substituted with one or two $R^f$ groups; (b) $C_3$-$C_6$ cycloalkyl optionally substituted with one or two halogens; (c) a 4 to 6 membered heterocyclyl containing one to three heteroatoms selected from N, O and S, wherein the heterocyclyl may be optionally substituted with one to three $R^g$ groups; (d) a 5 to 6 membered heteroaryl containing one to four heteroatoms selected from N, O and S, wherein the heteroaryl may be optionally substituted with one or two groups selected from $C_1$-$C_3$ alkyl and a 5 to 6 membered heteroaryl containing one to four heteroatoms selected from N, O and S; and (e) $C_8$-$C_{10}$ bicyclic cycloalkyl optionally substituted with halogen.

In certain embodiments, $R^2$ is selected from (a) $C_1$-$C_6$ alkyl optionally substituted with one or two $R^f$ groups; (b) $C_3$-$C_6$ cycloalkyl optionally substituted with one or two halogens; (c) a 4 to 6 membered heterocyclyl containing one N heteroatom, wherein the heterocyclyl may be optionally substituted with one to three $R^g$ groups; (d) a 5 to 6 membered heteroaryl containing two N heteroatoms, wherein the heteroaryl may be optionally substituted with one or two groups selected from methyl and a 5 to 6 membered heteroaryl containing one N heteroatom; and (e) $C_8$-$C_{10}$ bicyclic cycloalkyl optionally substituted with halogen.

In certain embodiments, each $R^f$ is selected from (a) halogen; (b) hydroxy; (c) $C_1$-$C_3$ alkoxy; (d) $NR^kR^m$; (e) $C_3$-$C_6$ cylcoalkyl optionally substituted with one or more $R^h$ groups; (f) a 4 to 6 membered heterocyclyl containing one to three heteroatoms selected from N, O and S, wherein the heterocyclyl may be optionally substituted with one or more groups selected from halogen, $C_1$-$C_3$ alkoxy, $C_1$-$C_3$ alkyl optionally substituted with halogen, —C(=O)O($C_1$-$C_6$ alkyl) and phenyl; (g) phenyl optionally substituted with one or more $R^j$ groups; and (h) a 5 to 6 membered heteroaryl containing one to four heteroatoms selected from N, O and S, wherein the heteroaryl may be optionally substituted with one or more $R^j$ groups.

In certain embodiments, each $R^f$ is selected from (a) halogen; (b) hydroxy; (c) $C_1$-$C_3$ alkoxy; (d) $NR^kR^m$; (e) $C_3$-$C_6$ cylcoalkyl optionally substituted with one or two $R^h$ groups; (f) a 4 to 6 membered heterocyclyl containing one to three heteroatoms selected from N, O and S, wherein the heterocyclyl may be optionally substituted with one group selected from $C_1$-$C_3$ alkyl optionally substituted with halogen, —C(=O)O($C_1$-$C_6$ alkyl) and phenyl; (g) phenyl optionally substituted with one or two $R^j$ groups; and (h) a 5 to 6 membered heteroaryl containing one to four heteroatoms selected from N, O and S, wherein the heteroaryl may be optionally substituted with one or two $R^j$ groups.

In certain embodiments, each $R^f$ is selected from (a) halogen; (b) hydroxy; (c) $C_1$-$C_3$ alkoxy; (d) dimethylamino; (e) $C_3$-$C_5$ cylcoalkyl optionally substituted with one or two $R^h$ groups; (f) a 4 to 6 membered heterocyclyl containing one heteroatom selected from N and O, wherein the heterocyclyl may be optionally substituted with one group selected from $C_1$-$C_3$ alkyl optionally substituted with halogen, —C(=O)O($C_1$-$C_6$ alkyl) and phenyl; (g) phenyl substituted with one or two $R^j$ groups; and (h) a 5 to 6 membered heteroaryl containing one to three N heteroatoms, wherein the heteroaryl may be optionally substituted with one or two $R^j$ groups.

In certain embodiments, each $R^f$ is selected from F, hydroxy, methoxy, ethoxy, isopropoxy, dimethylamino, cyclopentyl, 4,4-difluorocyclohexyl, 3,3-difluorocyclobutyl, 1-(ethoxymethyl)cyclopropyl, 1-(4-(trifluoromethoxy)phenyl)cyclopropyl, 1-methylcyclobutyl, 1-methylazetidin-3-yl, oxetan-3-yl, azetidin-3-yl, 1-(tert-butoxycarbonyl)azetidin-3-yl, 1-(2,2,2-trifluoroethyl)azetidin-3-yl, 4-phenylpiperidin-4-yl, pyrrolidin-1-yl, tetrahydro-2H-pyran-2-yl, 2-chlorophenyl, 2-(trifluoromethyl)phenyl, 3-chlorophenyl, 3-fluorophenyl, 4-chlorophenyl, 4-fluorophenyl, 4-(difluoromethoxy)phenyl, 4-methoxyphenyl, 2,3-difluorophenyl, 2,4-difluorophenyl, 3-fluoro-4-methoxyphenyl, 3-chloro-4-fluorophenyl, 4-chloro-3-fluorophenyl, 1H-pyrazol-1-yl, 4-chloro-1H-pyrazol-1-yl, 4-methyl-1H-pyrazol-1-yl, 1-methyl-1H-pyrazol-3-yl, 1-methyl-1H-pyrazol-4-yl, 1-methyl-1H-pyrazol-5-yl, 1-methyl-1H-imidazol-2-yl, 1-methyl-1H-1,2,3-triazol-5-yl, 3-methoxypyridin-2-yl, 3,5-difluoropyridin-2-yl, 6-(trifluoromethyl)pyridin-2-yl, 6-methylpyridin-2-yl, 2-methylpyridin-3-yl, 2-methoxypyridin-3-yl, 2-chloropyridin-3-yl and 6-methylpyridin-3-yl.

In certain embodiments, each $R^k$ and $R^m$ are independently selected from hydrogen and $C_1$-$C_3$ alkyl. In certain embodiments, each $R^k$ and $R^m$ are independently $C_1$-$C_3$ alkyl. In certain embodiments, each $R^k$ and $R^m$ are methyl.

In certain embodiments, each $R^h$ is selected from halogen, $C_1$-$C_3$ alkyl, $C_1$-$C_3$ alkoxy and phenyl optionally substituted with $C_1$-$C_3$ alkoxy, wherein the alkyl, alkoxys and phenyl may be optionally substituted with halogen. In certain embodiments, each $R^h$ is selected from halogen, $C_1$-$C_3$ alkyl, $C_1$-$C_3$ alkoxy and phenyl optionally substituted with $C_1$-$C_3$ alkoxy optionally substituted with halogen. In certain embodiments, each $R^h$ is selected from F, methyl, ethoxymethyl and 4-(trifluoromethoxy)phenyl.

In certain embodiments, each $R^j$ is selected from halogen, $C_1$-$C_3$ alkyl and $C_1$-$C_3$ alkoxy, wherein the alkyl and alkoxy may be optionally substituted with halogen. In certain embodiments, each $R^j$ is selected from halogen, methyl, trifluoromethyl, methoxy and difluoromethoxy. In certain embodiments, each $R^j$ is selected from halogen, trifluoromethyl, methoxy and difluoromethoxy. In certain embodiments, each $R^j$ is selected from halogen, methyl, trifluoromethyl and methoxy.

In certain embodiments, each $R^g$ is selected from (a) halogen; (b) $C_1$-$C_3$ alkyl optionally substituted with halogen, $C_1$-$C_3$ alkoxy, or phenyl optionally substituted with two groups selected from halogen and $C_1$-$C_3$ alkoxy; (c) $C_1$-$C_3$ alkoxy optionally substituted with halogen; (d) phenyl optionally substituted with halogen or $C_1$-$C_3$ alkoxy; and (e) a 5 to 6 membered heteroaryl containing one to four heteroatoms selected from N, O and S, wherein the heteroaryl may be optionally substituted with one or two groups selected from halogen and $C_1$-$C_3$ alkoxy. In certain embodiments, each $R^g$ is selected from (a) halogen; (b) $C_1$-$C_3$ alkyl optionally substituted with phenyl optionally substituted with two groups selected from halogen and $C_1$-$C_3$ alkoxy; (c) $C_1$-$C_3$ alkoxy; (d) phenyl optionally substituted with halogen; and (e) a 5 to 6 membered heteroaryl containing one N heteroatom optionally substituted with one or two groups selected from halogen and $C_1$-$C_3$ alkoxy. In certain embodiments, each $R^g$ is selected from F, methyl, ethyl, isopropyl, 2-fluoro-6-methoxybenzyl, 2-methoxyethyl, 3-fluorophenyl, 4-fluorophenyl, 2,4-difluorophenyl, 3,4-difluorophenyl, 3,5-difluorophenyl and 5-fluoro-2-methoxypyridin-3-yl.

In certain embodiments, $R^2$ is selected from 2-methylbutyl, 2-ethylbutyl, isobutyl, 2,2-difluoropropyl, 2,2-difluoroethyl, 3-fluoropropyl, 3-hydroxybutyl, 2-methoxypropyl, 3-methoxypropyl, 3-ethoxypropyl, 2-methoxy-2-methylpropyl, 3-methoxy-2,2-dimethylpropyl, 2-hydroxy-2-methylpropyl, 3-isopropoxypropyl, cyclopentylmethyl, (3,3-difluorocyclobutyl)methyl, (1-(ethoxymethyl)cyclopropyl)methyl, (1-(4-(trifluoromethoxy)phenyl)cyclopropyl)methyl, (1-methylcyclobutyl)methyl, (1-methylazetidin-3-yl)methyl, oxetan-3-ylmethyl, azetidin-3-ylmethyl, (1-(tert-butoxycarbonyl)azetidin-3-yl)methyl, (1-(2,2,2-trifluoroethyl)azetidin-3-yl)methyl, (4-phenylpiperidin-4-yl)methyl, (tetrahydro-2H-pyran-2-yl)methyl, 2,3-difluorobenzyl, 3-fluoro-4-methoxybenzyl, 4-(difluoromethoxy)benzyl, 4-chlorobenzyl, 4-methoxybenzyl, 3-fluorobenzyl, 4-chloro-3-fluorobenzyl, 4-fluorobenzyl, 3-chlorobenzyl, 3-chloro-4-fluorobenzyl, 2-(trifluoromethyl)benzyl, 2,4-difluorobenzyl, 4-chlorophenethyl, 2-chlorophenethyl, 3-chlorophenethyl, 1-(4-chloro-3-fluorophenyl)-2-(dimethylamino)ethyl, 1-(4-chloro-3-fluorophenyl)-2-(pyrrolidin-1-yl)ethyl, 2-hydroxy-1-(4-chloro-3-fluorophenyl)ethyl, (S)-2-hydroxy-1-(4-chloro-3-fluorophenyl)ethyl, (R)-2-hydroxy-1-(4-chloro-3-fluorophenyl)ethyl, 2-hydroxy-1-(3-fluoro-4-methoxyphenyl)ethyl, (S)-2-hydroxy-1-(3-fluoro-4-methoxyphenyl)ethyl, 2-(4-chloro-1H-pyrazol-1-yl)ethyl, (1-methyl-1H-pyrazol-3-yl)methyl, (1-methyl-1H-pyrazol-5-yl)methyl, (6-(trifluoromethyl)pyridin-2-yl)methyl, (2-methylpyridin-3-yl)methyl, (2-methoxypyridin-3-yl)methyl, (6-methylpyridin-3-yl)methyl, (6-methylpyridin-2-yl)methyl, (2-chloropyridin-3-yl)methyl, (3-methoxypyridin-2-yl)methyl, (3,5-difluoropyridin-2-yl)methyl, 2-(4-methyl-1H-pyrazol-1-yl)ethyl, 2-(1H-pyrazol-1-yl)ethyl, (3-fluoro-4-methoxyphenyl)(1-methyl-1H-pyrazol-4-yl)methyl, (3-fluoro-4-methoxyphenyl)(1-methyl-1H-1,2,3-triazol-5-yl)methyl, (3-fluoro-4-methoxyphenyl)(1-methyl-1H-imidazol-2-yl)methyl, 4,4-difluorocyclohexyl, piperidin-4-yl, 1-methylazetidin-3-yl, 1-(2-fluoro-6-methoxybenzyl)azetidin-3-yl, 4-(3-fluorophenyl)piperidin-3-yl, 4-(4-fluorophenyl)piperidin-3-yl, 4-(2,4-difluorophenyl)-1-methylpyrrolidin-3-yl, (3S,4R)-4-(2,4-difluorophenyl)-1-methylpyrrolidin-3-yl, 4-(3,4-difluorophenyl)-1-methylpyrrolidin-3-yl, (3S,4R)-4-(3,4-difluorophenyl)-1-methylpyrrolidin-3-yl, 4-(3,5-difluorophenyl)-1-methylpyrrolidin-3-yl, (3S,4R)-4-(3,5-difluorophenyl)-1-methylpyrrolidin-3-yl, 4-(3,4-difluorophenyl)-1-ethylpyrrolidin-3-yl, (3S,4R)-4-(3,4-difluorophenyl)-1-ethylpyrrolidin-3-yl, 4-(3,4-difluorophenyl)pyrrolidin-3-yl, (3S,4R)-4-(3,4-difluorophenyl)pyrrolidin-3-yl, 5,5-difluoropiperidin-3-yl, 4-(3,5-difluorophenyl)-1-isopropylpyrrolidin-3-yl, (3S,4R)-4-(3,5-difluorophenyl)-1-isopropylpyrrolidin-3-yl, 1-(5-fluoro-2-methoxypyridin-3-yl)pyrrolidin-3-yl, 4-(4-fluorophenyl)-1-(2-methoxyethyl)pyrrolidin-3-yl, (3R,4S)-4-(4-fluorophenyl)-1-(2-methoxyethyl)pyrrolidin-3-yl, (3S,4R)-4-(4-fluorophenyl)-1-(2-methoxyethyl)pyrrolidin-3-yl, 1-(2-fluoro-6-methoxybenzyl)piperidin-3-yl, (R)-1-(2-fluoro-6-methoxybenzyl)piperidin-3-yl, 1-(5,5-difluoro-1-(2-fluoro-6-methoxybenzyl)piperidin-3-yl, (R)-1-(5,5-difluoro-1-(2-fluoro-6-methoxybenzyl)piperidin-3-yl, 3-methyl-1-(pyridin-2-yl)-1H-pyrazol-5-yl and 5-chloro-2,3-dihydro-1H-inden-1-yl.

In certain embodiments, $R^2$ is $C_1$-$C_{10}$ alkyl optionally substituted with one to four $R^f$ groups. In certain embodiments, $R^2$ is $C_1$-$C_6$ alkyl optionally substituted with one to four $R^f$ groups. In certain embodiments, $R^2$ is $C_1$-$C_{10}$ alkyl optionally substituted with one or two $R^f$ groups. In certain embodiments, $R^2$ is $C_1$-$C_6$ alkyl optionally substituted with one or two $R^f$ groups. In certain embodiments, $R^2$ is $C_1$-$C_6$ alkyl.

In certain embodiments, $R^2$ is —$CH_2R^f$ (such compounds have the structure of Formula X).

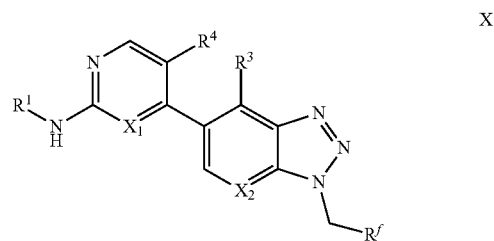

In certain embodiments, $R^3$ is selected from hydrogen and halogen. In certain embodiments, $R^3$ is hydrogen. In certain embodiments, $R^3$ is halogen. In certain embodiments, $R^3$ is selected from hydrogen, fluorine and chlorine. In certain embodiments, $R^3$ is selected from hydrogen and fluorine. In certain embodiments, $R^3$ is fluorine.

In certain embodiments, $R^4$ is selected from hydrogen and halogen. In certain embodiments, $R^4$ is hydrogen. In certain embodiments, $R^4$ is halogen. In certain embodiments, $R^4$ is selected from hydrogen, fluorine and chlorine. In certain embodiments, $R^4$ is selected from hydrogen and fluorine. In certain embodiments, $R^4$ is fluorine.

In certain embodiments, $R^3$ and $R^4$ are selected from hydrogen and halogen. In certain embodiments, $R^3$ and $R^4$ are selected from hydrogen, fluorine and chlorine. In certain embodiments, $R^3$ and $R^4$ are selected from hydrogen and fluorine. In certain embodiments, $R^3$ and $R^4$ are hydrogen. In certain embodiments, $R^3$ is hydrogen; and $R^4$ is selected from hydrogen and halogen. In certain embodiments, $R^3$ is hydrogen; and $R^4$ is selected from hydrogen, fluorine and chlorine. In certain embodiments, $R^3$ is hydrogen; and $R^4$ is selected from hydrogen and fluorine. In certain embodiments, $R^3$ is selected from hydrogen and halogen; and $R^4$ is hydrogen. In certain embodiments, $R^3$ is selected from hydrogen, fluorine and chlorine; and $R^4$ is hydrogen. In certain embodiments, $R^3$ is selected from hydrogen and fluorine; and $R^4$ is hydrogen. In certain embodiments, $R^3$ is hydrogen and $R^4$ is selected from hydrogen and halogen, or $R^3$ is selected from hydrogen and halogen and $R^4$ is hydrogen. In certain embodiments, $R^3$ is hydrogen and $R^4$ is selected from hydrogen, fluorine and chlorine, or $R^3$ is selected from hydrogen, fluorine and chlorine and $R^4$ is hydrogen. In certain embodiments, $R^3$ is hydrogen and $R^4$ is selected from hydrogen and fluorine, or $R^3$ is selected from hydrogen and fluorine and $R^4$ is hydrogen.

In certain embodiments, a compound of Examples 1 to 126 is provided.

In certain embodiments, a compound of Formula I, II, III, IV, V, VI, VII, VIII, IX or X is provided.

It will be appreciated that certain compounds described herein may contain asymmetric or chiral centers, and therefore exist in different stereoisomeric forms. It is intended that all stereoisomeric forms of the compounds described herein, including but not limited to, diastereomers, enantiomers and atropisomers, as well as mixtures thereof such as racemic mixtures, form part of the present compounds.

In the structures shown herein, where the stereochemistry of any particular chiral atom is not specified, then all stereoisomers are contemplated and included as the compounds described herein. Where stereochemistry is specified by a solid wedge or dashed line representing a particular configuration, then that stereoisomer is so specified and defined.

It will also be appreciated that certain compounds of Formula I, II, III, IV, V, VI, VII, VIII, IX or X may be used as intermediates for further compounds of Formula I, II, III, IV, V, VI, VII, VII, IX or X.

It will be further appreciated that the compounds described herein may exist in unsolvated as well as solvated forms with pharmaceutically acceptable solvents such as water, ethanol, and the like, and it is intended that the compounds embrace both solvated and unsolvated forms.

Synthesis of Compounds

Compounds described herein may be synthesized by synthetic routes that include processes analogous to those well-known in the chemical arts, particularly in light of the description contained herein. The starting materials are generally available from commercial sources such as Sigma-Aldrich (St. Louis, Mo.), Alfa Aesar (Ward Hill, Mass.), or TCI (Portland, Oreg.), or are readily prepared using methods well known to those skilled in the art (e.g., prepared by methods generally described in Louis F. Fieser and Mary Fieser, *Reagents for Organic Synthesis*. v. 1-23, New York: Wiley 1967-2006 ed. (also available via the Wiley InterScience® website), or *Beilsteins Handbuch der organischen Chemie*, 4, Aufl. ed. Springer-Verlag, Berlin, including supplements (also available via the Beilstein online database)).

For illustrative purposes, Schemes 1-3 show general methods for preparing the compounds described herein, as well as key intermediates. For a more detailed description of the individual reaction steps, see the Examples section below. Those skilled in the art will appreciate that other synthetic routes may be used to synthesize the compounds. Although specific starting materials and reagents are depicted in the Schemes and discussed below, other starting materials and reagents can be easily substituted to provide a variety of derivatives and/or reaction conditions. In addition, many of the compounds prepared by the methods described below can be further modified in light of this disclosure using conventional chemistry well known to those skilled in the art.

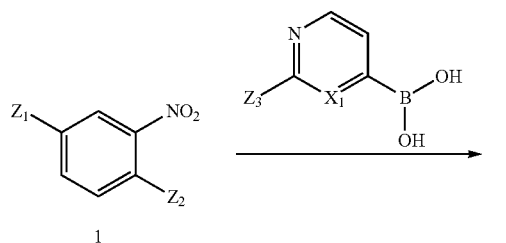

Scheme 1

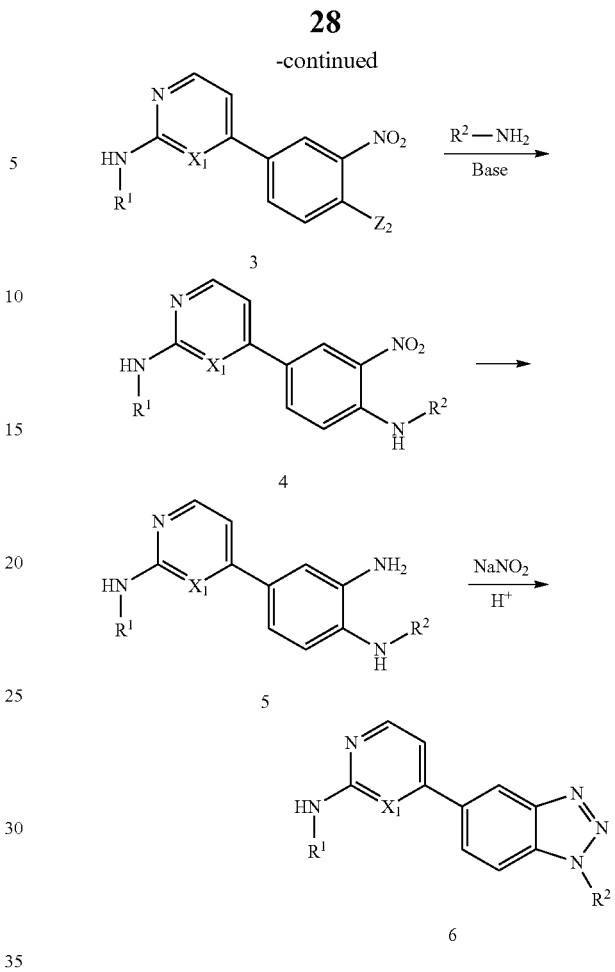

Scheme 1 shows a general scheme for the synthesis of compound 6, wherein $X_1$, $R^1$ and $R^2$ are as defined herein. The compound 2, wherein $Z_2$ is Cl or F and $Z_3$ is Cl or Br, may be prepared starting from compound 1, wherein $Z_1$ is Cl, Br or I, such as 4-chloro-1-fluoro-2-nitrobenzene. Palladium mediated coupling reaction, such as a Suzuki reaction, of compound 1 with a hetero aromatic boronic ester or boronic acid will furnish compound 2. Then compound 2 may be reacted with an appropriate amine under Buchwald reaction conditions to provide compound 3. Compound 3 may be subjected to a SnAr reaction with an amine in the presence of a base, such as $Cs_2CO_3$, $K_2CO_3$, NaH, in a polar solvent, such as DMF, DMSO, THF, etc., to provide compound 4. The reaction of compound 4 with a reducing agent, such as Zn:$NH_4Cl$, Pd:$H_2$, $SnCl_2$, will provide the diamine derivative 5, which may be treated with $NaNO_2$ in the presence of an acid, such as acetic acid, HCl, etc., to furnish the benzotrialoze analogs 6.

Scheme 2

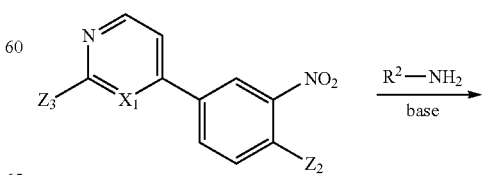

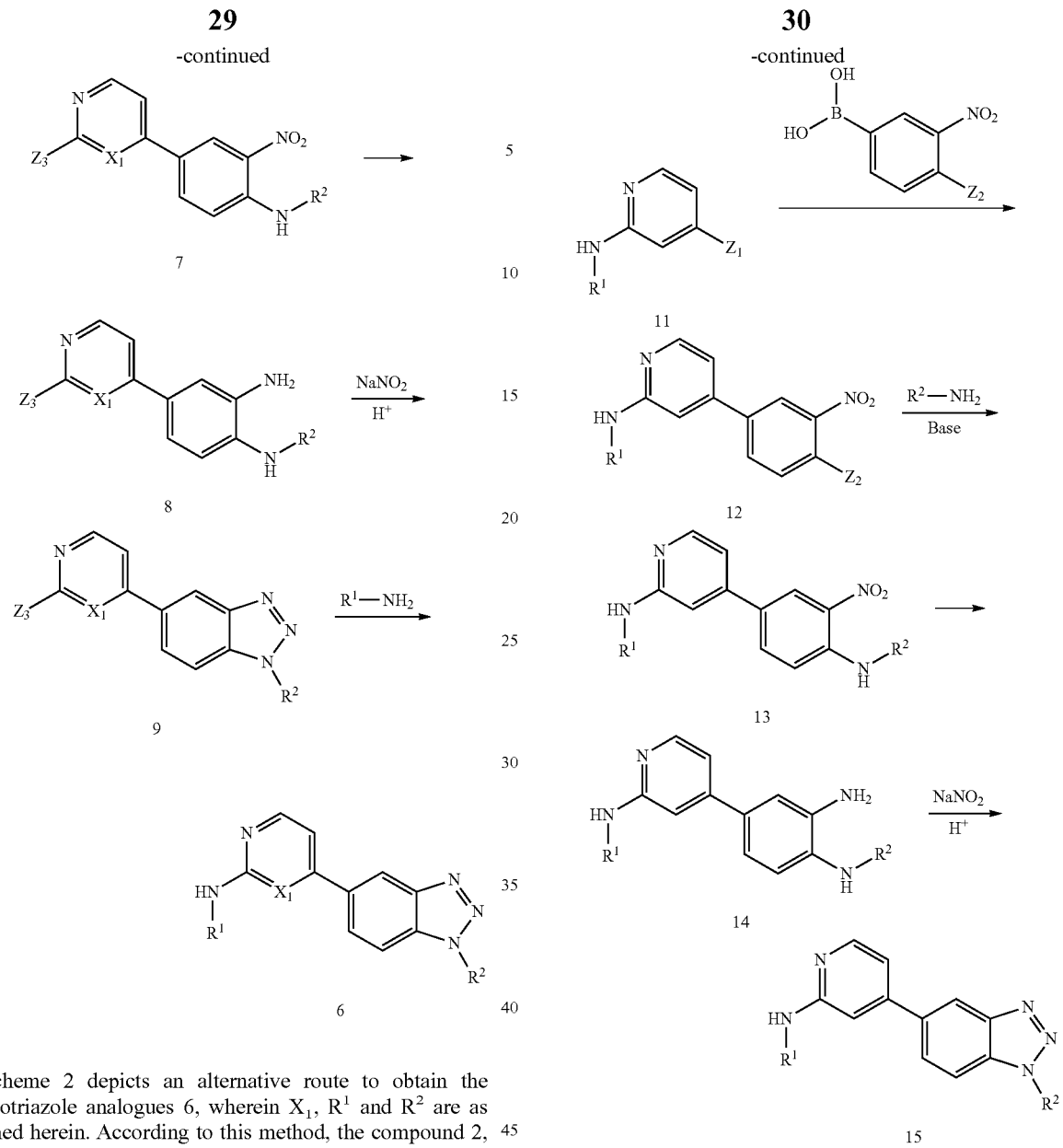

Scheme 2 depicts an alternative route to obtain the benzotriazole analogues 6, wherein $X_1$, $R^1$ and $R^2$ are as defined herein. According to this method, the compound 2, wherein $Z_2$ is as defined above, may be subjected to SnAr reaction with a suitable amine in the presence of a base to yield compound 7, wherein $Z_3$ is as defined above. Reduction of the nitro group in compound 7 may be carried out according to the methods described for the synthesis of compound 5 in Scheme 1. The resulting diamine compound 8 may be converted to the benzotriazole 9 according to the methods described for preparation of compound 6 in Scheme 1. Buchwald type coupling of compound 9 with an amine, such as alkyl amines, heteroaryl amines, cyclic alkyl amines, etc., provide the final benzotriazole analoges 6.

Scheme 3

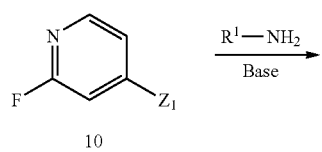

Scheme 3 shows a general scheme for the synthesis of benzotriazole analoges 15, wherein $R^1$ and $R^2$ are as defined herein. According to this method, a 2,4-dihalo substituted pyridine analogue 10, wherein $Z_1$ is as defined above, may be subjected to SnAr reaction with an amine in the presence of a base, such as $K_2CO_3$, $Cs_2CO$, NaH, etc., to provide compound 11. Compound 11 may be subjected to a Pd mediated coupling reaction, such as a Suzuki reaction, as described for the synthesis of compound 2 in Scheme 1 to provide compound 12, wherein $Z_2$ is as defined above. Then compound 12 may be subjected a second SnAr reaction with an amine in the presence of a base to give compound 13. The reduction of the nitro group of compound 13 with a reducing agent, such as $Zn:NH_4Cl$, $SnCl_2$, etc., followed by treatment of $NaNO_2$ in the presence of an acid, such as HCl, acetic acid, etc., will provide the benzotriazole analogs 15.

In preparing compounds of Formula I, protection of remote functionalities (e.g., primary or secondary amines, etc.) of intermediates may be necessary. The need for such protection will vary depending on the nature of the remote functionality and the conditions of the preparation methods. Suitable amino-protecting groups (NH-Pg) include acetyl, trifluoroacetyl, t-butyloxycarbonyl ("Boc"), benzyloxycarbonyl ("CBz") and 9-fluorenylmethyleneoxycarbonyl ("Fmoc"). The need for such protection is readily determined by one skilled in the art. For a general description of protecting groups and their use, see T. W. Greene, et al. *Greene's Protective Groups in Organic Synthesis*. New York: Wiley Interscience, 2006.

Methods of Separation

It may be advantageous to separate reaction products from one another and/or from starting materials. The desired products of each step or series of steps is separated and/or purified (hereinafter separated) to the desired degree of homogeneity by the techniques common in the art. Typically such separations involve multiphase extraction, crystallization from a solvent or solvent mixture, distillation, sublimation, or chromatography. Chromatography can involve any number of methods including, for example: reverse-phase and normal phase; size exclusion; ion exchange; high, medium and low pressure liquid chromatography methods and apparatus; small scale analytical; simulated moving bed (SMB) and preparative thin or thick layer chromatography, as well as techniques of small scale thin layer and flash chromatography. One skilled in the art will apply techniques most likely to achieve the desired separation.

Diastereomeric mixtures can be separated into their individual diastereomers on the basis of their physical chemical differences by methods well known to those skilled in the art, such as by chromatography and/or fractional crystallization. Enantiomers can be separated by converting the enantiomeric mixture into a diastereomeric mixture by reaction with an appropriate optically active compound (e.g., chiral auxiliary such as a chiral alcohol or Mosher's acid chloride), separating the diastereomers and converting (e.g., hydrolyzing) the individual diastereoisomers to the corresponding pure enantiomers. Enantiomers can also be separated by use of a chiral HPLC column.

A single stereoisomer, e.g., an enantiomer, substantially free of its stereoisomer may be obtained by resolution of the racemic mixture using a method such as formation of diastereomers using optically active resolving agents (Eliel, E. and Wilen, S. *Stereochemistry of Organic Compounds*. New York: John Wiley & Sons, Inc., 1994; Lochmuller, C. H., et al. "Chromatographic resolution of enantiomers: Selective review." *J. Chromatogr.* 113(3) (1975): pp. 283-302). Racemic mixtures of chiral compounds described herein may be separated and isolated by any suitable method, including: (1) formation of ionic, diastereomeric salts with chiral compounds and separation by fractional crystallization or other methods, (2) formation of diastereomeric compounds with chiral derivatizing reagents, separation of the diastereomers, and conversion to the pure stereoisomers, and (3) separation of the substantially pure or enriched stereoisomers directly under chiral conditions. See: Wainer, Irving W., Ed. *Drug Stereochemistry: Analytical Methods and Pharmacology*. New York: Marcel Dekker, Inc., 1993.

Under method (1), diastereomeric salts can be formed by reaction of enantiomerically pure chiral bases such as brucine, quinine, ephedrine, strychnine, α-methyl-β-phenylethylamine (amphetamine), and the like with asymmetric compounds bearing acidic functionality, such as carboxylic acid and sulfonic acid. The diastereomeric salts may be induced to separate by fractional crystallization or ionic chromatography. For separation of the optical isomers of amino compounds, addition of chiral carboxylic or sulfonic acids, such as camphorsulfonic acid, tartaric acid, mandelic acid, or lactic acid, can result in formation of the diastereomeric salts.

Alternatively, by method (2), the substrate to be resolved is reacted with one enantiomer of a chiral compound to form a diastereomeric pair (Eliel, E. and Wilen, S. *Stereochemistry of Organic Compounds*. New York: John Wiley & Sons, Inc., 1994, p. 322). Diastereomeric compounds can be formed by reacting asymmetric compounds with enantiomerically pure chiral derivatizing reagents, such as menthyl derivatives, followed by separation of the diastereomers and hydrolysis to yield the pure or enriched enantiomer. A method of determining optical purity involves making chiral esters, such as a menthyl ester, e.g., (−) menthyl chloroformate in the presence of base, or Mosher ester, α-methoxy-α-(trifluoromethyl)phenyl acetate (Jacob III, Peyton. "Resolution of (±)-5-Bromonornicotine. Synthesis of (R)- and (S)-Nornicotine of High Enantiomeric Purity." *J. Org. Chem.* Vol. 47, No. 21 (1982): pp. 4165-4167), of the racemic mixture, and analyzing the $^1$H NMR spectrum for the presence of the two atropisomeric enantiomers or diastereomers. Stable diastereomers of atropisomeric compounds can be separated and isolated by normal- and reverse-phase chromatography following methods for separation of atropisomeric naphthyl-isoquinolines (WO 96/15111).

By method (3), a racemic mixture of two enantiomers can be separated by chromatography using a chiral stationary phase (Lough, W. J., Ed. *Chiral Liquid Chromatography*. New York: Chapman and Hall, 1989; Okamoto, Yoshio, et al. "Optical resolution of dihydropyridine enantiomers by high-performance liquid chromatography using phenylcarbamates of polysaccharides as a chiral stationary phase." *J. of Chromatogr.* Vol. 513 (1990): pp. 375-378). Enriched or purified enantiomers can be distinguished by methods used to distinguish other chiral molecules with asymmetric carbon atoms, such as optical rotation and circular dichroism.

Biological Evaluation

Determination of the activity of ERK activity of a compound of Formula I, II, III, IV, V, VI, VII, VIII, IX or X is possible by a number of direct and indirect detection methods. Certain exemplary compounds described herein were assayed for their ERK inhibition assay (Biological Example 1). The range of ERK binding activities was less than 1 nM (nanomolar) to about 10 μM (micromolar). A cell-based function assay (Biological Example 2) was used to determine the effect of ERK inhibitors on down-stream signaling by assaying phosphorylation of P90RSK.

Administration and Pharmaceutical Formulations

The compounds described herein may be administered by any convenient route appropriate to the condition to be treated. Suitable routes include oral, parenteral (including subcutaneous, intramuscular, intravenous, intraarterial, intradermal, intrathecal and epidural), transdermal, rectal, nasal, topical (including buccal and sublingual), vaginal, intraperitoneal, intrapulmonary and intranasal.

The compounds may be administered in any convenient administrative form, e.g., tablets, powders, capsules, solutions, dispersions, suspensions, syrups, sprays, suppositories, gels, emulsions, patches, etc. Such compositions may contain components conventional in pharmaceutical preparations, e.g., diluents, carriers, pH modifiers, sweeteners, bulking agents, and further active agents. If parenteral administration is desired, the compositions will be sterile and in a solution or suspension form suitable for injection or infusion.

A typical formulation is prepared by mixing a compound described herein and a carrier or excipient. Suitable carriers and excipients are well known to those skilled in the art and are described in detail in, e.g., Ansel, Howard C., et al., *Ansel's Pharmaceutical Dosage Forms and Drug Delivery Systems*. Philadelphia: Lippincott, Williams & Wilkins, 2004; Gennaro, Alfonso R., et al. *Remington: The Science and Practice of Pharmacy*. Philadelphia: Lippincott, Williams & Wilkins, 2000; and Rowe, Raymond C. *Handbook of Pharmaceutical Excipients*. Chicago, Pharmaceutical Press, 2005. The formulations may also include one or more buffers, stabilizing agents, surfactants, wetting agents, lubricating agents, emulsifiers, suspending agents, preservatives, antioxidants, opaquing agents, glidants, processing aids, colorants, sweeteners, perfuming agents, flavoring agents, diluents and other known additives to provide an elegant presentation of the drug (i.e., a compound described herein or pharmaceutical composition thereof) or aid in the manufacturing of the pharmaceutical product (i.e., medicament).

One embodiment includes a pharmaceutical composition comprising a compound of Formula I, II, III, IV, V, VI, VII, VIII, IX or X or a stereoisomer or pharmaceutically acceptable salt thereof. A further embodiment provides a pharmaceutical composition comprising a compound of Formula I, II, III, IV, V, VI, VII, VIII, IX or X or a stereoisomer or pharmaceutically acceptable salt thereof, together with a pharmaceutically acceptable carrier or excipient.

Methods of Treatment with Compounds of the Invention

Also provided are methods of treating or preventing disease or condition by administering one or more compounds described herein, or a stereoisomer or pharmaceutically acceptable salt thereof. In one embodiment, a method of treating a hyperproliferative disease in a mammal comprising administering a therapeutically effective amount of the compound of Formula I, II, III, IV, V, VI, VII, VIII, IX or X, or a stereoisomer, tautomer or pharmaceutically acceptable salt thereof, to the mammal is provided.

Another embodiment provides a method of treating or preventing cancer in a mammal in need of such treatment, wherein the method comprises administering to said mammal a therapeutically effective amount of a compound of Formula I, II, III, IV, V, VI, VII, VIII, IX or X, or a stereoisomer, tautomer or pharmaceutically acceptable salt thereof.

Another embodiment provides a method of treating or preventing pain in a mammal in need of such treatment, wherein the method comprises administering to said mammal a therapeutically effective amount of a compound of Formula I, II, III, IV, V, VI, VII, VIII, IX or X, or a stereoisomer, tautomer or pharmaceutically acceptable salt thereof.

Another embodiment provides a method of treating or preventing an inflammatory disorder in a mammal in need of such treatment, wherein the method comprises administering to said mammal a therapeutically effective amount of a compound of Formula I, II, III, IV, V, VI, VII, VIII, IX or X, or a stereoisomer, tautomer or pharmaceutically acceptable salt thereof.

Another embodiment provides a method of inhibiting ERK protein kinase activity in a cell comprising treating the cell with a compound according to Formula I, II, III, IV, V, VI, VII, VIII, IX or X, or a stereoisomer, tautomer or pharmaceutically acceptable salt thereof.

Another embodiment provides a method of inhibiting ERK protein kinase activity in a cell comprising treating the cell with a compound according to Formula I, II, III, IV, V, VI, VII, VIII, IX or X, or a stereoisomer, tautomer or pharmaceutically acceptable salt thereof, in an amount effective to attenuate or eliminate ERK kinase activity.

Another embodiment provides a method of inhibiting ERK protein kinase activity in a patient in need thereof comprising the step of administering to said patient a compound according to Formula I, II, III, IV, V, VI, VII, VIII, IX or X, or a stereoisomer, tautomer or pharmaceutically acceptable salt thereof.

Another embodiment provides a method of treating or ameliorating the severity of a hyperproliferative disorder in a patient in need thereof comprising administering to said patient a compound according to Formula I, II, III, IV, V, VI, VII, VIII, IX or X, or a stereoisomer, tautomer or pharmaceutically acceptable salt thereof.

Another embodiment provides a method of treating or ameliorating the severity of a hyperproliferative disorder in a patient in need thereof comprising co-administering to said patient a compound according to Formula I, II, III, IV, V, VI, VII, VIII, IX or X, or a stereoisomer, tautomer or pharmaceutically acceptable salt thereof, with at least one other chemotherapeutic agent used to treat or ameliorate the hyperproliferative disorder.

Another embodiment provides a method of treating or ameliorating the severity of pain in a patient in need thereof comprising administering to said patient a compound according to Formula I, II, III, IV, V, VI, VII, VIII, IX or X, or a stereoisomer, tautomer or pharmaceutically acceptable salt thereof.

Another embodiment provides a method of treating or ameliorating the severity of an inflammatory disorder in a patient in need thereof comprising administering to said patient a compound according to Formula I, II, III, IV, V, VI, VII, VIII, IX or X, or a stereoisomer, tautomer or pharmaceutically acceptable salt thereof.

In another embodiment, a method of treating or preventing a disease or disorder modulated by ERK, comprising administering to a mammal in need of such treatment an effective amount of a compound of Formula I, II, III, IV, V, VI, VII, VIII, IX or X, or a stereoisomer, tautomer or pharmaceutically acceptable salt thereof. Examples of such diseases and disorders include, but are not limited to, hyperproliferative diseases, such as cancer, and pain or inflammatory diseases.

Another embodiment provides the use of a compound of Formula I, II, III, IV, V, VI, VII, VIII, IX or X, or a stereoisomer, tautomer or pharmaceutically acceptable salt thereof, in the manufacture of a medicament for the treatment of a hyperproliferative disease. Another embodiment provides the use of a compound of Formula I, II, III, IV, V, VI, VII, VIII, IX or X, or a stereoisomer, tautomer or pharmaceutically acceptable salt thereof, in the manufacture of a medicament for the treatment of cancer.

Another embodiment provides the use of a compound of Formula I, II, III, IV, V, VI, VII, VIII, IX or X, or a stereoisomer, tautomer or pharmaceutically acceptable salt thereof, in the manufacture of a medicament for the treatment of pain.

Another embodiment provides the use of a compound of Formula I, II, III, IV, V, VI, VII, VIII, IX or X, or a stereoisomer, tautomer or pharmaceutically acceptable salt thereof, in the manufacture of a medicament for the treatment of an inflammatory disease.

Another embodiment provides the use of a compound of Formula I, II, III, IV, V, VI, VII, VIII, IX or X, or a stereoisomer, tautomer or pharmaceutically acceptable salt thereof, for use in the treatment of hyperproliferative diseases. Another embodiment provides the use of a compound of Formula I, II, III, IV, V, VI, VII, VIII, IX or X, or a stereoisomer, tautomer or pharmaceutically acceptable salt thereof, for use in the treatment of cancer.

Another embodiment provides the use of a compound of Formula I, II, III, IV, V, VI, VII, VIII, IX or X, or a stereoisomer, tautomer or pharmaceutically acceptable salt thereof, for use in the treatment of pain.

Another embodiment provides the use of a compound of Formula I, II, III, IV, V, VI, VII, VIII, IX or X, or a stereoisomer, tautomer or pharmaceutically acceptable salt thereof, for use in the treatment of inflammatory diseases.

In certain embodiments, the hyperproliferative disease is cancer. In certain embodiments, the cancer may be selected from breast, ovary, cervix, prostate, testis, genitourinary tract, esophagus, larynx, glioblastoma, neuroblastoma, stomach, skin, keratoacanthoma, lung, epidermoid carcinoma, large cell carcinoma, NSCLC, small cell carcinoma, lung adenocarcinoma, bone, colon, adenoma, pancreas, adenocarcinoma, thyroid, follicular carcinoma, undifferentiated carcinoma, papillary carcinoma, seminoma, melanoma, sarcoma, bladder carcinoma, liver carcinoma and biliary passages, kidney carcinoma, myeloid disorders, lymphoid disorders, hairy cells, buccal cavity and pharynx (oral), lip, tongue, mouth, pharynx, small intestine, colon-rectum, large intestine, rectum, brain and central nervous system, Hodgkin's and leukemia. In certain embodiments, the cancer disorder is melanoma. In certain embodiments, the cancer is pancreatic cancer. In certain embodiments, the cancer is thyroid cancer. In certain embodiments, the cancer is colorectal cancer. In certain embodiments, the cancer is lung cancer. In certain embodiments, the cancer is breast cancer. In certain embodiments, the cancer is ovarian cancer. In certain embodiments, the cancer is acute myelogenous leukemia. In certain embodiments, the cancer is chronic myelomonocytic leukemia. In certain embodiments, the cancer is chronic myelogenous leukemia. In certain embodiments, the cancer is multiple myeloma. In certain embodiments, the cancer is myeloid leukemia.

In certain embodiments, the inflammatory disorder may be selected from arthritis, low back pain, inflammatory bowel disease, and rheumatism.

Combination Therapy

The compounds described herein and stereoisomers, tautomers and pharmaceutically acceptable salts thereof may be employed alone or in combination with other therapeutic agents for treatment. The compounds described herein may be used in combination with one or more additional drugs, for example an anti-hyperproliferative (or anti-cancer) agent that works through action on a different target protein. The second compound of the pharmaceutical combination formulation or dosing regimen preferably has complementary activities to the compound described herein, such that they do not adversely affect each other. Such molecules are suitably present in combination in amounts that are effective for the purpose intended. The compounds may be administered together in a unitary pharmaceutical composition or separately and, when administered separately this may occur simultaneously or sequentially in any order. Such sequential administration may be close in time or remote in time.

EXAMPLES

For illustrative purposes, the following Examples are included. However, it is to be understood that these Examples do not limit the invention and are only meant to suggest a method of practicing the invention. Persons skilled in the art will recognize that the chemical reactions described may be readily adapted to prepare a number of other compounds described herein, and alternative methods for preparing the compounds are deemed to be within the scope of this invention. For example, the synthesis of non-exemplified compounds may be successfully performed by modifications apparent to those skilled in the art, e.g., by appropriately protecting interfering groups, by utilizing other suitable reagents known in the art other than those described, and/or by making routine modifications of reaction conditions. Alternatively, other reactions disclosed herein or known in the art will be recognized as having applicability for preparing other compounds described herein.

In the Examples described below, unless otherwise indicated all temperatures are set forth in degrees Celsius. Reagents were purchased from commercial suppliers such as Sigma-Aldrich, Alfa Aesar, or TCI, and were used without further purification unless otherwise indicated.

The reactions set forth below were done generally under a positive pressure of nitrogen or argon or with a drying tube (unless otherwise stated) in anhydrous solvents, and the reaction flasks were typically fitted with rubber septa for the introduction of substrates and reagents via syringe. Glassware was oven dried and/or heat dried.

Column chromatography was done on a Biotage system (Manufacturer: Dyax Corporation) having a silica gel column or on a silica SepPak cartridge (Waters) (unless otherwise stated). $^1$H NMR spectra were recorded on a Varian instrument operating at 400 MHz. $^1$H-NMR spectra were obtained as $CDCl_3$, $CD_3OD$, $D_2O$, $(CD_3)_2SO$, $(CD_3)_2CO$, $C_6D_6$, $CD_3CN$ solutions (reported in ppm), using tetramethylsilane (0.00 ppm) or residual solvent ($CDCl_3$: 7.26 ppm; $CD_3OD$: 3.31 ppm; $D_2O$: 4.79 ppm; $(CD_3)_2SO$: 2.50 ppm; $(CD_3)_2CO$: 2.05 ppm; $C_6D_6$: 7.16 ppm; $CD_3CN$: 1.94 ppm) as the reference standard. When peak multiplicities are reported, the following abbreviations are used: s (singlet), d (doublet), t (triplet), q (quartet), m (multiplet), br (broadened), dd (doublet of doublets), dt (doublet of triplets). Coupling constants, when given, are reported in Hertz (Hz).

Biological Example 1

ERK-2 Enzymatic Assay

Compounds were tested in an enzymatic assay using human ERK-2 (Mitogen Activated Kinase 1), recombinantly expressed as an n-terminal 6-His fusion protein in *E. coli* and corresponding to aa 8-360. The substrate used was the fluorescent Omnia peptide S/T17 (Invitrogen of Carlsbad, Calif.; Cat. KNZ1171C). Test compounds were diluted in dimethylsulfoxide ("DMSO") in 3-fold serial dilutions at 100× final concentrations. In addition to compound, the assay contained 50 mM HEPES [pH 7.3], 10 mM MgCl2, 1 mM DTT, 0.005% Triton-X100, 5 nM ERK-2 enzyme, 6.25 µM S/T17 peptide substrate and 25 µM ATP (corresponding to the observed $K_m$) for a total reaction volume of 25 µL. The assay was run at ambient temperature in a white 384-well polypropylene plate (Nunc, Inc of Naperville, Ill.; Cat. 267462) collecting data every 50 seconds for approximately 30 minutes on an Envision plate reader (PerkinElmer, Inc. of Waltham, Mass.); Excitation 340 nm/Emission 495 nm. The data collected from each well was fit to a straight line and the resulting rates were used to calculate percent of control. Percent of control was plotted against compound concentration and $IC_{50}$ values were determined using a four-parameter fit. Table 1 contains representative data for Examples disclosed herein. The reported $IC_{50}$ in Table 1 may be from a single assay or the mean of multiple assays. Examples 1-126 were tested in the above assay and were found to have an IC$_{50}$ of less than 1 µM. Examples 1-21, 23-34, 36-60, 62-80, 82-83, 86-126 were tested in the above assay and were found to have an IC$_{50}$ of less than 100 nM. Many of the Examples (100 out of 126) were tested in the above assay and were found to have an IC$_{50}$ of less than 10 nM.

Biological Example 2

Cellular P90RSK(Ser380) Phosphorylation Assay

Inhibition of PMA-stimulated P90RSK(Ser380) phosphorylation was determined by the following in vitro cellular mechanistic assay, which comprises incubating cells with a compound for 1.5 hours and quantifying fluorescent pP90RSK(Ser380) signal on fixed cells and normalizing to GAPDH signal.

HepG2 cells were obtained from ATCC and grown in DMEM supplemented with 10% fetal bovine serum. Cells were plated in 96-well plates at 35,000 cells/well and allowed to attach overnight at 37° C./5% CO$_2$. Diluted compounds were then added at a final concentration of 0.5% DMSO. After 1.5 hours compound incubation, cells were stimulated with the addition of phorbol 12-myristate 13-acetate ("PMA") at a final concentration of 100 ng/mL; the PMA stimulation was a 30-minute incubation at 37° C./5% CO$_2$. After the 30-minute PMA stimulation, cells were washed with phosphate buffered saline ("PBS") and fixed in 3.7% formaldehyde in PBS at room temperature for 15-20 minutes. This was followed by another wash in PBS and then permeabilization in 100% MeOH at room temperature for 10-15 minutes. Following the permeabilization incubation, cells were washed in PBS/0.05% Tween-20, followed by a block in Odyssey blocking buffer (LI-COR Biosciences) for at least 1 hour. Antibodies to phosphorylated P90RSK(Ser380) (Cell Signaling #9335, rabbit monoclonal) and GAPDH (Fitzgerald 10R-G109a, mouse monoclonal) were added to the cells and incubated overnight at 4° C. pP90RSK(Ser380) antibody was used at a 1:250 dilution; GAPDH was used at a 1:10,000 dilution. After washing with PBS/0.05% Tween-20, the cells were incubated with fluorescently-labeled secondary antibodies (Anti-rabbit-Alexa Flour680, Invitrogen Cat#A21109; Anti-mouse-IRDye800CW, Rockland Inc. Cat#610-131-121) for 1 hour. Both secondary antibodies were used at a 1:1000 dilution. Cells were then washed and analyzed for fluorescence at both wavelengths using the Odyssey Infrared Imaging System (LI-COR Biosciences). Phosphorylated P90RSK (Ser380) signal was normalized to GAPDH signal. Table 1 contains representative data for Examples disclosed herein. The reported IC$_{50}$ in Table 1 may be from a single assay or the mean of multiple assays.

Table 1 contains Examples tested in the above assays:

TABLE 1

| Example # | Biological Example 1 IC$_{50}$ (nM) | Biological Example 2 IC$_{50}$ (nM) |
|---|---|---|
| Example 1 | 0.9 | 22.7 |
| Example 4 | 1.9 | 3.2 |
| Example 5 | 2.5 | 16.8 |
| Example 6 | 2.6 | 58.2 |
| Example 8 | 2.9 | 56.8 |
| Example 33 | 4 | 63.3 |

TABLE 1-continued

| Example # | Biological Example 1 IC$_{50}$ (nM) | Biological Example 2 IC$_{50}$ (nM) |
|---|---|---|
| Example 43 | 5.7 | 68.5 |
| Example 55 | 5.1 | 184.2 |
| Example 56 | 7.8 | 781.1 |
| Example 58 | 11.4 | 436.7 |
| Example 62 | 53.2 | 1400.8 |
| Example 70 | 1.7 | 79.1 |
| Example 72 | 2 | 3.7 |
| Example 81 | 511.4 | |
| Example 86 | 2.8 | 21.8 |
| Example 104 | 2.2 | 19.6 |

Example 1

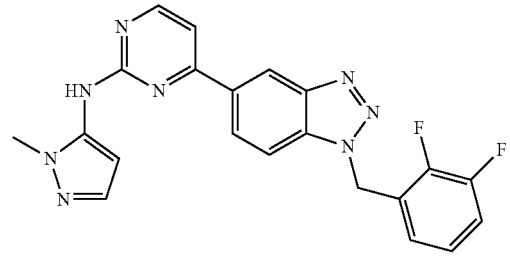 [SMILES: Cn1nccc1Nc1nccc(-c2ccc3c(c2)nnn3Cc2cccc(F)c2F)n1]

4-(1-(2,3-difluorobenzyl)-1H-benzo[1,2,3]triazol-5-yl)-N-(1-methyl-1H-pyrazol-5-yl)pyrimidin-2-amine Step 1: A resealable glass pressure tube was charged with 2,4-dichloropyrimidine (5.0 g, 33.56 mmol), (4-fluoro-3-nitrophenyl)boronic acid (6.83 g, 36.9 mmol), PdCl$_2$(dppf)-CH$_2$Cl$_2$ adduct (1.37 g, 1.68 mmol), 20% aqueous Na$_2$CO$_3$ (16.78 mL, 33.56 mmol) and 1,4-dioxane (67 mL, 33.56 mmol). The mixture was sparged with N$_2$ for 5 minutes. The tube was sealed under N$_2$ with a Teflon® cap, stirred at 90° C. for 5 hours and allowed to cool to room temperature. A precipitate formed with cooling. The mixture was poured into water (50 mL) and attempted to extract in to EtOAc, DCM and 5% MeOH:DCM. However, the solids did not dissolve in the solvents used. Therefore the mixture was filtered (suction filtration) to isolate the solid. The filtrate collected was transferred to a separatory funnel. The phases were separated, and the organic layer was concentrated in vacuo without drying over MgSO$_4$. The residue obtained was combined with the solid from above filtration. Then it was dissolved in hot THF:EtOAc (1:1, 500 mL) and washed with water (1×50 mL). The organic layer was separated, dried (MgSO$_4$), filtered and concentrated in vacuo. The solid residue obtained was crystallized form hot CH$_3$CN to provide 2-chloro-4-(4-fluoro-3-nitrophenyl)pyrimidine (7.9 g, 92.8% yield) as a solid. $^1$H NMR (400 MHz, CDCl$_3$) δ 8.816-8.743 (m, 1H), 8.759 (dd, J1=5.086 Hz, J2=1.174 Hz, 1H), 8.468-8.431 (m, 1H), 7.70 (dd, J1=5.478 Hz, J2=1.174 Hz, 1H), 7.50-7.456 (m, 1H).

Step 2: A suspension of 2-chloro-4-(4-fluoro-3-nitrophenyl)pyrimidine (5 g, 19.7 mmol), 1-methyl-1H-pyrazol-5-amine (1.91 g, 19.7 mmol), Pd$_2$(dba)$_3$ (0.903 g, 0.986 mmol), Xantphos (1.71 g, 2.96 mmol), K$_3$PO$_4$ (8.37 g, 39.4 mmol) in dioxane (98.6 mL, 19.7 mmol) was degassed with nitrogen for 5 minutes and then heated at 120° C. in a sealed tube for 24 hours. The reaction mixture was filtered, and the solid was washed with ethyl acetate. The filtrate was concentrated and purified by flash chromatography eluting with DCM:MeOH gradient 0-10% to provide 4-(4-fluoro-3-nitrophenyl)-N-(1-methyl-1H-pyrazol-5-yl)pyrimidin-2-amine (5.14 g, 83% yield) as a solid. LCMS (APCI neg) m/z 313 (M−1).

Step 3: A solution of 4-(4-fluoro-3-nitrophenyl)-N-(1-methyl-1H-pyrazol-5-yl)pyrimidin-2-amine (100 mg, 0.318 mmol) in DMSO (1.6 mL, 0.318 mmol) under $N_2$ was treated with (2,3-difluorophenyl)methanamine (68.3 mg, 0.477 mmol) followed by potassium carbonate (66 mg, 0.477 mmol). The resulting mixture was stirred at room temperature for 30 minutes. LCMS showed completion of the reaction. The mixture was poured into water (15 mL), and the precipitate formed was filtered and washed with additional water. The solid collected was evaporated from $CH_3CN$ and dried under high vacuum to provide 4-(4-(2,3-difluorobenzyl)amino)-3-nitrophenyl)-N-(1-methyl-1H-pyrazol-5-yl)pyrimidin-2-amine (140 mg, 90.5% yield) as a solid. LCMS (APCI+) m/z 438 (M+1). This material was used for the next reaction without purification.

Step 4: A solution of crude 4-(4-(2,3-difluorobenzyl)amino)-3-nitrophenyl)-N-(1-methyl-1H-pyrazol-5-yl)pyrimidin-2-amine (149 mg, 0.307 mmol) in a mixture of THF (10 mL) and saturated aqueous $NH_4Cl$ (10 mL) at 0° C. was treated with zinc dust (<10 μm, 98+%; 133 mg, 1.99 mmol) with rapid stirring. Once the addition of Zn was completed, the ice bath was removed, and the mixture was stirred at ambient temperature for 30 minutes. The reaction went to completion (LCMS data). The mixture was diluted with EtOAc (60 mL), and the organic layer was separated, dried ($MgSO_4$), filtered and concentrated in vacuo to provide the crude N1-(2,3-difluorobenzyl)-4-(2-((1-methyl-1H-pyrazol-5-yl)amino)pyrimidin-4-yl)benzene-1,2-diamine as a solid. (APCI+) m/z 408 (M+1). This was used for the next reaction directly.

Step 5: To a stirring solution of crude N1-(2,3-difluorobenzyl)-4-(2-((1-methyl-1H-pyrazol-5-yl)amino)pyrimidin-4-yl)benzene-1,2-diamine (233 mg, 0.572 mmol) in 4:1 DCM:concentrated HCl (10 mL) at 0° C. was added $NaNO_2$ (39.5 mg, 0.572 mmol). After 10 minutes, the ice bath was removed, and the mixture was allowed to stir at room temperature for 30 minutes. The mixture was diluted with EtOAc (50 mL), transferred to a separatory funnel and washed with 1 N NaOH followed by brine (10 mL). The organic layer was dried ($MgSO_4$), filtered and concentrated in vacuo. The residue obtained was purified by C-18 flash chromatography (Biotage 25M+) eluting with a gradient of 5-90% $CH_3CN$:water (25CV) on Biotage SP1 unit to provide 4-(1-(2,3-difluorobenzyl)-1H-benzo[d][1,2,3]triazol-5-yl)-N-(1-methyl-1H-pyrazol-5-yl)pyrimidin-2-amine (26.42 mg, 11% yield) as a solid. $^1$H NMR (400 MHz, $(CD_3)_2SO$) δ 9.52 (s, 1H), 8.85 (s, 1H0, 8.56 (d, J=5.075 Hz, 1H), 8.34 (dd, J1=1.171 Hz, J2=8.98 Hz, 1H), 8.013 (d, J=5.47 Hz, 1H), 7.48-7.40 (m, 1H), 7.37 (d, J=1.952 Hz, 1H), 7.25-7.17 (m, 2H), 6.32 (d, J=1.562 Hz, 1H), 6.14 (s, 2H), 3.70 (s, 3H). LCMS (APCI+) m/z 419.1 (M+1). Analytical HPLC area % 96 (220 nm) and area % 98 (254 nM), retention time 3.475 minutes.

Example 2

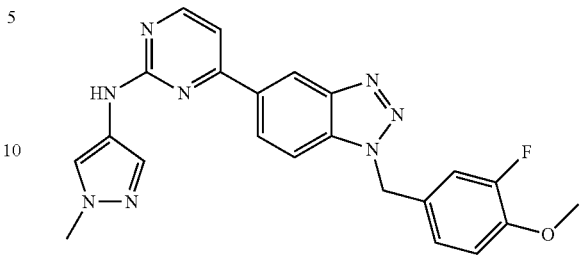

4-(1-(3-fluoro-4-methoxybenzyl)-1H-benzo[d][1,2,3]triazol-5-yl)-N-(1-methyl-1H-pyrazol-4-yl)pyrimidin-2-amine Step 1: A suspension of 2-chloro-4-(4-fluoro-3-nitrophenyl)pyrimidine (1 g, 3.94 mmol) in DMSO (39 mL, 3.94 mmol) at ambient temperature under $N_2$ atmosphere was treated with (3-fluoro-4-methoxyphenyl)methanamine (0.583 mL, 3.94 mmol) followed by $K_2CO_3$ (0.55 g, 3.94 mmol). After 1 hour, the mixture was poured into water (300 mL), and the precipitate formed was filtered and washed with additional water. The solid collected was evaporated from $CH_3CN$, and the residue obtained was triturated with $CH_3CN$ to provide (~95% pure by NMR) 4-(2-chloropyrimidin-4-yl)-N-(3-fluoro-4-methoxybenzyl)-2-nitroaniline (1.55 g, 96.1% yield) as a solid. LCMS (APCI+) m/z 389.1 (M+1).

Step 2: A solution of 4-(2-chloropyrimidin-4-yl)-N-(3-fluoro-4-methoxybenzyl)-2-nitroaniline (1.5 g, 3.86 mmol) in a mixture of THF (80 mL) and saturated aqueous $NH_4Cl$ (40 mL) at 0° C. was treated with zinc dust (<10 μm, 98+%; 1.29 g, 19.3 mmol) as described in Example 1, Step 4, to provide crude 4-(2-chloropyrimidin-4-yl)-N1-(3-fluoro-4-methoxybenzyl)benzene-1,2-diamine (1.48 g, 3.30 mmol, 85.5% yield) as a solid. LCMS (APCI+) m/z 359 (M+1).

Step 3: To a stirring solution of ~80% pure 4-(2-chloropyrimidin-4-yl)-N1-(3-fluoro-4-methoxybenzyl)benzene-1,2-diamine (1.48 g, 3.3 mmol) in DCM:acetic acid (4:1, 60 mL) at ambient temperature was added $NaNO_2$ (0.228 g, 3.30 mmol). Soon after the addition of $NaNO_2$, vigorous gas evolution and slightly exothermic reaction was observed. Therefore the mixture was placed in an ice bath. After 5 minutes, the ice bath was removed, and mixture was stirred at room temperature. After 10 minutes, the reaction went to completion (LCMS data). The mixture was diluted with additional DCM (150 mL), transferred to a separatory funnel and washed with 1 N NaOH followed by brine (50 mL). The organic layer was dried ($MgSO_4$), filtered and concentrated in vacuo. The crude isolated was purified by flash chromatography on silica gel (Ready Sep 80 g) eluting with a gradient of 0-7% MeOH:DCM (12CV) on Biotage SP1 unit. The product isolated was crystallized from EtOAc to provide 5-(2-chloropyrimidin-4-yl)-1-(3-fluoro-4-methoxybenzyl)-1H-benzo[d][1,2,3]triazole (1.1 g, 90% yield) as a solid. LCMS (APCI+) m/z 370 (M+1).

Step 4: A resealable glass pressure tube was charged with a mixture of 5-(2-chloropyrimidin-4-yl)-1-(3-fluoro-4-methoxybenzyl)-1H-benzo[d][1,2,3]triazole (40 mg, 0.11 mmol), 1-methyl-1H-pyrazol-4-amine (21 mg, 0.22 mmol), (9,9-dimethyl-9H-xanthene-4,5-diyl)bis(diphenylphosphine) (9.4 mg, 0.019 mmol), $Pd_2dba_3$ (5 mg, 0.005 mmol), powdered K₃PO₄ (68.9 mg, 0.32 mmol) and 1,4-dioxane (216. μL, 0.11 mmol). The mixture was sparged with N₂ for 3 minutes. The tube was sealed with a Teflon® cap and stirred at 85° C. for 15 hours. The mixture was diluted with dioxane (3 mL) and filtered through a 45 μM filter. The filtrate collected was concentrated, and the residue obtained was purified by C-18 flash chromatography (Biotage 12M+) eluting with a gradient of 5-90% CH₃CN:water on a Biotage SP1 unit. The product isolated was crystalized from MeOH to provide 4-(1-(3-fluoro-4-methoxybenzyl)-1H-benzo[d][1,2,3]triazol-5-yl)-N-(1-methyl-1H-pyrazol-4-yl)pyrimidin-2-amine (8 mg, 17.2% yield) as a solid. ¹H NMR (400 MHz, CDCl₃) δ 8.73 (s, 1H), 8.47 (d, J=5.478 Hz, 1H), 8.18 (d, J=8.216 Hz, 1H), 7.88 (s, 1H), 7.57 (s, 1H), 7.45 (d, J=8.99 Hz, 1H), 7.154 (d, J=5.09 Hz, 1H), 7.06 (d, J=5.86 Hz, 1H), 7.04 (s, 1H), 6.95-6.89 (m, 211), 5.81 (s, 2H), 3.93 (s, 3H), 3.87 (s, 3H). LCMS (APCI+) m/z 431 (M+1), Analytical HPLC: area % 99% (220 nm), retention time 3.447 minutes.

Example 3

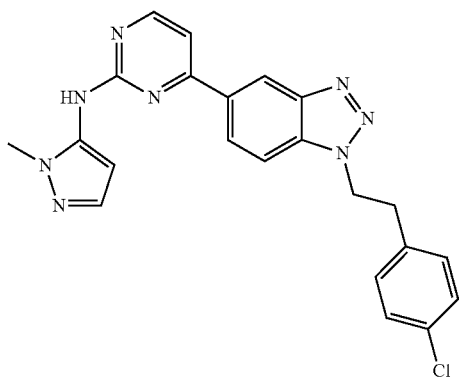 [SMILES: Cn1nccc1Nc1nccc(-c2ccc3c(c2)nnn3CCc2ccc(Cl)cc2)n1]

4-(1-(4-chlorophenethyl)-1H-benzo[d][1,2,3]triazol-5-yl)-N-(1-methyl-1H-pyrazol-5-yl)pyrimidin-2-amine Step 1: A mixture of 4-(4-fluoro-3-nitrophenyl)-N-(1-methyl-1H-pyrazol-5-yl)pyrimidin-2-amine (100 mg, 0.318 mmol) and K₂CO₃ (88 mg, 0.636 mmol) in DMSO (2 mL) at ambient temperature was treated with 2-(4-chlorophenyl)ethanamine (90 μL, 0.636 mmol). After 3 hours, the reaction mixture was diluted with DCM and washed with water. The layers were separated, and the organics were dried (MgSO₄), filtered and concentrated in vacuo to afford 4-(4-((4-chlorophenethyl)amino)-3-nitrophenyl)-N-(1-methyl-1H-pyrazol-5-yl)pyrimidin-2-amine (140 mg, 97.8% yield). Material was taken to the next step directly. LCMS (APCI+) m/z 450.1 (M+1), retention time 3.128 minutes.

Step 2: 4-(4-((4-Chlorophenethyl)amino)-3-nitrophenyl)-N-(1-methyl-1H-pyrazol-5-yl)pyrimidin-2-amine (140 mg, 0.311 mmol) and Zn dust (61 mg, 0.934 mmol) were processed according to the method described in Example 1, Step 4, to provide N1-(4-chlorophenethyl)-4-(2-((1-methyl-1H-pyrazol-5-yl)amino)pyrimidin-4-yl)benzene-1,2-diamine (130 mg, 99.5% yield).

Step 3: N1-(4-Chlorophenethyl)-4-(2-((1-methyl-1H-pyrazol-5-yl)amino)pyrimidin-4-yl)benzene-1,2-diamine (110 mg, 0.262 mmol) and NaNO₂ (18 mg. 0.262 mmol) were processed according to the method described in Example 2, Step 3, to provide 4-(1-(4-chlorophenethyl)-1H-benzo[d][1,2,3]triazol-5-yl)-N-(1-methyl-1H-pyrazol-5-yl)pyrimidin-2-amine (3 mg, 3%). ¹H NMR (CD₃OD) δ 8.74 (s, 1H), 8.51 (d, J=5.47 Hz, 1H), 8.24 (d, J=8.58 Hz, 1H), 7.62-7.60 (m, 2H), 7.53 (d, J=5.47 Hz, 1H), 7.17 (d, J=8.20 Hz, 2H), 7.04 (d, J=8.20 Hz, 2H), 6.52 (d, J=1.95 Hz, 1H), 4.99 (t, J=6.64 Hz, 2H), 3.83 (s, 3H), 3.33 (t, J=6.64 Hz, 2H). LCMS (APCI+) m/z 431.1 (M+1).

Example 4

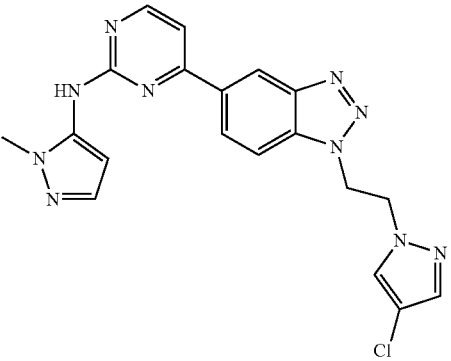 [SMILES: Cn1nccc1Nc1nccc(-c2ccc3c(c2)nnn3CCn2cc(Cl)cn2)n1]

4-(1-(2-(4-chloro-1H-pyrazol-1-yl)ethyl)-1H-benzo[d][1,2,3]triazol-5-yl)-N-(1-methyl-1H-pyrazol-5-yl)pyrimidin-2-amine Step 1: A solution of 4-(4-fluoro-3-nitrophenyl)-N-(1-methyl-1H-pyrazol-5-yl)pyrimidin-2-amine (100 mg, 0.318 mmol) in DMSO (1.5 mL, 0.318 mmol) under N₂ at was treated with 2-(4-chloro-1H-pyrazol-1-yl)ethanamine (93 mg, 0.636 mmol), followed by K₂CO₃ (88 mg, 0.636 mmol). The mixture was stirred at room temperature overnight. The mixture was poured into ice water (25 mL) and extracted with EtOAc (2×). The organic extracts were combined, dried (MgSO₄), filtered and concentrated in vacuo and dried to provide crude 4-(4-((2-(4-chloro-1H-pyrazol-1-yl)ethyl)amino)-3-nitrophenyl)-N-(1-methyl-1H-pyrazol-5-yl)pyrimidin-2-amine. LCMS (APCI+) m/z 440.2 (M+1).

Step 2: Crude 4-(4-((2-(4-chloro-1H-pyrazol-1-yl)ethyl)amino)-3-nitrophenyl)-N-(1-methyl-1H-pyrazol-5-yl)pyrimidin-2-amine (140 mg, 0.318 mmol) and zinc dust (<10 μm, 98+%; 104 mg, 1.59 mmol) were processed according to the synthesis described for Example 1, Step 4, to provide crude N1-(2-(4-chloro-1H-pyrazol-1-yl)ethyl)-4-(2-((1-methyl-1H-pyrazol-5-yl)amino)pyrimidin-4-yl)benzene-1,2-diamine. LCMS (APCI+) m/z 410.2 (M+1).

Step 3: To a stirring solution of crude N1-(2-(4-chloro-1H-pyrazol-1-yl)ethyl)-4-(2-((1-methyl-1H-pyrazol-5-yl)amino)pyrimidin-4-yl)benzene-1,2-diamine (130 mg, 0.317 mmol) in 4:1 DCM:acetic acid (10 mL) at ambient temperature was added NaNO₂ (21.9 mg, 0.317 mmol), and the mixture was stirred at room temperature. After 1 hour, the reaction mixture was diluted with additional DCM (30 mL), transferred to a separatory funnel and washed with 1 N NaOH followed by brine (10 mL). The organic layer was dried (MgSO₄), filtered and concentrated in vacuo. The crude isolated was purified by flash chromatography (Ready Sep 40 g) eluting with a gradient of 1-12% MeOH:DCM (25CV) on Biotage SP1 unit to provide 4-(1-(2-(4-chloro- 1H-pyrazol-1-yl)ethyl)-1H-benzo[d][1,2,3]triazol-5-yl)-N-(1-methyl-1H-pyrazol-5-yl)pyrimidin-2-amine. $^1$H NMR (400 MHz, CDCl$_3$) δ 8.667 (s, 1H), 8.49-8.48 (m, 1H), 8.079-8.048 (m, 1H), 7.565-7.517 (m, 1H), 7.29-7.27 (m, 2H), 7.10 (d, J=9.37 Hz, 1H), 6.885-6.862 (m, 1H), 6.384 (s, 1H), 5.987 (s, 1H), 5.15-5.116 (m, 2H), 4.79-4.71 (m, 2H), 3.834 (s, 3H). LCMS (APCI+) m/z 421.2 (M+1), retention time 1.271 minutes.

Example 5

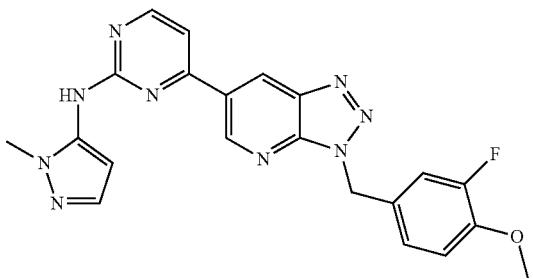

4-(3-(3-fluoro-4-methoxybenzyl)-3H-[1,2,3]triazolo[4,5-b]pyridin-6-yl)-N-(1-methyl-1H-pyrazol-5-yl)pyrimidin-2-amine Step 1: Ammonium chloride (5.0 eq, 14.3 mmol, 0.77 g) and water (20 mL) were added to a stirred solution of 5-bromo-N-[(3-fluoro-4-methoxy-phenyl)methyl]-3-nitro-pyridin-2-amine (1.02 g, 2.86 mmol) and ethanol (50 mL). The mixture was heated to 90° C. Zinc (2.81 g, 43.0 mmol) was added and stirred for 1 hour. The reaction was cooled and filtered through a bed of Celite®, washing with ethyl acetate. The mixture was diluted further with EtOAc and washed with saturated NaHCO$_3$ (aq.), water, and then brine. The product was dried over Na$_2$SO$_4$ and evaporated to afford an oil (0.83 g). MS 326.1.

Step 2: 5-Bromo-N2-[(3-fluoro-4-methoxy-phenyl)methyl]pyridine-2,3-diamine (0.83 g, 2.58 mmol) was suspended in glacial acetic acid (7.69 g, 128 mmol). The suspension was cooled in an ice bath (0° C.) before slowly adding sodium nitrite (212 mg, 3.07 mmol) dissolved in water (2 mL). Sulfuric acid (0.5 mL) was added, and the mixture was stirred at 0° C. for 10 minutes, then warmed to room temperature and stirred for 30 minutes. The mixture was slowly added to 1N NaOH (aq.) in ice. Additional sodium hydroxide was added until the pH reached 4. The mixture was diluted with CH$_2$Cl$_2$, and the phases were separated. The aqueous phase was extracted three times with CH$_2$Cl$_2$. The combined organic phases were washed with saturated NaHCO$_3$ (aq.) and brine, dried over Na$_2$SO$_4$ and evaporated. Purification by CombiFlash (12 g silica column—0-100% ethyl acetate:heptane) furnished a solid (0.5 g). MS 339.0.

Step 3: A microwave vial was charged with 6-bromo-3-[(3-fluoro-4-methoxy-phenyl)methyl]triazolo[4,5-b]pyridine (198 mg, 0.587 mmol), 1,4-dioxane (5 mL), potassium acetate hydrate (173 mg, 1.76 mmol), bis(pinacolato)diboron (298 mg, 1.17 mmol) and [1,1'-[1,1'-bis(diphenylphosphino)ferrocene]-dichloropalladium(II) (21.5 mg, 0.029 mmol, 21.5 mg). The mixture was heated in the microwave at 120° C. for 20 minutes. The mixture was diluted with EtOAc and filtered through Celite®. The mixture was washed with saturated NaHCO$_3$ (aq.) and then brine. The product was dried over Na$_2$SO$_4$, evaporated, and purified by CombiFlash (12 g column; 0-100% EtOAc:heptane) to provide a solid (177 mg). MS=303.

Step 4: A microwave vial was charged with (3-(3-fluoro-4-methoxybenzyl]-3H-[1,2,3]triazolo[4,5-b]pyridin-6-yl] boronic acid (166 mg, 0.55 mmol), 1,4-dioxane (4 mL), 4-iodo-2-methylsulfanyl-pyrimidine (139 mg, 0.55 mmol), 1N Na$_2$CO$_3$ (aqueous, 1.1 mmol) and [1,1'-bis(diphenylphosphino)ferrocene]-dichloropalladium(II) (40 mg, 0.055 mmol). The mixture was purged with nitrogen and then heated in the microwave at 120° C. for 30 minutes. The mixture was diluted with EtOAc and filtered through Celite®. The organic phase was washed with saturated NaHCO$_3$ (aqueous) and then brine. The product was dried over Na$_2$SO$_4$, evaporated and purified by CombiFlash (4 g column; 0-100% EtOAc:heptane) to give 3-(3-fluoro-4-methoxybenzyl)-6-(2-(methylthio)pyrimidin-4-yl)-3H-[1,2,3]triazolo[4,5-b]pyridine (64 mg) as a solid. MS=383.

Step 5: 3-(3-Fluoro-4-methoxybenzyl)-6-(2-(methylthio)pyrimidin-4-yl)-3H-[1,2,3]triazolo[4,5-b]pyridine (64 mg, 0.167 mmol) was dissolved in CH$_2$Cl$_2$ (4 mL). The mixture was cooled to 0° C. before slowly adding 3-chloroperbenzoic acid (285 mg, 1.65 mmol) portionwise over 2 minutes. The mixture was stirred at room temperature overnight. The mixture was quenched with saturated NaHSO$_3$ (aqueous) and diluted with CH$_2$Cl$_2$ (10 mL) The mixture was stirred for 5 minutes, and the phases were separated. The organic phase was washed with saturated NaHCO$_3$ (aqueous) and then brine. The product was dried over Na$_2$SO$_4$ and evaporated to give 3-(3-fluoro-4-methoxybenzyl)-6-(2-(methylsulfonyl)pyrimidin-4-yl)-3H-[1,2,3]triazolo[4,5-b]pyridine as an oil. MS=415.

Step 6: A flask was charged with 3-(3-fluoro-4-methoxybenzyl)-6-(2-(methylsulfonyl)pyrimidin-4-yl)-3H-[1,2,3]triazolo[4,5-b]pyridine (61 mg, 0.147 mmol), DMF (4.0 mL, 51.5 mmol), and 2-methylpyrazol-3-amine (21.4 mg, 0.221 mmol). The mixture was purged with nitrogen and cooled in an ice bath (0° C.). Sodium hydride (11.8 mg, 0.294 mmol) was added, and the mixture was stirred at room temperature. After 30 minutes, the mixture was cooled to 0° C., quenched with water and diluted with EtOAc. The mixture was washed with saturated NaHCO$_3$ (aqueous) and then brine. The product was dried over Na$_2$SO$_4$, evaporated, and purified by HPLC to furnish 4-(3-(3-fluoro-4-methoxybenzyl)-3H-[1,2,3]triazolo[4,5-b]pyridin-6-yl)-N-(1-methyl-1H-pyrazol-5-yl)pyrimidin-2-amine (14.8 mg). MS=432.2.

The following compounds in Table 2 were prepared according to the above procedures using appropriate starting materials and intermediates.

TABLE 2

| Ex. # | Structure | Name | MS |
|---|---|---|---|
| 6 | 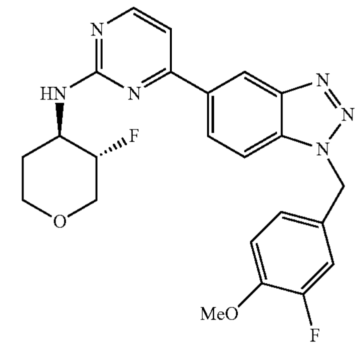 [SMILES: COc1ccc(Cn2nnc3cc(-c4ccnc(N[C@@H]5CCOC[C@H]5F)n4)ccc32)cc1F] | 4-(1-(3-fluoro-4-methoxybenzyl)-1H-benzoyl[d][1,2,3]triazol-5-yl)-N-((3S,4R)-3-fluorotetrahydro-2H-pyran-4-yl)pyrimidin-2-amine | 453.2 (1.507 min) |
| 7 | 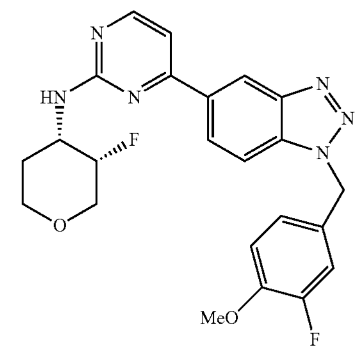 [SMILES: COc1ccc(Cn2nnc3cc(-c4ccnc(N[C@H]5CCOC[C@H]5F)n4)ccc32)cc1F] | 4-(1-(3-fluoro-4-methoxybenzyl)-1H-benzo[d][1,2,3]triazol-5-yl)-N-((3S,4S)-3-fluorotetrahydro-2H-pyran-4-yl)pyrimidin-2-amine | 453.2 (1.481 min) |
| 8 | 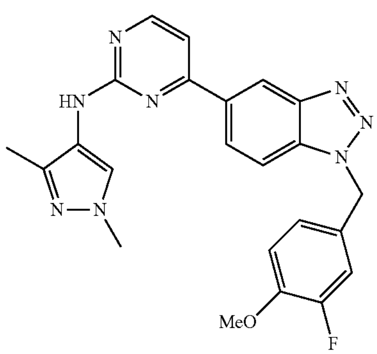 [SMILES: COc1ccc(Cn2nnc3cc(-c4ccnc(Nc5cn(C)nc5C)n4)ccc32)cc1F] | N-(1,3-dimethyl-1H-pyrazol-4-yl)-4-(1-(3-fluoro-4-methoxybenzyl)-1H-benzo[d][1,2,3]triazol-5-yl)pyrimidin-2-amine | 445.2 (1.429 min) |
| 9 | 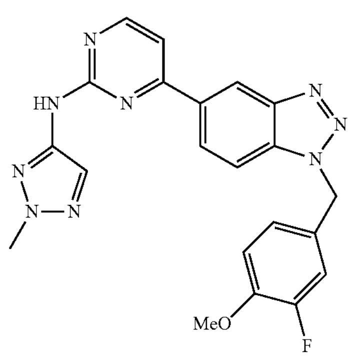 [SMILES: COc1ccc(Cn2nnc3cc(-c4ccnc(Nc5cnn(C)n5)n4)ccc32)cc1F] | 4-(1-(3-fluoro-4-methoxybenzyl)-1H-benzo[d][1,2,3]triazol-5-yl)-N-(2-methyl-2H-1,2,3-triazol-4-yl)pyrimidin-2-amine | 432.2 (1.522 min) |

TABLE 2-continued

| Ex. # | Structure | Name | MS |
|---|---|---|---|
| 10 | 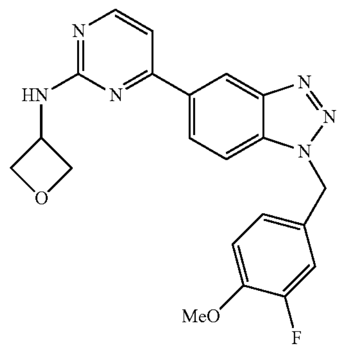 [SMILES: COc1ccc(Cn2nnc3cc(-c4ccnc(NC5COC5)n4)ccc32)cc1F] | 4-(1-(3-fluoro-4-methoxybenzyl)-1H-benzo[d][1,2,3]triazol-5-yl)-N-(oxetan-3-yl)pyrimidin-2-amine | 407.1 (1.388 min) |
| 11 | 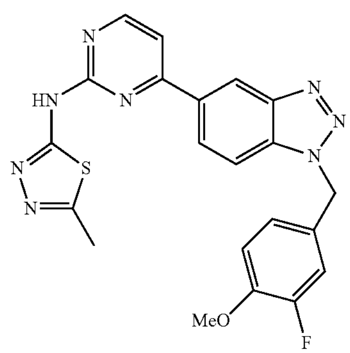 [SMILES: COc1ccc(Cn2nnc3cc(-c4ccnc(Nc5nnc(C)s5)n4)ccc32)cc1F] | N-(4-(1-(3-fluoro-4-methoxybenzyl)-1H-benzol[d][1,2,3]triazol-5-yl)pyrimidin-2-yl)-5-methyl-1,3,4-thiadiazol-2-amine | 449.1 (1.467 min) |
| 12 | 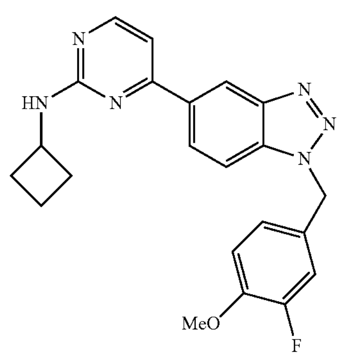 [SMILES: COc1ccc(Cn2nnc3cc(-c4ccnc(NC5CCC5)n4)ccc32)cc1F] | N-cyclobutyl-4-(1-(3-fluoro-4-methoxybenzyl)-1H-benzo[d][1,2,3]triazol-5-yl)pyrimidin-2-amine | 405.2 (1.588 min) |
| 13 | 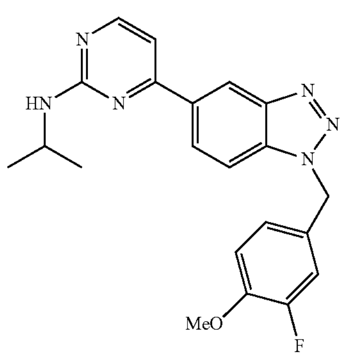 [SMILES: COc1ccc(Cn2nnc3cc(-c4ccnc(NC(C)C)n4)ccc32)cc1F] | 4-(1-(3-fluoro-4-methoxybenzyl)-1H-benzo[d][1,2,3]triazol-5-yl)-N-isopropylpyrimidin-2-amine | 393.1 (1.497 min) |

TABLE 2-continued

| Ex. # | Structure | Name | MS |
|---|---|---|---|
| 14 | 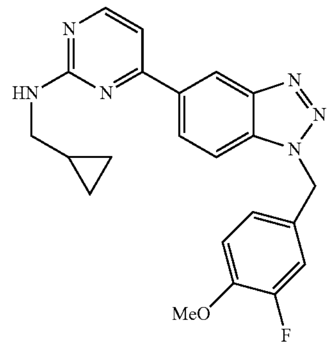 [SMILES: COc1ccc(Cn2nnc3cc(-c4ccnc(NCC5CC5)n4)ccc32)cc1F] | N-(cyclopropylmethyl)-4-(1-(3-fluoro-4-methoxybenzyl)-1H-benzo[d][1,2,3]triazol-5-yl)pyrimidin-2-amine | 405.2 (1.544 min) |
| 15 | 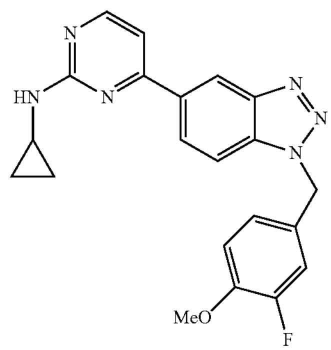 [SMILES: COc1ccc(Cn2nnc3cc(-c4ccnc(NC5CC5)n4)ccc32)cc1F] | N-cyclopropyl-4-(1-(3-fluoro-4-methoxybenzyl)-1H-benzo[d][1,2,3]triazol-5-yl)pyrimidin-2-amine | 391.1 (1.364 min) |
| 16 | 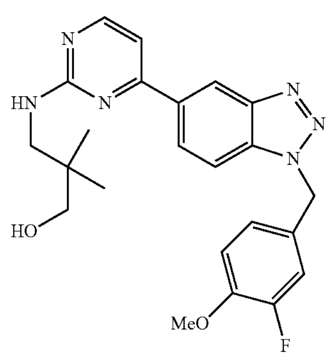 [SMILES: COc1ccc(Cn2nnc3cc(-c4ccnc(NCC(C)(C)CO)n4)ccc32)cc1F] | 3-((4-(1-(3-(fluoro-4-methoxybenzyl)-1H-benzo[d][1,2,3]triazol-5-yl)pyrimidin-2-yl)amino)-2,2-dimethylpropan-1-ol | 437.2 (1.431 min) |
| 17 | 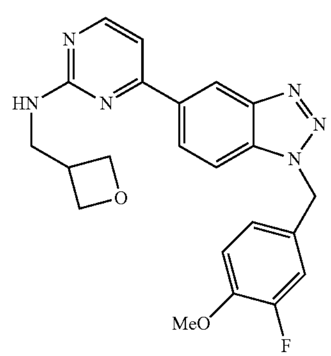 [SMILES: COc1ccc(Cn2nnc3cc(-c4ccnc(NCC5COC5)n4)ccc32)cc1F] | 4-(1-(3-fluoro-4-methoxybenzyl)-1H-benzo[d][1,2,3]triazol-5-yl)-N-(oxetan-3-ylmethyl)pyrimidin-2-amine | 421.1 (1.327 min) |

TABLE 2-continued
| Ex. # | Structure | Name | MS |
|---|---|---|---|
| 18 | 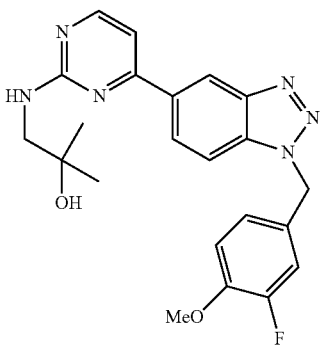 [SMILES: COc1ccc(Cn2nnc3cc(-c4ccnc(NCC(C)(C)O)n4)ccc32)cc1F] | 1-((4-(1-(3-fluoro-4-methoxybenzyl)-1H-benzo[d][1,2,3]triazol-5-yl)pyrimidin-2-yl)amino)-2-methylpropan-2-ol | 423.2 (1.328 min) |
| 19 | 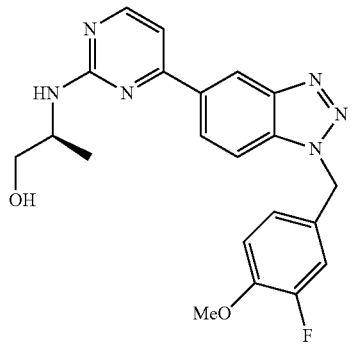 [SMILES: COc1ccc(Cn2nnc3cc(-c4ccnc(N[C@@H](C)CO)n4)ccc32)cc1F] | (S)-2-((4-(1-(3-fluoro-4-methoxybenzyl)-1H-benzo[d][1,2,3]triazol-5-yl)pyrimidin-2-yl)amino)propan-1-ol | 409.2 (1.263 min) |
| 20 | 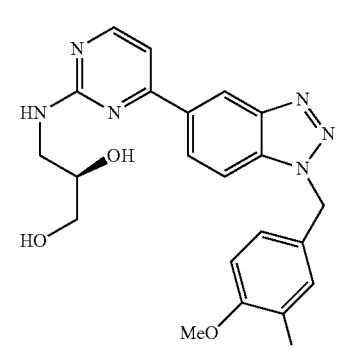 | (R)-3-((4-(1-(3-fluoro-4-methoxybenzyl)-1H-benzo[d][1,2,3]triazol-5-yl)pyrimidin-2-yl)amino)propane-1,2-diol | 425.2 (1.165 min) |
| 21 | 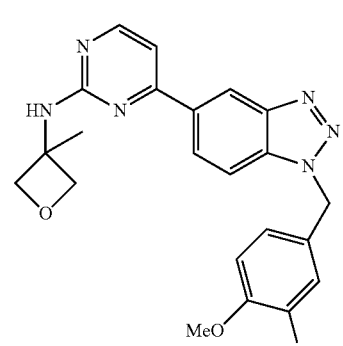 | 4-(1-(3-fluoro-4-methoxybenzyl)-1H-benzo[d][1,2,3]triazol-5-yl)-N-(3-methyloxetan-3-yl)pyrimidin-2-amine | 421.1 (1.437 min) |

TABLE 2-continued

| Ex. # | Structure | Name | MS |
|---|---|---|---|
| 22 | 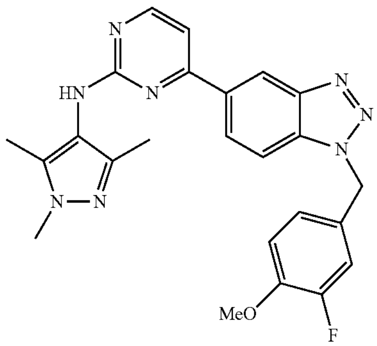 [SMILES: COc1ccc(Cn2nnc3cc(-c4ccnc(Nc5c(C)nn(C)c5C)n4)ccc32)cc1F] | 4-(1-(3-fluoro-4-methoxybenzyl)-1H-benzo[d][1,2,3]triazol-5-yl)-N-(1,3,5-trimethyl-1H-pyrazol-4-yl)pyrimidin-2-amine | 459.2 (1.372 min) |
| 23 | 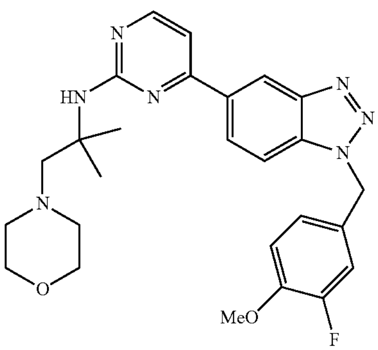 [SMILES: COc1ccc(Cn2nnc3cc(-c4ccnc(NC(C)(C)CN5CCOCC5)n4)ccc32)cc1F] | 4-(1-(3-fluoro-4-methoxybenzyl)-1H-benzo[d][1,2,3]triazol-5-yl)-N-(2-methyl-1-morpholinopropan-2-yl)pyrimidin-2-amine | 492.1 (1.133 min) |
| 24 | 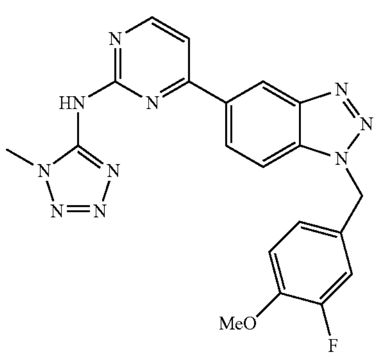 [SMILES: COc1ccc(Cn2nnc3cc(-c4ccnc(Nc5nnnn5C)n4)ccc32)cc1F] | 4-(1-(3-fluoro-4-methoxybenzyl)-1H-benzo[d][1,2,3]triazol-5-yl)-N-(1-methyl-1H-tetrazol-5-yl)pyrimidin-2-amine | 433.1 (1.393 min) |
| 25 | 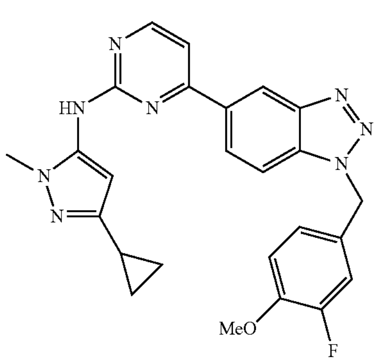 [SMILES: COc1ccc(Cn2nnc3cc(-c4ccnc(Nc5cc(C6CC6)nn5C)n4)ccc32)cc1F] | N-(3-cyclopropyl-1-methyl-1H-pyrazol-5-yl)-4-(1-(3-fluoro-4-methoxybenzyl)-1H-benzoyl[d][1,2,3]triazol-5-yl)pyrimidin-2-amine | 471.2 (1.570 min) |

TABLE 2-continued

| Ex. # | Structure | Name | MS |
|---|---|---|---|
| 26 | 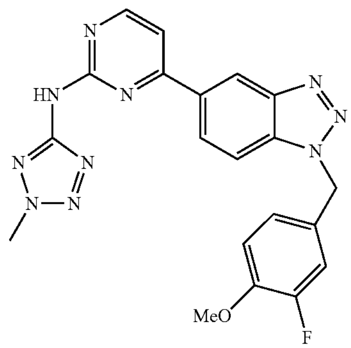 [SMILES: COc1ccc(Cn2nnc3cc(-c4ccnc(Nc5nnn(C)n5)n4)ccc32)cc1F] | 4-(1-(3-fluoro-4-methoxybenzyl)-1H-benzoyl[d][1,2,3]triazol-5-yl)-N-(2-methyl-2H-tetrazol-5-yl)pyrimidin-2-amine | 433.1 (1.403 min) |
| 27 | 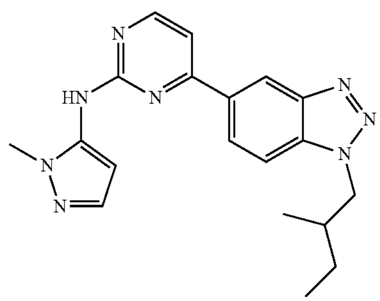 [SMILES: CCC(C)Cn1nnc2cc(-c3ccnc(Nc4ccnn4C)n3)ccc21] | N-(1-methyl-1H-pyrazol-5-yl)-4-(1-(2-methylbutyl)-1H-benzo[d][1,2,3]triazol-5-yl)pyrimidin-2-amine | 363.2 (1.525 min) |
| 28 | 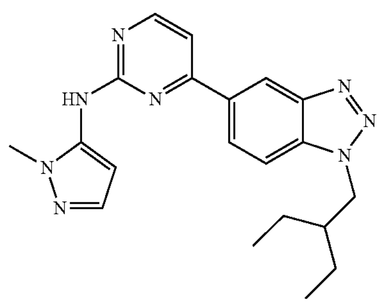 [SMILES: CCC(CC)Cn1nnc2cc(-c3ccnc(Nc4ccnn4C)n3)ccc21] | 4-(1-(2-ethylbutyl)-1H-benzo[d][1,2,3]triazol-5-yl)-N(1-methyl-1H-pyrazol-5-yl)pyrimidin-2-amine | 377.2 (1.629 min) |
| 29 | 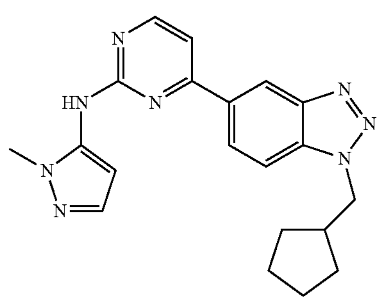 [SMILES: Cn1nccc1Nc1nccc(-c2ccc3c(c2)nnn3CC2CCCC2)n1] | 4-(1-(cyclopentylmethyl)-1H-benzo[d][1,2,3]triazol-5-yl)-N-(1-methyl-1H-pyrazol-5-yl)pyrimidin-2-amine | 375.2 (1.572 min) |
| 30 | 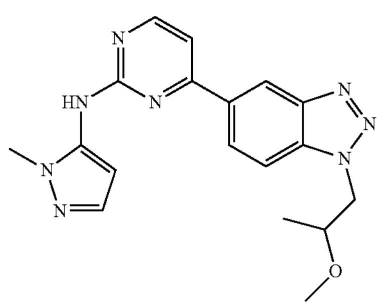 [SMILES: COC(C)Cn1nnc2cc(-c3ccnc(Nc4ccnn4C)n3)ccc21] | 4-(1-(2-methoxypropyl)-1H-benzo[d][1,2,3]triazol-5-yl)-N-(1-methyl-1H-pyrazol-5-yl)pyrimidin-2-amine | 365.2 (1.260 min) |

TABLE 2-continued

| Ex. # | Structure | Name | MS |
|---|---|---|---|
| 31 | 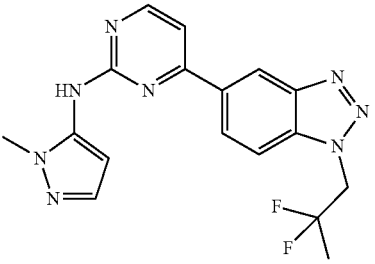 [SMILES: Cn1nccc1Nc1nccc(-c2ccc3c(c2)nnn3CC(C)(F)F)n1] | 4-(1-(2,2-difluoropropyl)-1H-benzo[d][1,2,3]triazol-5-yl)-N-(1-methyl-1H-pyrazol-5-yl)pyrimidin-2-amine | 371.1 (1.296 min) |
| 32 | 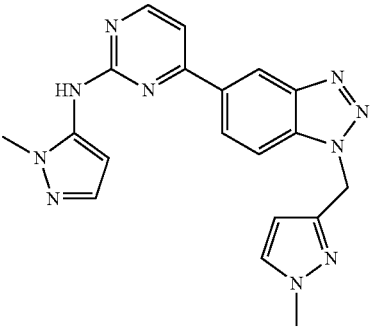 [SMILES: Cn1ccc(Cn2nnc3cc(-c4ccnc(Nc5ccnn5C)n4)ccc32)n1] | 4-(1-((1-methyl-1H-pyrazol-3-yl)methyl)-1H-benzo[d][1,2,3]triazol-5-yl)-N-(1-methyl-1H-pyrazol-5-yl)pyrimidin-2-amine | 387.2 (1.141 min) |
| 33 | 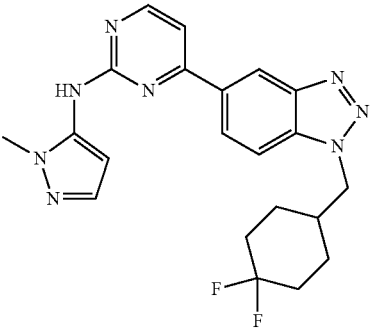 [SMILES: Cn1nccc1Nc1nccc(-c2ccc3c(c2)nnn3CC2CCC(F)(F)CC2)n1] | 4-(1-((4,4-difluorocyclohexyl)methyl)-1H-benzo[d][1,2,3]triazol-5-yl)-N-(1-methyl-1H-pyrazol-5-yl)pyrimidin-2-amine | 425.2 (1.523 min) |
| 34 | 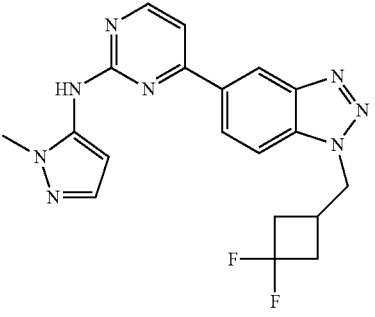 [SMILES: Cn1nccc1Nc1nccc(-c2ccc3c(c2)nnn3CC2CC(F)(F)C2)n1] | 4-(1-((3,3-difluorocyclobutyl)methyl)-1H-benzo[d][1,2,3]triazol-5-yl)-N-(1-methyl-1H-pyrazol-5-yl)pyrimidin-2-amine | 397.1 (1.399 min) |
| 35 | 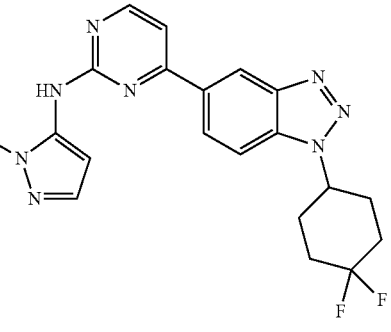 | 4-(1-(4,4-difluorocyclohexyl)-1H-benzo[d][1,2,3]triazol-5-yl)-N-(1-methyl-1H-pyrazol-5-yl)pyrimidin-2-amine | 411.2 (1.460 min) |

TABLE 2-continued

| Ex. # | Structure | Name | MS |
|---|---|---|---|
| 36 | 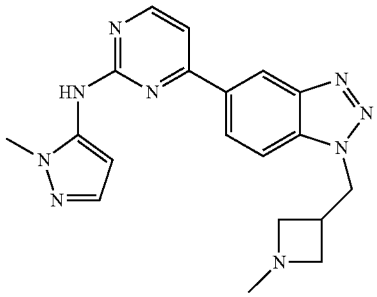 [SMILES: CN1CC(Cn2nnc3cc(-c4ccnc(Nc5ccnn5C)n4)ccc32)C1] | N-(1-methyl-1H-pyrazol-5-yl)-4-(1-((1-methylazetidin-3-yl)methyl)-1H-benzo[d][1,2,3]triazol-5-yl)pyrimidin-2-amine | 376.2 (0.808 min) |
| 37 | 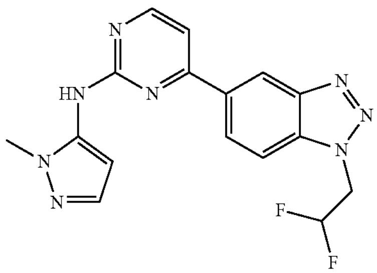 [SMILES: Cn1nccc1Nc1nccc(-c2ccc3c(c2)nnn3CC(F)F)n1] | 4-(1-(2,2-difluoroethyl)-1H-benzo[d][1,2,3]triazol-5-yl)-N-(1-methyl-1H-pyrazol-5-yl)pyrimidin-2-amine | 357.1 (1.211 min) |
| 38 | 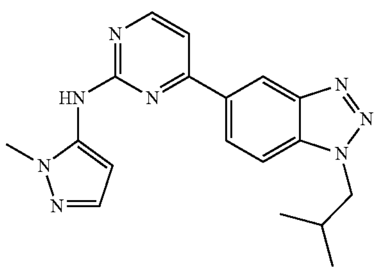 [SMILES: CC(C)Cn1nnc2cc(-c3ccnc(Nc4ccnn4C)n3)ccc21] | 4-(1-isobutyl-1H-benzo[d][1,2,3]triazol-5-yl)-N-(1-methyl-1H-pyrazol-5-yl)pyrimidin-2-amine | 349.2 (1.411 min) |
| 39 | 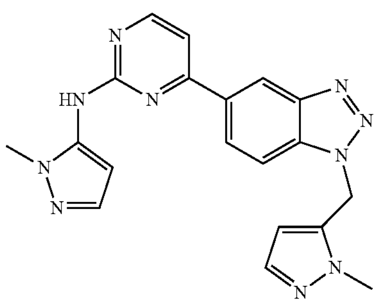 | N-(1-methyl-1H-pyrazol-5-yl)-4-(1-((1-methyl-1H-pyrazol-5-yl)methyl)-1H-benzo[d][1,2,3]triazol-5-yl)pyrimidin-2-amine | 387.2 (1.157 min) |
| 40 | 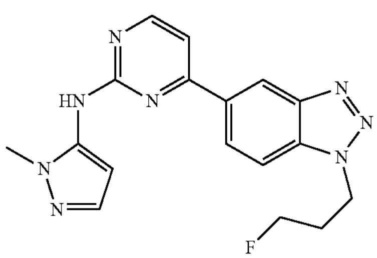 [SMILES: Cn1nccc1Nc1nccc(-c2ccc3c(c2)nnn3CCCF)n1] | 4-(1-(3-fluoropropyl)-1H-benzo[d][1,2,3]triazol-5-yl)-N-(1-methyl-1H-pyrazol-5-yl)pyrimidin-2-amine | 353.2 (1.245 min) |

TABLE 2-continued

| Ex. # | Structure | Name | MS |
|---|---|---|---|
| 41 | 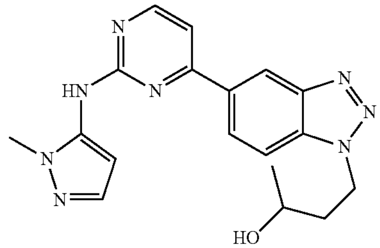 [SMILES: CC(O)CCn1nnc2cc(-c3ccnc(Nc4ccnn4C)n3)ccc21] | 4-(5-(2-(((1-methyl-1H-pyrazol-5-yl)amino)pyrimidin-4-yl)-1H-benzo[d][1,2,3]triazol-1-yl)butan-2-ol | 365.2 (1.125 min) |
| 42 | 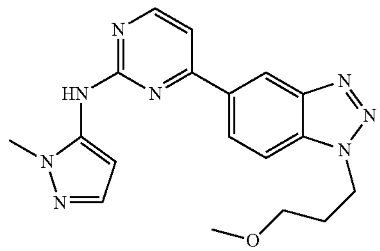 [SMILES: COCCCn1nnc2cc(-c3ccnc(Nc4ccnn4C)n3)ccc21] | 4-(1-(3-methoxypropyl)-1H-benzo[d][1,2,3]triazol-5-yl)-N-(1-methyl-1H-pyrazol-5-yl)pyrimidin-2-amine | 365.2 (1.239 min) |
| 43 | 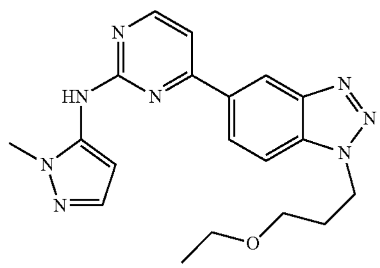 [SMILES: CCOCCCn1nnc2cc(-c3ccnc(Nc4ccnn4C)n3)ccc21] | 4-(1-(3-ethoxypropyl)-1H-benzo[d][1,2,3]triazol-5-yl)-N-(1-methyl-1H-pyrazol-5-yl)pyrimidin-2-amine | 379.2 (1.335 min) |
| 44 | 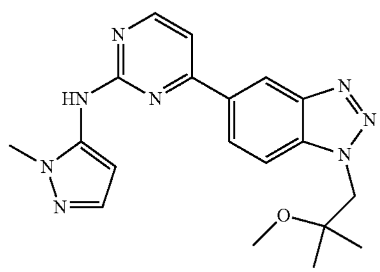 [SMILES: COC(C)(C)Cn1nnc2cc(-c3ccnc(Nc4ccnn4C)n3)ccc21] | 4-(1-(2-methoxy-2-methylpropyl)-1H-benzo[d][1,2,3]triazol-5-yl)-N-(1-methyl-1H-pyrazol-5-yl)pyrimidin-2-amine | 379.2 (1.356 min) |
| 45 | 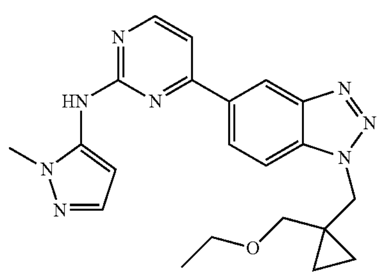 [SMILES: CCOCC1(Cn2nnc3cc(-c4ccnc(Nc5ccnn5C)n4)ccc32)CC1] | 4-(1-((1-(ethoxymethyl)cyclopropyl)methyl)-1H-benzo[d][1,2,3]triazol-5-yl)-N-(1-methyl-1H-pyrazol-5-yl)pyrimidin-2-amine | 405.2 (1.442 min) |
| 46 | 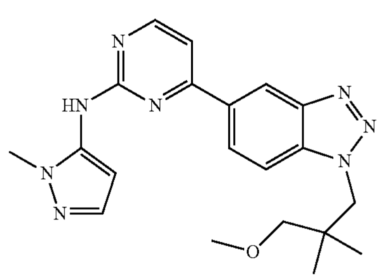 [SMILES: COCC(C)(C)Cn1nnc2cc(-c3ccnc(Nc4ccnn4C)n3)ccc21] | 4-(1-(3-methoxy-2,2-dimethylpropyl)-1H-benzo[d][1,2,3]triazol-5-yl)-N-(1-methyl-1H-pyrazol-5-yl)pyrimidin-2-amine | 393.1 (1.514 min) |

TABLE 2-continued

| Ex. # | Structure | Name | MS |
|---|---|---|---|
| 47 | 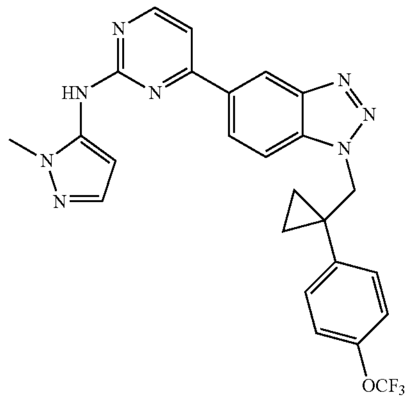 [SMILES: Cn1nccc1Nc1nccc(-c2ccc3c(c2)nnn3CC2(c3ccc(OC(F)(F)F)cc3)CC2)n1] | N-(1-methyl-1H-pyrazol-5-yl)-4-(1-((1-(4-(trifluoromethoxy)phenyl)cyclopropyl)methyl)-1H-benzo[d][1,2,3]triazol-5-yl)pyrimidin-2-amine | 507.2 (1.763 min) |
| 48 | 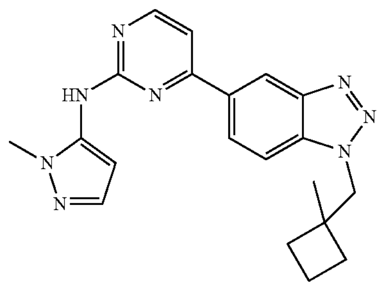 [SMILES: Cn1nccc1Nc1nccc(-c2ccc3c(c2)nnn3CC2(C)CCC2)n1] | N-(1-methyl-1H-pyrazol-5-yl)-4-(1-((1-methylcyclobutyl)methyl)-1H-benzo[d][1,2,3]triazol-5-yl)pyrimidin-2-amine | 375.2 (1.873 min) |
| 49 | 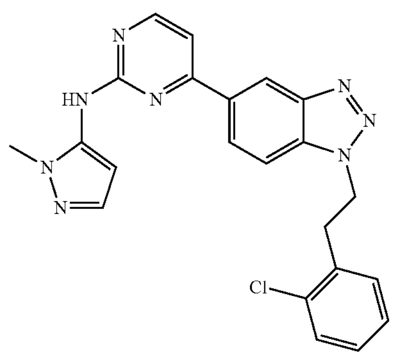 [SMILES: Cn1nccc1Nc1nccc(-c2ccc3c(c2)nnn3CCc2ccccc2Cl)n1] | 4-(1-(2-chlorophenethyl)-1H-benzo-[d][1,2,3]triazol-5-yl)-N-(1-methyl-1H-pyrazol-5-yl)pyrimidin-2-amine | 431.1 (2.738 min) |
| 50 | 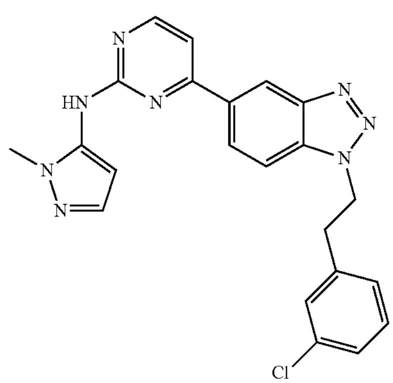 [SMILES: Cn1nccc1Nc1nccc(-c2ccc3c(c2)nnn3CCc2cccc(Cl)c2)n1] | 4-(1-(3-chlorophenethyl)-1H-benzo[d][1,2,3]triazol-5-yl)-N-(1-methyl-1H-pyrazol-5-yl)pyrimidin-2-amine | 431.2 (2.680 min) |

TABLE 2-continued

| Ex. # | Structure | Name | MS |
|---|---|---|---|
| 51 | 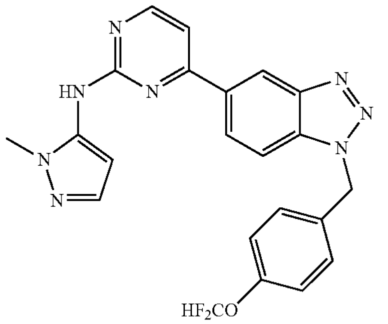 | 4-(1-(4-(difluoromethoxy)benzyl)-1H-benzo[d][1,2,3]triazol-5-yl)-N-(1-methyl-1H-pyrazol-5-yl)pyrimidin-2-amine | 449.2 (2.588 min) |
| 52 | 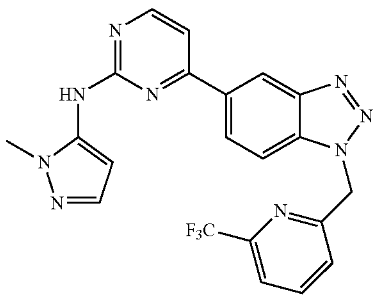 [SMILES: Cn1nccc1Nc1nccc(-c2ccc3c(c2)nnn3Cc2cccc(C(F)(F)F)n2)n1] | N-(1-methyl-1H-pyrazol-5-yl)-4-(1-((6-(trifluoromethyl)pyridin-2-yl)methyl)-1H-benzo[d][1,2,3]triazol-5-yl)pyrimidin-2-amine | 452.1 (2.551 min) |
| 53 | 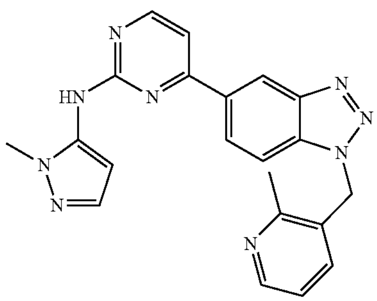 [SMILES: Cc1ncccc1Cn1nnc2cc(-c3ccnc(Nc4ccnn4C)n3)ccc21] | N-(1-methyl-1H-pyrazol-5-yl)-4-(1-((2-methylpyridin-3-yl)methyl)-1H-benzo[d][1,2,3]triazol-5-yl)pyrimidin-2-amine | 398.2 (1.733 min) |
| 54 | 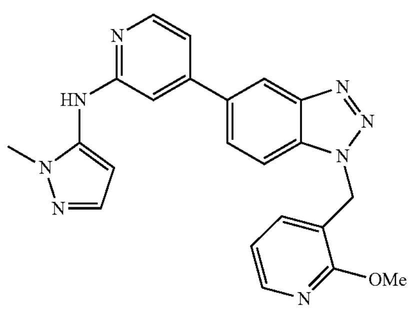 [SMILES: COc1ncccc1Cn1nnc2cc(-c3ccnc(Nc4ccnn4C)c3)ccc21] | 4-(1-((2-methoxypyridin-3-yl)methyl)-1H-benzo[d][1,2,3]triazol-5-yl)-N-(1-methyl-1H-pyrazol-5-yl)pyridin-2-amine | 413.2 (2.125 min) |
| 55 | 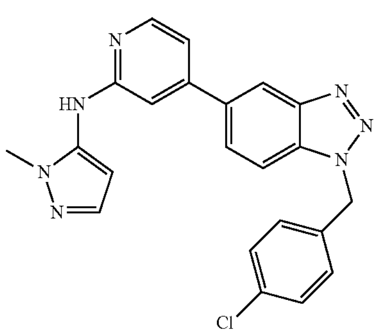 [SMILES: Cn1nccc1Nc1cc(-c2ccc3c(c2)nnn3Cc2ccc(Cl)cc2)ccn1] | 4-(1-(4-chlorobenzyl)-1H-benzo[d][1,2,3]triazol-5-yl)-N-(1-methyl-1H-pyrazol-5-yl)pyridin-2-amine | 416.1 (2.456 min) |

| Ex. # | Structure | Name | MS |
|---|---|---|---|
| 56 | 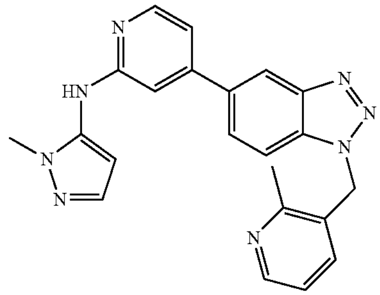 [SMILES: Cc1ncccc1Cn1nnc2cc(-c3ccnc(Nc4ccnn4C)c3)ccc21] | N-(1-methyl-1H-pyrazol-5-yl)-4-(1-((2-methylpyridin-3-yl)methyl)-1H-benzo[d][1,2,3]triazol-5-yl)pyridin-2-amine | 397.2 (1.043 min) |
| 57 | 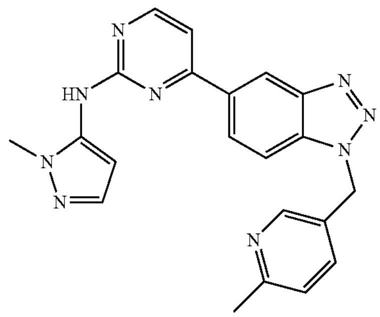 [SMILES: Cc1ccc(Cn2nnc3cc(-c4ccnc(Nc5ccnn5C)n4)ccc32)cn1] | N-(1-methyl-1H-pyrazol-5-yl)-4-(1-((6-methylpyridin-3-yl)methyl)-1H-benzo[d][1,2,3]triazol-5-yl)pyrimidin-2-amine | 398.2 (1.784 min) |
| 58 | 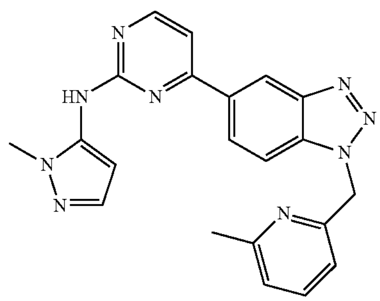 [SMILES: Cc1cccc(Cn2nnc3cc(-c4ccnc(Nc5ccnn5C)n4)ccc32)n1] | N-(1-methyl-1H-pyrazol-5-yl)-4-(1-((6-methylpyridin-2-yl)methyl)-1H-benzo[d][1,2,3]triazol-5-yl)pyrimidin-2-amine | 398.1 (2.183 min) |
| 59 | 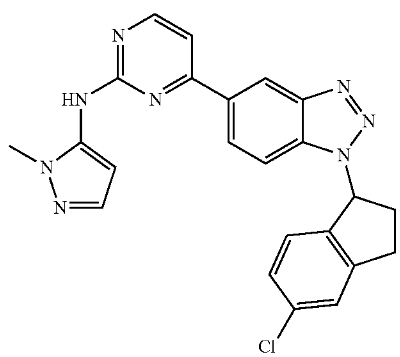 [SMILES: Cn1nccc1Nc1nccc(-c2ccc3c(c2)nnn3C2CCc3cc(Cl)ccc32)n1] | 4-(1-(5-chloro-2,3-dihydro-1H-inden-1-yl)-1H-benzo[d][1,2,3]triazol-5-yl)-N-(1-methyl-1H-pyrazol-5-yl)pyrimidin-2-amine | 443.1 (1.658 min) |
| 60 | 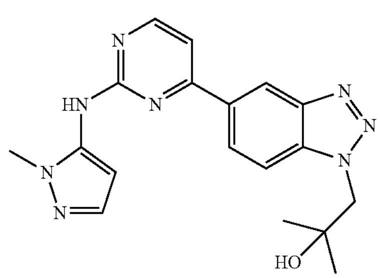 [SMILES: Cn1nccc1Nc1nccc(-c2ccc3c(c2)nnn3CC(C)(C)O)n1] | 2-methyl-1-(5-(2-((1-methyl-1H-pyrazol-5-yl)amino)pyrimidin-4-yl)-1H-benzo[d][1,2,3]triazol-1-yl)propan-2-ol | 365.2 (1.112 min) |

TABLE 2-continued

| Ex. # | Structure | Name | MS |
|---|---|---|---|
| 61 | 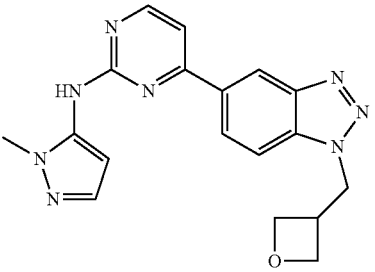 [SMILES: Cn1nccc1Nc1nccc(-c2ccc3c(c2)nnn3CC2COC2)n1] | N-(1-methyl-1H-pyrazol-5-yl)-4-(1-(oxetan-3-ylmethyl)-1H-benzo[d][1,2,3]triazol-5-yl)pyrimidin-2-amine | 363.2 (1.083 min) |
| 62 | 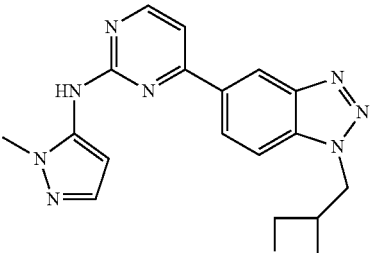 | 4-(1-(azetidin-3-ylmethyl)-1H-benzo[d][1,2,3]triazol-5-yl)-N-(1-methyl-1H-pyrazol-5-yl)pyrimidin-2-amine | 362.1 (0.701 min) |
| 63 | 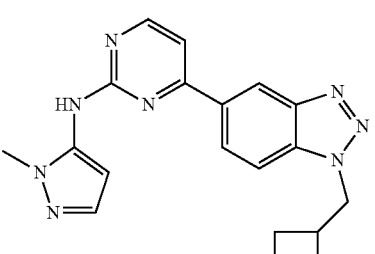 | tert-butyl 3-((5-(2-((1-methyl-1H-pyrazol-5-yl)amino)pyrimidin-4-yl)-1H-benzo[d][1,2,3]triazol-1-yl)methyl)azetidine-1-carboxylate | 462.2 (1.231 min) |
| 64 | 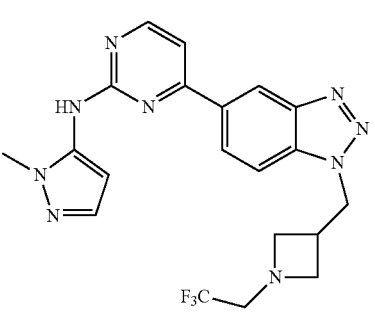 [SMILES: Cn1nccc1Nc1nccc(-c2ccc3c(c2)nnn3CC2CN(CC(F)(F)F)C2)n1] | N-(1-methyl-1H-pyrazol-5-yl)-4-(1-((1-(2,2,2-trifluoroethyl)azetidin-3-yl)methyl)-1H-benzo[d][1,2,3]triazol-5-yl)pyrimidin-2-amine | 442.2 (1.13 min) |
| 65 | 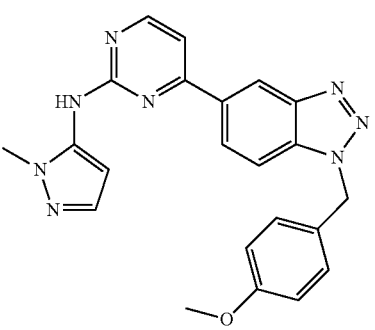 [SMILES: COc1ccc(Cn2nnc3cc(-c4ccnc(Nc5ccnn5C)n4)ccc32)cc1] | 4-(1-(4-methoxybenzyl)-1H-benzo[d][1,2,3]triazol-5-yl)-N-(1-methyl-1H-pyrazol-5-yl)pyrimidin-2-amine | 413.2 (2.524 min) |

TABLE 2-continued

| Ex. # | Structure | Name | MS |
|---|---|---|---|
| 66 | 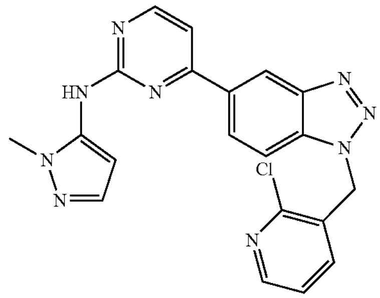 [SMILES: Cn1nccc1Nc1nccc(-c2ccc3c(c2)nnn3Cc2cccnc2Cl)n1] | 4-(1-((2-chloropyridin-3-yl)methyl)-1H-benzo[d][1,2,3]triazol-5-yl)-N-(1-methyl-1H-pyrazol-5-yl)pyrimidin-2-amine | 418.1 (1.075 min) |
| 67 | 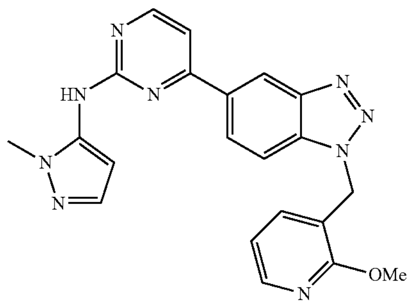 [SMILES: COc1ncccc1Cn1nnc2cc(-c3ccnc(Nc4ccnn4C)n3)ccc21] | 4-(1-((2-methoxypyridin-3-yl)methyl)-1H-benzo[d][1,2,3]triazol-5-yl)-N-(1-methyl-1H-pyrazol-5-yl)pyrimidin-2-amine | 414.2 (1.126 min) |
| 68 | 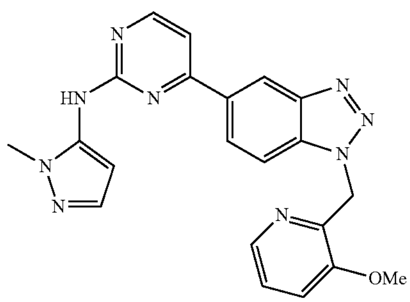 [SMILES: COc1cccnc1Cn1nnc2cc(-c3ccnc(Nc4ccnn4C)n3)ccc21] | 4-(1-((3-methoxypyridin-2-yl)methyl)-1H-benzo[d][1,2,3]triazol-5-yl)-N-(1-methyl-1H-pyrazol-5-yl)pyrimidin-2-amine | 414.1 (1.060 min) |
| 69 | 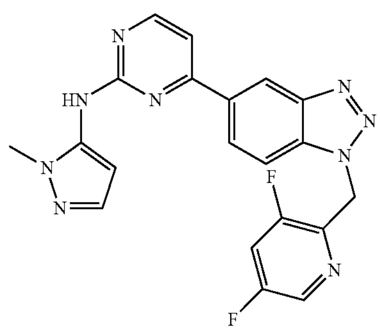 [SMILES: Cn1nccc1Nc1nccc(-c2ccc3c(c2)nnn3Cc2ncc(F)cc2F)n1] | 4-(1-((3,5-difluoropyridin-2-yl)methyl)-1H-benzo[d][1,2,3]triazol-5-yl)-N-(1-methyl-1H-pyrazol-5-yl)pyrimidin-2-amine | 420.1 (1.110 min) |
| 70 | 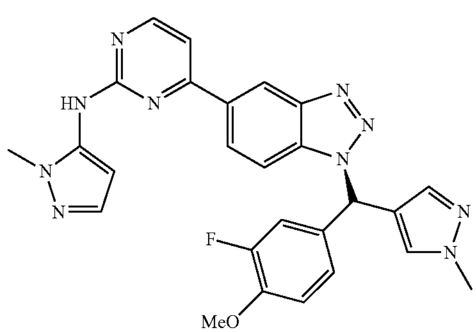 | (S)-4-(1-((3-fluoro-4-methoxyphenyl)(1-methyl-1H-pyrazol-4-yl)methyl)-1H-benzo[d][1,2,3]triazol-5-yl)-N-(1-methyl-1H-pyrazol-5-yl)pyrimidin-2-amine | 509 (M − 1) (1.175 min) |

TABLE 2-continued

| Ex. # | Structure | Name | MS |
|---|---|---|---|
| 71 | 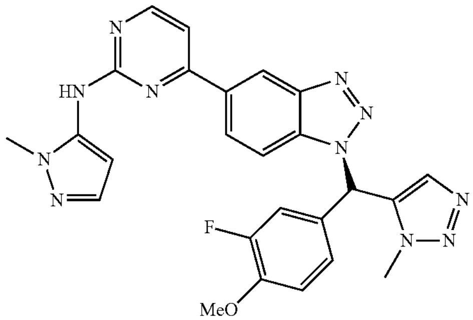 | (S)-4-(1-((3-fluoro-4-methoxyphenyl)(1-methyl-1H-1,2,3-triazol-5-yl)methyl)-1H-benzo[d][1,2,3]triazol-5-yl)-N-(1-methyl-1H-pyrazol-5-yl)pyrimidin-2-amine | 510.1 (M − 1) (1.133 min) |
| 72 | 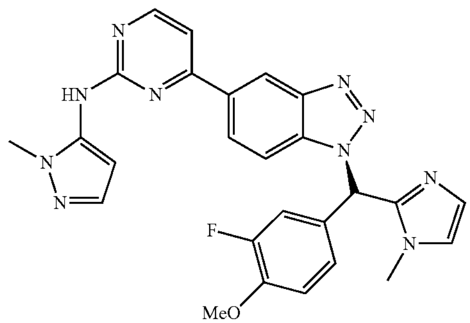 | (S)-4-(1-((3-fluoro-4-methoxyphenyl)(1-methyl-1H-imidazol-2-yl)methyl)-1H-benzo[d][1,2,3]triazol-5-yl)-N-(1-methyl-1H-pyrazol-5-yl)pyrimidin-2-amine | Did not ionize |
| 73 | 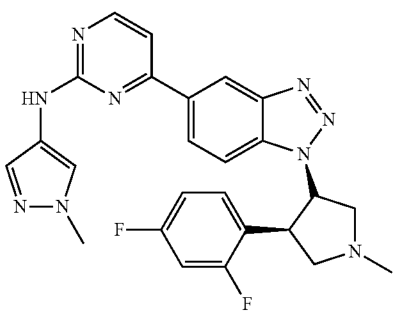 | 4-(1-((3S,4R)-4-(2,4-difluorophenyl)-1-methylpyrrolidin-3-yl)-1H-benzo[d][1,2,3]triazol-5-yl)-N(1-methyl-1H-pyrazol-4-yl)pyrimidin-2-amine | 488.2 (1.130 min) |
| 74 | 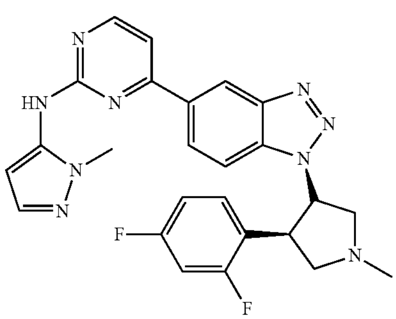 | 4-(1-((3S,4R)-4-(2,4-difluorophenyl)-1-methylpyrrolidin-3-yl)-1H-benzo[d][1,2,3]triazol-5-yl)-N-(1-methyl-1H-pyrazol-5-yl)pyrimidin-2-amine | 488.2 (1.063 min) |
| 75 | 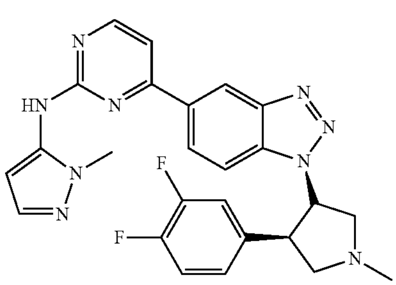 | 4-(1-((3S,4R)-4-(3,4-difluorophenyl)-1-methylpyrrolidin-3-yl)-1H-benzo[d][1,2,3]triazol-5-yl)-N-(1-methyl-1H-pyrazol-5-yl)pyrimidin-2-amine | 488.2 (1.278 min) |

TABLE 2-continued

| Ex. # | Structure | Name | MS |
|---|---|---|---|
| 76 | 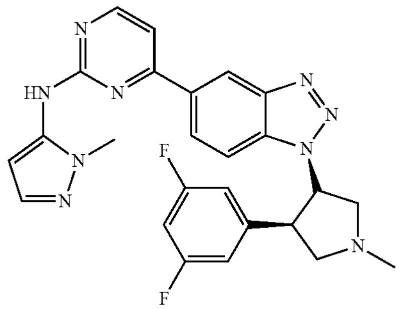 | 4-(1-((3S,4R)-4-(3,5-difluorophenyl)-1-methylpyrrolidin-3-yl)-1H-benzo[d][1,2,3]triazol-5-yl)-N-(1-methyl-1H-pyrazol-5-yl)pyrimidin-2-amine | 488.2 (1.092 min) |
| 77 | 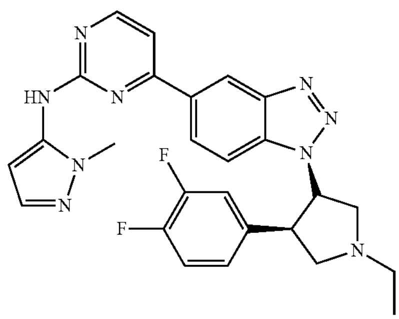 | 4-(1-((3S,4R)-4-(3,4-difluorophenyl)-1-ethylpyrrolidin-3-yl)-1H-benzo[d][1,2,3]triazol-5-yl)-N-(1-methyl-1H-pyrazol-5-yl)pyrimidin-2-amine | 502.2 (1.347 min) |
| 78 | 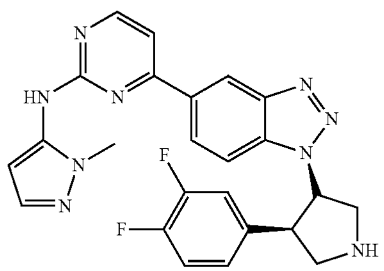 | 4-(1-((3S,4R)-4-(3,4-difluorophenyl)pyrrolidin-3-yl)-1H-benzo[d][1,2,3]triazol-5-yl)-N-(1-methyl-1H-pyrazol-5-yl)pyrimidin-2-amine | 474.2 (1.010 min) |
| 79 | 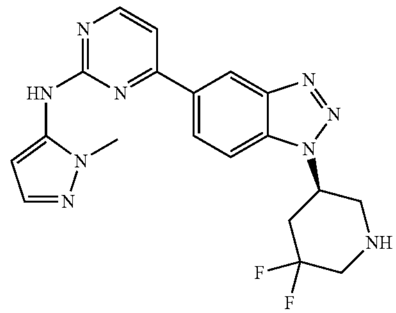 [SMILES: Cn1nccc1Nc1nccc(-c2ccc3c(c2)nnn3[C@H]2CNCC(F)(F)C2)n1] | (R)-4-(1-(5,5-difluoropiperidin-3-yl)-1H-benzo[d][1,2,3]triazol-5-yl)-N-(1-methyl-1H-pyrazol-5-yl)pyrimidin-2-amine | 412.1 (1.002 min) |
| 80 | 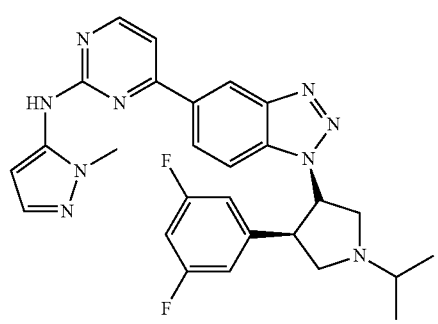 | 4-(1-((3S,4R-4-(3,5-difluorophenyl)-1-isopropylpyrrolidin-3-yl)-1H-benzo[d][1,2,3]triazol-5-yl)-N-(1-methyl-1H-pyrazol-5-yl)pyrimidin-2-amine | 516.2 (1.125 min) |

TABLE 2-continued

| Ex. # | Structure | Name | MS |
|---|---|---|---|
| 81 | 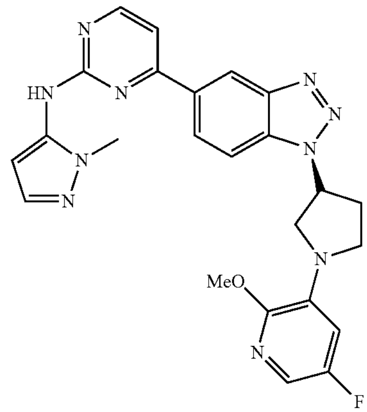 | (S)-4-(1-(1-(5-fluoro-2-methoxypyridin-3-yl)pyrrolidin-3-yl)-1H-benzo[d][1,2,3]triazol-5-yl)-N-(1-methyl-1H-pyrazol-5-yl)pyrimidin-2-amine | 487.2 (1.591 min) |
| 82 | 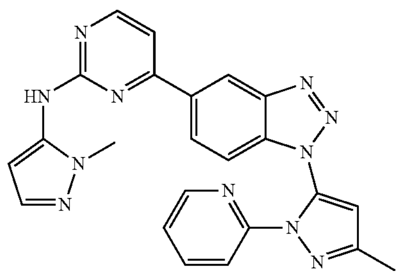 [SMILES: Cc1cc(-n2nnc3cc(-c4ccnc(Nc5ccnn5C)n4)ccc32)n(-c2ccccn2)n1] | 4-(1-(3-methyl-1-(pyridin-2-yl)-1H-pyrazol-5-yl)-1H-benzo[d][1,2,3]triazol-5-yl)-N-(1-methyl-1H-pyrazol-5-yl)pyrimidin-2-amine | 450.2 (1.489 min) |
| 83 | 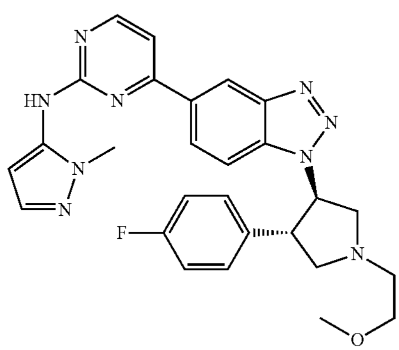 [SMILES: COCCN1C[C@H](c2ccc(F)cc2)[C@@H](n2nnc3cc(-c4ccnc(Nc5ccnn5C)n4)ccc32)C1] | 4-(1-((3R,4S)-4-(4-fluorophenyl)-1-(2-methoxyethyl)pyrrolidin-3-yl)-1H-benzo[d][1,2,3]triazol-5-yl)-N-(1-methyl-1H-pyrazol-5-yl)pyrimidin-2-amine | 514.2 (1.343 min) |
| 84 | 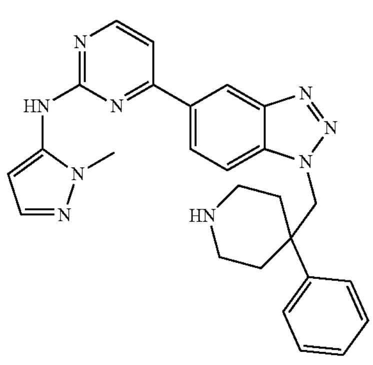 [SMILES: Cn1nccc1Nc1nccc(-c2ccc3c(c2)nnn3CC2(c3ccccc3)CCNCC2)n1] | N-(1-methyl-1H-pyrazol-5-yl)-4-(1-((4-phenylpiperidin-4-yl)methyl)-1H-benzo[d][1,2,3]triazol-5-yl)pyrimidin-2-amine | 466.2 (0.848 min) |

TABLE 2-continued

| Ex. # | Structure | Name | MS |
|---|---|---|---|
| 85 | 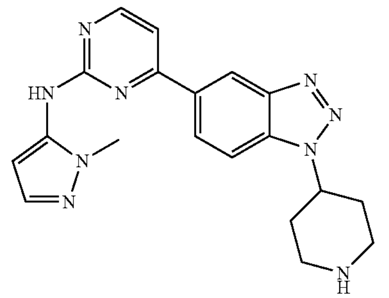 [SMILES: Cn1nccc1Nc1nccc(-c2ccc3c(c2)nnn3C2CCNCC2)n1] | N-(1-methyl-1H-pyrazol-5-yl)-4-(1-(piperidin-4-yl)-1H-benzo[d][1,2,3]triazol-5-yl)pyrimidin-2-amine | 376.2 (0.671 min) |
| 86 | 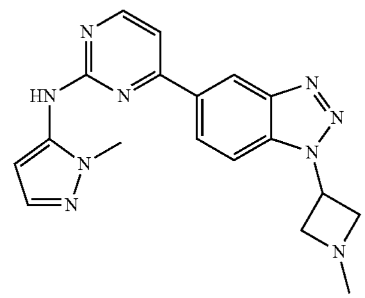 [SMILES: CN1CC(n2nnc3cc(-c4ccnc(Nc5ccnn5C)n4)ccc32)C1] | N-(1-methyl-1H-pyrazol-5-yl)-4-(1-(1-methylazetidin-3-yl)-1H-benzo[d][1,2,3]triazol-5-yl)pyrimidin-2-amine | 362.2 (0.728 min) |
| 87 | 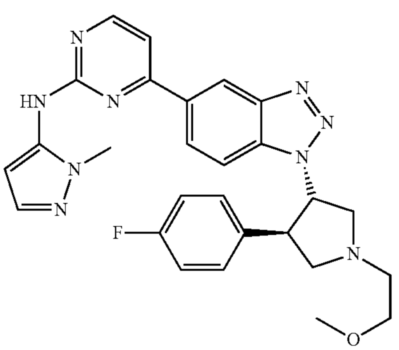 | 4-(1-((3S,4R)-4-(4-fluorophenyl)-1-(2-methoxyethyl)pyrrolidin-3-yl)-1H-benzo[d][1,2,3]triazol-5-yl)-N-(1-methyl-1H-pyrazol-5-yl)pyrimidin-2-amine | 514.2 (1.292 min) |
| 88 | 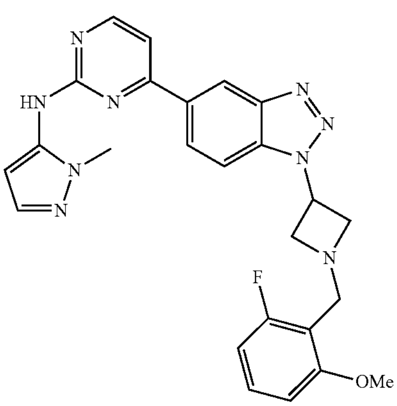 [SMILES: COc1cccc(F)c1CN1CC(n2nnc3cc(-c4ccnc(Nc5ccnn5C)n4)ccc32)C1] | 4-(1-(1-(2-fluoro-6-methoxybenzyl)azetidin-3-yl)-1H-benzo[d][1,2,3]triazol-5-yl)-N-(1-methyl-1H-pyrazol-5-yl)pyrimidin-2-amine | 486.2 (1.213 min) |

TABLE 2-continued

| Ex. # | Structure | Name | MS |
|---|---|---|---|
| 89 | 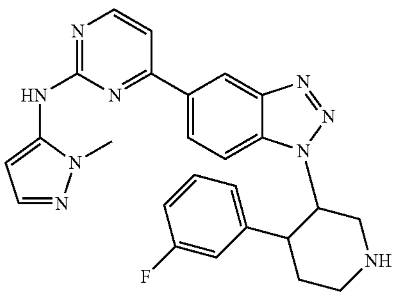 [SMILES: Cn1nccc1Nc1nccc(-c2ccc3c(c2)nnn3C2CNCCC2c2cccc(F)c2)n1] | 4-(1-(4-(3-fluorophenyl)piperidin-3-yl)-1H-benzoyl[d][1,2,3]triazol-5-yl)-N-(1-methyl-1H-pyrazol-5-yl)pyrimidin-2-amine | 470.2 (0.988 min) |
| 90 | 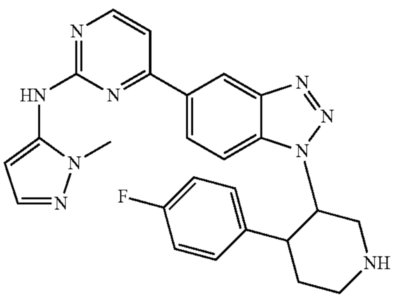 [SMILES: Cn1nccc1Nc1nccc(-c2ccc3c(c2)nnn3C2CNCCC2c2ccc(F)cc2)n1] | 4-(1-(4-(4-fluorophenyl)piperidin-3-yl)-1H-benzo[d][1,2,3]triazol-5-yl)-N-(1-methyl-1H-pyrazol-5-yl)pyrimidin-2-amine | 470.2 (0.946 min) |
| 91 | 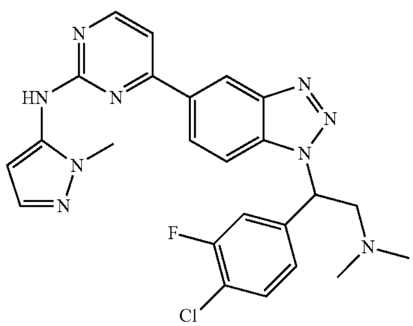 [SMILES: CN(C)CC(c1ccc(Cl)c(F)c1)n1nnc2cc(-c3ccnc(Nc4ccnn4C)n3)ccc21] | 4-(1-(1-(4-chloro-3-fluorophenyl)-2-(dimethylamino)ethyl)-1H-benzo[d][1,2,3]triazol-5-yl)-N-(1-methyl-1H-pyrazol-5-yl)pyrimidin-2-amine | 492.1 (1.145 min) |
| 92 | 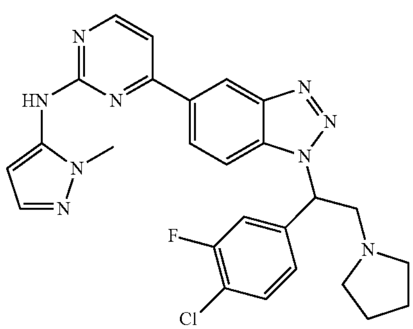 [SMILES: Cn1nccc1Nc1nccc(-c2ccc3c(c2)nnn3C(CN2CCCC2)c2ccc(Cl)c(F)c2)n1] | 4-(1-(1-(4-chloro-3-fluorophenyl)-2-(pyrrolidin-1-yl)ethyl)-1H-benzo[d][1,2,3]triazol-5-yl)-N-(1-methyl-1H-pyrazol-5-yl)pyrimidin-2-amine | 518.2 (1.178 min) |
| 93 | 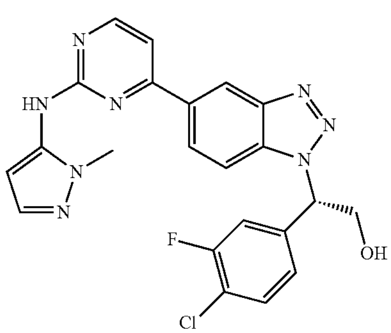 [SMILES: Cn1nccc1Nc1nccc(-c2ccc3c(c2)nnn3[C@H](CO)c2ccc(Cl)c(F)c2)n1] | (S)-2-(4-chloro-3-fluorophenyl)-2-(5-(2-((1-methyl-1H-pyrazol-5-yl)amino)pyrimidin-4-yl)-1H-benzo[d][1,2,3]triazol-1-yl)ethanol | 465.1 (1.457 min) |

TABLE 2-continued

| Ex. # | Structure | Name | MS |
|---|---|---|---|
| 94 | 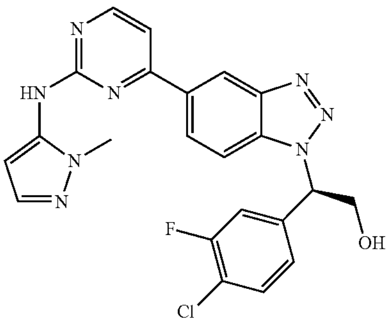 [SMILES: Cn1nccc1Nc1nccc(-c2ccc3c(c2)nnn3[C@@H](CO)c2ccc(Cl)c(F)c2)n1] | (R)-2-(4-chloro-3-fluorophenyl)-2-(5-(2-((1-methyl-1H-pyrazol-5-yl)amino)pyrimidin-4-yl)-1H-benzo[d][1,2,3]triazol-1-yl)ethanol | 465.1 (1.453 min) |
| 95 | 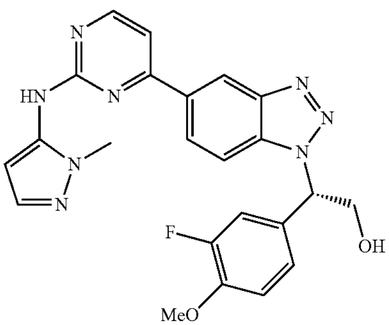 [SMILES: COc1ccc([C@@H](CO)n2nnc3cc(-c4ccnc(Nc5ccnn5C)n4)ccc32)cc1F] | (S)-2-(3-fluoro-4-methoxyphenyl)-2-(5-(2-((1-methyl-1H-pyrazol-5-yl)amino)pyrimidin-4-yl)-1H-benzo[d][1,2,3]triazol-1-yl)ethanol | 461.2 (1.300 min) |
| 96 | 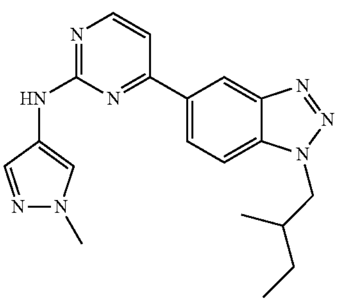 [SMILES: CCC(C)Cn1nnc2cc(-c3ccnc(Nc4cnn(C)c4)n3)ccc21] | N-(1-methyl-1H-pyrazol-4-yl)-4-(1-(2-methylbutyl)-1H-benzo[d][1,2,3]triazol-5-yl)pyrimidin-2-amine | 363.2 (1.527 min) |
| 97 | 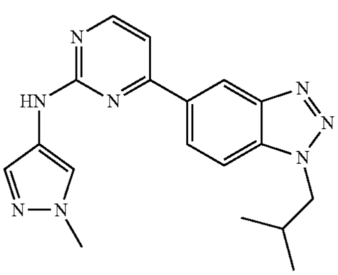 [SMILES: CC(C)Cn1nnc2cc(-c3ccnc(Nc4cnn(C)c4)n3)ccc21] | 4-(1-isobutyl-1H-benzo[d][1,2,3]triazol-5-yl)-N-(1-methyl-1H-pyrazol-4-yl)pyrimidin-2-amine | 349.2 (1.414 min) |
| 98 | 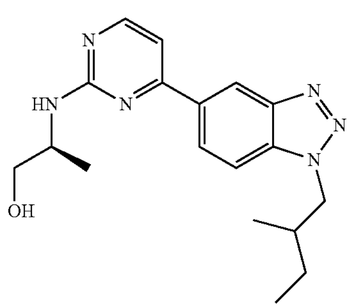 [SMILES: CCC(C)Cn1nnc2cc(-c3ccnc(N[C@@H](C)CO)n3)ccc21] | (2S)2-((4-(1-(2-methylbutyl)-1H-benzo[d][1,2,3]triazol-5-yl)pyrimidin-2-yl)amino)propan-1-ol | 341.2 (1.319 min) |

TABLE 2-continued

| Ex. # | Structure | Name | MS |
|---|---|---|---|
| 99 | 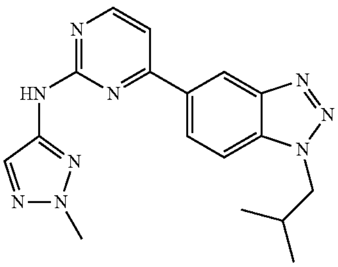 [SMILES: CC(C)Cn1nnc2cc(-c3ccnc(Nc4cnn(C)n4)n3)ccc21] | 4-(1-isobutyl-1H-benzo[d][1,2,3]triazol-5-yl)-N-(2-methyl-2H-1,2,3-triazol-4-yl)pyrimidin-2-amine | 350.2 (1.511 min) |
| 100 | 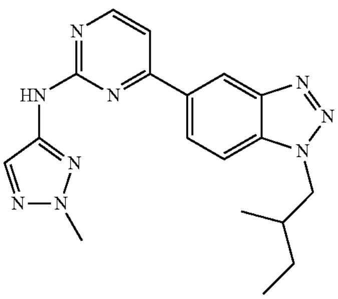 [SMILES: CCC(C)Cn1nnc2cc(-c3ccnc(Nc4cnn(C)n4)n3)ccc21] | N-(2-methyl-2H-1,2,3-triazol-4-yl)-4-(1-(2-methylbutyl)-1H-benzo[d][1,2,3]triazol-5-yl)pyrimidin-2-amine | 364.2 (1.623 min) |
| 101 | 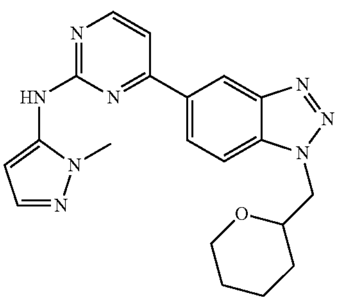 [SMILES: Cn1nccc1Nc1nccc(-c2ccc3c(c2)nnn3CC2CCCCO2)n1] | N-(1-methyl-1H-pyrazol-5-yl)-4-(1-((tetrahydro-2H-pyran-2-yl)methyl)-1H-benzoyl[d][1,2,3]triazol-5-yl)pyrimidin-2-amine | 391.2 (1.366 min) |
| 102 | 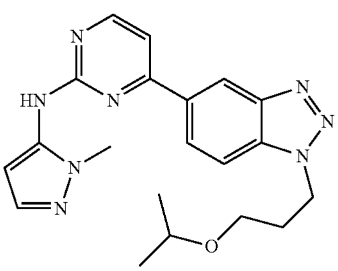 [SMILES: CC(C)OCCCn1nnc2cc(-c3ccnc(Nc4ccnn4C)n3)ccc21] | 4-(1-(3-isopropoxypropyl)-1H-benzo[d][1,2,3]triazol-5-yl)-N-(1-methyl-1H-pyrazol-5-yl)pyrimidin-2-amine | 393.2 (1.396 min) |
| 103 | 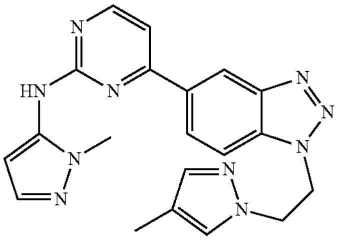 [SMILES: Cc1cnn(CCn2nnc3cc(-c4ccnc(Nc5ccnn5C)n4)ccc32)c1] | 4-(1-(2-(4-methyl-1H-pyrazol-1-yl)ethyl)-1H-benzo[d][1,2,3]triazol-5-yl)-N-(1-methyl-1H-pyrazol-5-yl)pyrimidin-2-amine | 401.2 (1.201 min) |

TABLE 2-continued

| Ex. # | Structure | Name | MS |
|---|---|---|---|
| 104 | 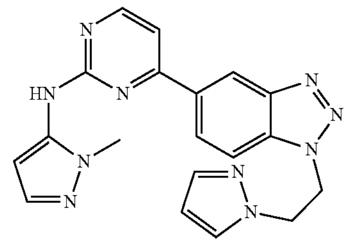 [SMILES: Cn1nccc1Nc1nccc(-c2ccc3c(c2)nnn3CCn2cccn2)n1] | 4-(1-(2-(1H-pyrazol-1-yl)ethyl)-1H-benzo[d][1,2,3]triazol-5-yl)-N-(1-methyl-1H-pyrazol-5-yl)pyrimidin-2-amine | 387.2 (1.130 min) |
| 105 | 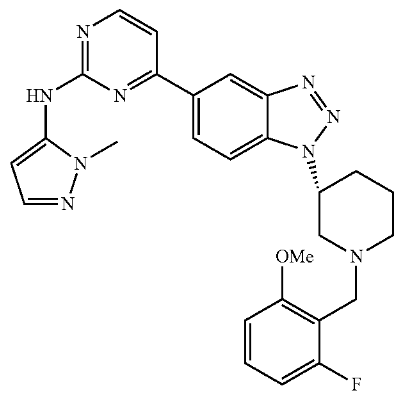 [SMILES: COc1cccc(F)c1CN1CCC[C@@H](n2nnc3cc(-c4ccnc(Nc5ccnn5C)n4)ccc32)C1] | (R)-4-(1-(1-(2-fluoro-6-methoxybenzyl)piperidin-3-yl)-1H-benzo[d][1,2,3]triazol-5-yl)-N-(1-methyl-1H-pyrazol-5-yl)pyrimidin-2-amine | 514.1 (1.057 min) |
| 106 | 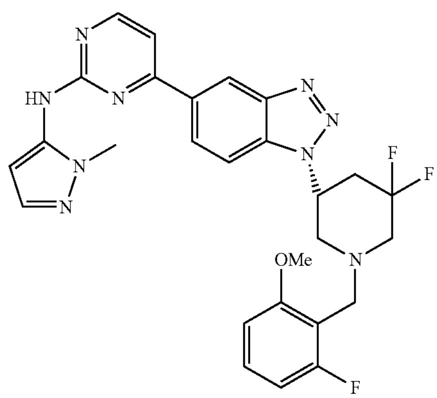 | (R)-4-(1-(5,5-difluoro-1-(2-fluoro-6-methoxybenzyl)piperidin-3-yl)-1H-benzo[d][1,2,3]triazol-5-yl)-N-(1-methyl-1H-pyrazol-5-yl)pyrimidin-2-amine | 550.2 (1.509 min) |
| 107 | 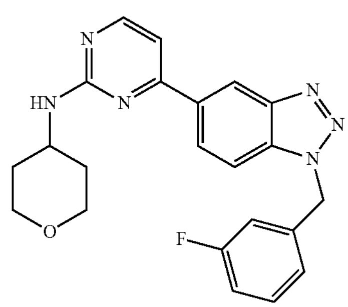 [SMILES: Fc1cccc(Cn2nnc3cc(-c4ccnc(NC5CCOCC5)n4)ccc32)c1] | 4-(1-(3-fluorobenzyl)-1H-benzo[d][1,2,3]triazol-5-yl)-N-(tetrahydro-2H-pyran-4-yl)pyrimidin-2-amine | 405.2 |

TABLE 2-continued

| Ex. # | Structure | Name | MS |
|---|---|---|---|
| 108 | 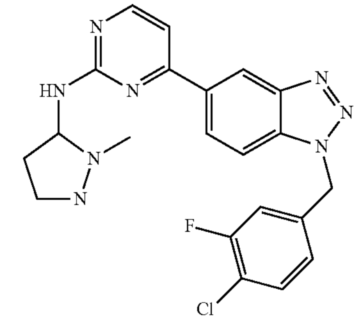 [SMILES: CN1NCCC1Nc1nccc(-c2ccc3c(c2)nnn3Cc2ccc(Cl)c(F)c2)n1] | 4-(1-(4-chloro-3-fluorobenzyl)-1H-benzo[d][1,2,3]triazol-5-yl)-N-(1-methyl-1H-pyrazol-5-yl)pyrimidin-2-amine | 435.2 |
| 109 | 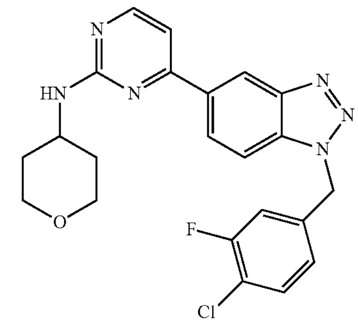 [SMILES: Fc1cc(Cn2nnc3cc(-c4ccnc(NC5CCOCC5)n4)ccc32)ccc1Cl] | 4-(1-(4-chloro-3-fluorobenzyl)-1H-benzo[d][1,2,3]triazol-5-yl)-N-(tetrahydro-2H-pyran-4-yl)pyrimidin-2-amine | 439.2 |
| 110 | 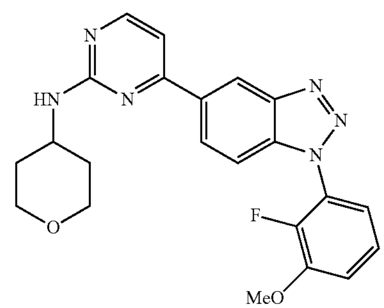 [SMILES: COc1cccc(-n2nnc3cc(-c4ccnc(NC5CCOCC5)n4)ccc32)c1F] | 4-(1-(3-fluoro-4-methoxybenzyl)-1H-benzo[d][1,2,3]triazol-5-yl)-N-(tetrahydro-2H-pyran-4-yl)pyrimidin-2-amine | 435.2 |
| 111 | 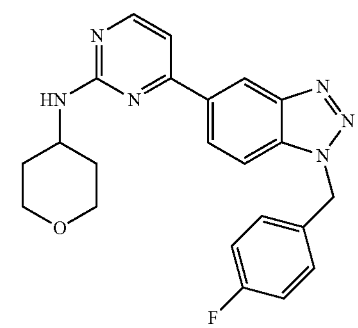 [SMILES: Fc1ccc(Cn2nnc3cc(-c4ccnc(NC5CCOCC5)n4)ccc32)cc1] | 4-(1-(4-fluorobenzyl)-1H-benzo[d][1,2,3]triazol-5-yl)-N-(tetrahydro-2H-pyran-4-yl)pyrimidin-2-amine | 405.2 |
| 112 | 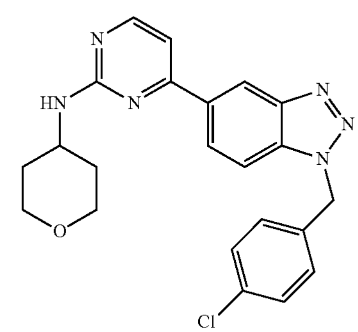 [SMILES: Clc1ccc(Cn2nnc3cc(-c4ccnc(NC5CCOCC5)n4)ccc32)cc1] | 4-(1-(4-chlorobenzyl)-1H-benzo[d][1,2,3]triazol-5-yl)-N-(tetrahydro-2H-pyran-4-yl)pyrimidin-2-amine | 421.2 |

TABLE 2-continued

| Ex. # | Structure | Name | MS |
|---|---|---|---|
| 113 | 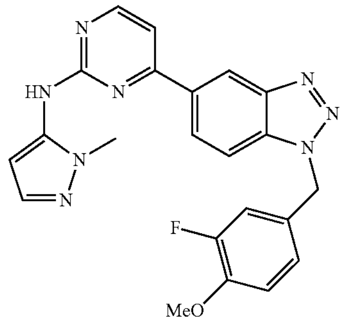 [SMILES: COc1ccc(Cn2nnc3cc(-c4ccnc(Nc5ccnn5C)n4)ccc32)cc1F] | 4-(1-(3-fluoro-4-methoxybenzyl)-1H-benzo[d][1,2,3]triazol-5-yl)-N-(1-methyl-1H-pyrazol-5-yl)pyrimidin-2-amine | 431.2 |
| 114 | 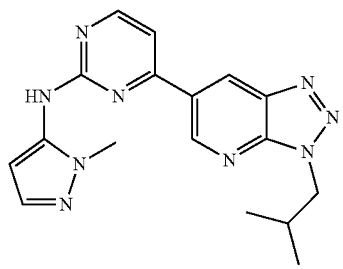 [SMILES: CC(C)Cn1nnc2cc(-c3ccnc(Nc4ccnn4C)n3)cnc21] | 4-(3-isobutyl-3H-[1,2,3]triazolo[4,5-b]pyridin-6-yl)-N-(1-methyl-1H-pyrazol-5-yl)pyrimidin-2-amine | 349.9 |
| 115 | 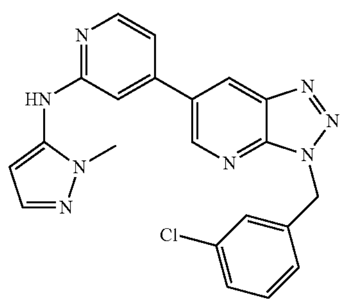 [SMILES: Cn1nccc1Nc1cc(-c2cnc3c(c2)nnn3Cc2cccc(Cl)c2)ccn1] | 4-(3-(3-chlorobenzyl)-3H-[1,2,3]triazolo[4,5-b]pyridin-6-yl)-N-(1-methyl-1H-pyrazol-5-yl)pyridin-2-amine | 416.9 |
| 116 | 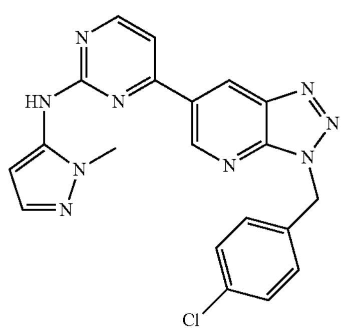 [SMILES: Cn1nccc1Nc1nccc(-c2cnc3c(c2)nnn3Cc2ccc(Cl)cc2)n1] | 4-(3-(4-chlorobenzyl)-3H-[1,2,3]triazolo[4,5-b]pyridin-6-yl)-N-(1-methyl-1H-pyrazol-5-yl)pyrimidin-2-amine | 417.8 |
| 117 | 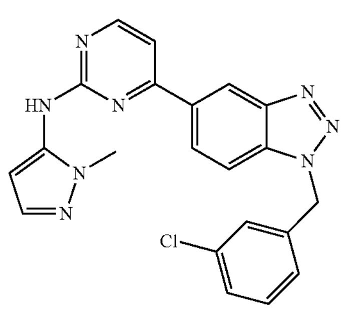 [SMILES: Cn1nccc1Nc1nccc(-c2ccc3c(c2)nnn3Cc2cccc(Cl)c2)n1] | 4-(1-(3-chlorobenzyl)-1H-benzo[d][1,2,3]triazol-5-yl)-N(1-methyl-1H-pyrazol-5-yl)pyrimidin-2-amine | 417.0 |

TABLE 2-continued

| Ex. # | Structure | Name | MS |
|---|---|---|---|
| 118 | 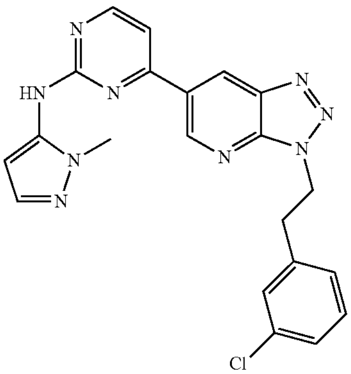 [SMILES: Cn1nccc1Nc1nccc(-c2cnc3c(c2)nnn3CCc2cccc(Cl)c2)n1] | 4-(3-(3-chlorophenethyl)-3H-[1,2,3]triazolo[4,5-b]pyridin-6-yl)-N-(1-methyl-1H-pyrazol-5-yl)pyrimidin-2-amine | 431.9 |
| 119 | 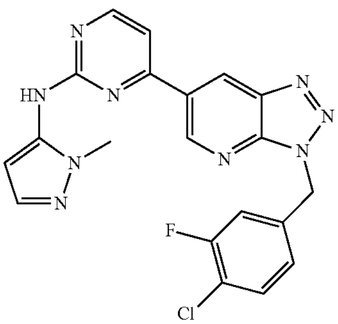 [SMILES: Cn1nccc1Nc1nccc(-c2cnc3c(c2)nnn3Cc2ccc(Cl)c(F)c2)n1] | 4-(3-(4-chloro-3-fluorobenzyl)-3H-(1,2,3]triazolo[4,5-b]pyridin-6-yl)-N-(1-methyl-1H-pyrazol-5-yl)pyrimidin-2-amine | 435.8 |
| 120 | 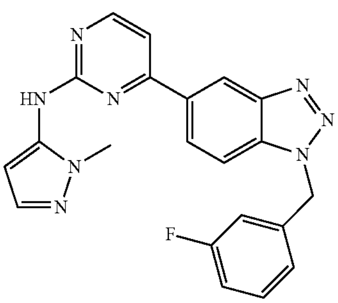 [SMILES: Cn1nccc1Nc1nccc(-c2ccc3c(c2)nnn3Cc2cccc(F)c2)n1] | 4-(1-(3-fluorobenzyl)-1H-benzo[d][1,2,3]triazol-5-yl)-N-(1-methyl-1H-pyrazol-5-yl)pyrimidin-2-amine | 400.9 |
| 121 | 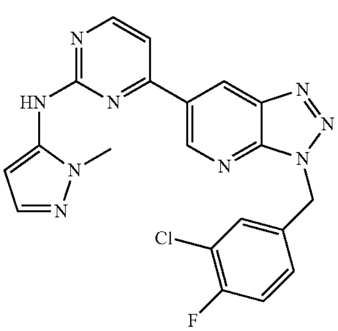 [SMILES: Cn1nccc1Nc1nccc(-c2cnc3c(c2)nnn3Cc2ccc(F)c(Cl)c2)n1] | 4-(3-(3-chloro-4-fluorobenzyl)-3H-[1,2,3]triazolo[4,5-b]pyridin-6-yl)-N-(1-methyl-1H-pyrazol-5-yl)pyrimidin-2-amine | 435.9 |

TABLE 2-continued

| Ex. # | Structure | Name | MS |
|---|---|---|---|
| 122 | 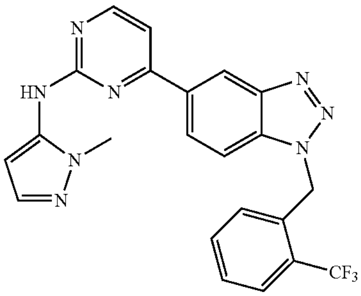 [SMILES: Cn1nccc1Nc1nccc(-c2ccc3c(c2)nnn3Cc2ccccc2C(F)(F)F)n1] | 1-methyl-1H-pyrazol-5-yl)-4-(1-(2-(trifluoromehyl)benzyl)-1H-benzo[d][1,2,3]triazol-5-yl)pyrimidin-2-amine | 450.9 |
| 123 | 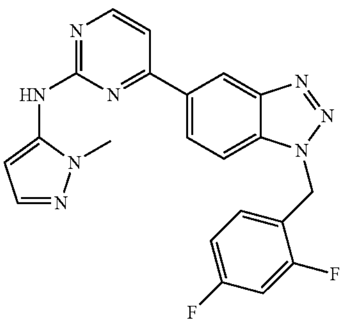 [SMILES: Cn1nccc1Nc1nccc(-c2ccc3c(c2)nnn3Cc2ccc(F)cc2F)n1] | 4-(1-(2,4-difluorobenzyl)-1H-benzo[d][1,2,3]triazol-5-yl)-N-(1-methyl-1H-pyrazol-5-yl)pyrimidin-2-amine | 418.9 |
| 124 | 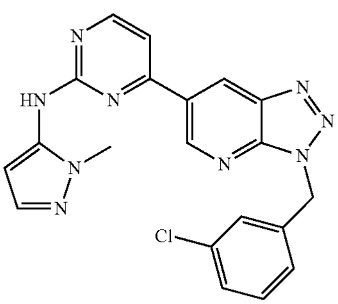 [SMILES: Cn1nccc1Nc1nccc(-c2cnc3c(c2)nnn3Cc2cccc(Cl)c2)n1] | 4-(3-(3-chlorobenzyl)-3H-[1,2,3]triazolo[4,5-b]pyridin-6-yl)-N-(1-methyl-1H-pyrazol-5-yl)pyrimidin-2-amine | 417.9 |
| 125 | 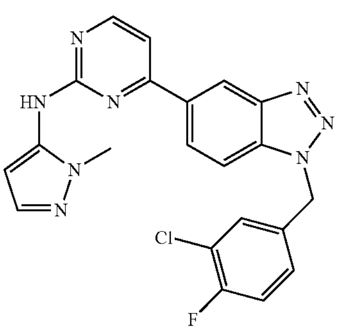 [SMILES: Cn1nccc1Nc1nccc(-c2ccc3c(c2)nnn3Cc2ccc(F)c(Cl)c2)n1] | 4-(1-(3-chloro-4-fluorobenzyl)-1H-benzo[d][1,2,3]triazol-5-yl)-N-(1-methyl-1H-pyrazol-5-yl)pyrimidin-2-amine | 434.9 |
| 126 | 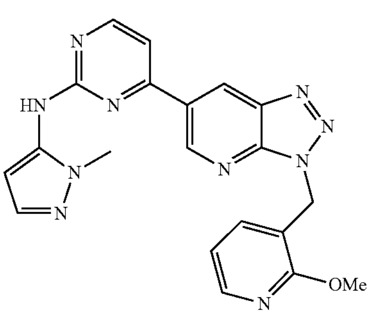 [SMILES: COc1ncccc1Cn1nnc2cc(-c3ccnc(Nc4ccnn4C)n3)cnc21] | 4-(3-((2-methoxypyridin-3-yl)methyl)-3H-[1,2,3]triazolo[4,5-b]pyridin-6-yl)-N-(1-methyl-1H-pyrazol-5-yl)pyrimidin-2-amine | 414.8 |

It will be understood that the enumerated embodiments are not intended to limit the invention to those embodiments. On the contrary, the invention is intended to cover all alternatives, modifications and equivalents, which may be included within the scope of the present invention as defined by the claims. Thus, the foregoing description is considered as illustrative only of the principles of the invention.

What is claimed is:

1. A compound of Formula I:

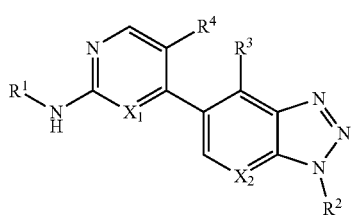

or a stereoisomer, tautomer or pharmaceutically acceptable salt thereof, wherein:

$X_1$ is N;

$X_2$ is selected from CH and N;

$R^1$ is selected from (a) $C_1$-$C_6$ alkyl optionally substituted with one or more groups independently selected from halogen, $OR^a$, $NR^bR^c$, oxo, CN, $C_3$-$C_6$ cycloalkyl and a 3 to 7 membered heterocycle; (b) $C_3$-$C_7$ cycloalkyl optionally substituted with one or more groups independently selected from halogen, $OR^a$, CN and $C_1$-$C_3$ alkyl optionally substituted with one or more groups independently selected from halogen and $OR^d$; (c) phenyl optionally substituted with one or more groups independently selected from halogen, $OR^a$, CN, $C_3$-$C_6$ cycloalkyl and $C_1$-$C_3$ alkyl optionally substituted with one or more groups independently selected from halogen and $OR^d$; (d) a 3 to 7 membered saturated or partially unsaturated heterocyclyl optionally substituted with one or more groups independently selected from halogen, $OR^a$, oxo, CN, $C_3$-$C_6$ cycloalkyl and $C_1$-$C_3$ alkyl optionally substituted with one or more groups independently selected from halogen and $OR^d$; (e) a 5 to 6 membered heteroaryl optionally substituted with one or more groups independently selected from halogen, $OR^e$, oxide, CN, $C_3$-$C_6$ cycloalkyl and $C_1$-$C_3$ alkyl optionally substituted with one or more groups independently selected from halogen, oxo and $OR^d$; and (f) a 7 to 10 membered bicyclic heterocycle optionally substituted with one or more groups independently selected from halogen, $OR^a$, oxo, CN, $C_3$-$C_6$ cycloalkyl and $C_1$-$C_3$ alkyl optionally substituted with one or more groups independently selected from halogen and $OR^d$;

$R^2$ is selected from (a) $C_1$-$C_{10}$ alkyl optionally substituted with one to four $R^f$ groups; (b) $C_3$-$C_6$ cycloalkyl optionally substituted with halogen, $C_1$-$C_3$ alkyl and $C_1$-$C_3$ alkoxy; (c) a 4 to 6 membered heterocyclyl containing one to three heteroatoms selected from N, O and S, wherein the heterocyclyl may be optionally substituted with one to four $R^g$ groups; (d) phenyl optionally substituted with one to four groups selected from halogen, $C_1$-$C_3$ alkyl and $C_1$-$C_3$ alkoxy; (e) a 5 to 6 membered heteroaryl containing one to four heteroatoms selected from N, O and S, wherein the heteroaryl may be optionally substituted with one to four groups selected from halogen, $C_1$-$C_3$ alkyl, $C_1$-$C_3$ alkoxy and a 5 to 6 membered heteroaryl containing one to four heteroatoms selected from N, O and S; (f) $C_8$-$C_{10}$ bicyclic cycloalkyl optionally substituted with halogen, $C_1$-$C_3$ alkyl and $C_1$-$C_3$ alkoxy; and (g) a 9 to 10 membered bicyclic heterocyclyl containing one to three heteroatoms selected from N, O and S, wherein the heterocyclyl may be optionally substituted with halogen, $C_1$-$C_3$ alkyl and $C_1$-$C_3$ alkoxy;

$R^3$ is selected from hydrogen and halogen;

$R^4$ is selected from hydrogen and halogen;

each $R^a$, $R^b$, $R^d$ and $R^e$ are independently selected from hydrogen and $C_1$-$C_6$ alkyl;

each $R^f$ is selected from (a) halogen; (b) hydroxy; (c) $C_1$-$C_3$ alkoxy; (d) $NR^kR^m$; (e) $C_3$-$C_6$ cycloalkyl optionally substituted with one or more $R^h$ groups; (f) a 4 to 6 membered heterocyclyl containing one to three heteroatoms selected from N, O and S, wherein the heterocyclyl may be optionally substituted with one or more groups selected from halogen, $C_1$-$C_3$ alkoxy, $C_1$-$C_3$ alkyl optionally substituted with halogen, —C(=O)O($C_1$-$C_6$ alkyl) and phenyl; (g) phenyl optionally substituted with one or more $R^j$ groups; and (h) a 5 to 6 membered heteroaryl containing one to four heteroatoms selected from N, O and S, wherein the heteroaryl may be optionally substituted with one or more $R^j$ groups;

each $R^g$ is selected from (a) halogen; (b) $C_1$-$C_3$ alkyl optionally substituted with halogen, $C_1$-$C_3$ alkoxy, or phenyl optionally substituted with two groups selected from halogen and $C_1$-$C_3$ alkoxy; (c) $C_1$-$C_3$ alkoxy optionally substituted with halogen; (d) phenyl optionally substituted with halogen or $C_1$-$C_3$ alkoxy; and (e) a 5 to 6 membered heteroaryl containing one to four heteroatoms selected from N, O and S, wherein the heteroaryl may be optionally substituted with one or two groups selected from halogen and $C_1$-$C_3$ alkoxy;

each $R^h$ is selected from halogen, $C_1$-$C_3$ alkyl, $C_1$-$C_3$ alkoxy and phenyl optionally substituted with $C_1$-$C_3$ alkoxy, wherein the alkyl, alkoxys and phenyl may be optionally substituted with halogen;

each $R^j$ is selected from halogen, $C_1$-$C_3$ alkyl and $C_1$-$C_3$ alkoxy, wherein the alkyl and alkoxy may be optionally substituted with halogen; and each $R^k$ and $R^m$ are independently selected from hydrogen and $C_1$-$C_3$ alkyl.

2. The compound of claim 1, wherein the compound has the structure of Formula VIII:

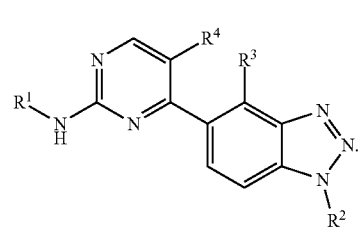

3. The compound of claim 1, wherein the compound has the structure of Formula IX:

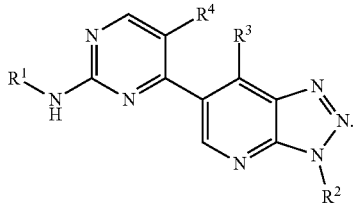

4. The compound of claim 1, wherein R³ and R⁴ are hydrogen.

5. The compound of claim 1, wherein R¹ is selected from methyl, ethyl, isopropyl, tert-butyl, isobutyl, 2-hydroxyethyl, 1-hydroxymethylpropyl, 1-hydroxypropan-2-yl, 2-methoxy-1-methyl-ethyl, 2-hydroxypropyl, 2-hydroxy-1-hydroxymethyl-ethyl, 1-hydroxy-2,2-dimethylpropan-3-yl, 2-hydroxy-2-methylpropan-1-yl, 1,2-dihydroxypropan-3-yl, acetyl, 2,2,2-trifluoro-1-methyl-ethyl, 2,2,2-trifluoro-1-hydroxymethyl-ethyl, 2-fluoro-1-methyl-ethyl, 2-fluoro-1-fluoromethyl-ethyl, 2,2,2-trifluoroethyl, 3,3,3-trifluoropropyl, cyclopropylmethyl, 2-morpholin-4-yl-ethyl, 2,2-difluoro-1-methyl-ethyl, oxetan-3-ylmethyl, 2-methyl-1-morpholinopropan-2-yl, 4-fluorophenyl, 3-chloro-4-fluorophenyl, 4-chloro-3-fluorophenyl, 2-o-tolyl, 4-fluoro-2-methylphenyl, 2-chlorophenyl, 2-chloro-4-fluorophenyl, 4-fluoro-2-trifluoromethylphenyl, 4-cyano-2-fluorophenyl, pyrimidin-5-yl, 4-methylpyrimidin-5-yl, 2-methylpyrimidin-4-yl, 6-methylpyrimidin-4-yl, 2-oxo-1,2,3,4-tetrahydroquinolin-6-yl, 3,5-dimethylisoxazol-4-yl, 2-methylpyridin-4-yl, 4-chloropyridin-2-yl, 2-methylpyridin-3-yl, 2-methylpyridin-4-yl, 2-ethoxypyridin-4-yl, 2-cyclopropylpyridin-4-yl, 1-methyl-1H-pyrazol-4-yl, 1-ethyl-1H-pyrazol-4-yl, 1-methyl-1H-pyrazol-3-yl, 2-ethyl-2H-pyrazol-3-yl, 1-benzyl-1H-pyrazol-4-yl, 2-methyl-2H-pyrazol-3-yl, 2-isopropyl-2H-pyrazol-3-yl, 1-methyl-1H-pyrazol-5-yl, 1,3-dimethyl-1H-pyrazol-4-yl, 1,3,5-trimethyl-1H-pyrazol-4-yl, 3-cyclopropyl-1-methyl-1H-pyrazol-5-yl, 1-methyl-6-oxo-1,6-dihydropyridin-3-yl, 4-methylthiazol-2-yl, 1-methyl-1H-[1,2,4]triazol-3-yl, 2-methyl-2H-1,2,3-triazol-4-yl, 1-methyl-1H-1,2,4-triazol-5-yl, 5-chloropyrazin-2-yl, 1-methyl-1H-tetrazol-5-yl, 2-methyl-2H-tetrazol-5-yl, 5-methyl-1,3,4-thiadiazol-2-yl, oxetan-3-yl, 3-methyloxyetan-3-yl, tetrahydropyran-4-yl, tetrahydro-2H-pyran-4-yl, tetrahydropyran-3-yl, 2-methyl-tetrahydropyran-4-yl, 2,2-dimethyl-tetrahydropyran-4-yl, 2-hydroxymethyltetrahydropyran-4-yl, 3-fluorotetrahydropyran-4-yl, 1-methylpiperidin-4-yl, 1-methyl-5-oxo-pyrrolidin-3-yl, tetrahydrofuran-3-yl, cyclopropyl, cyclopentyl, cyclobutyl, 3-hydroxycyclopentyl, 3,3-difluorocyclopentyl, 4-hydroxycyclohexyl, 3,3-difluorocyclobutyl, 3-hydroxycyclobutyl and 4,4-difluorocyclohexyl.

6. The compound of claim 1, wherein R¹ is selected from (S)-2-hydroxy-1-methyl-ethyl, (S)-1-hydroxymethyl-propyl, (1S,3S)-3-hydroxycyclopentyl, tetrahydropyran-4-yl, isopropyl, 1-methyl-1H-pyrazol-5-yl, 1-methyl-1H-pyrazol-4-yl, 2-methyl-2H-1,2,3-triazol-4-yl and 1-methyl-1H-1,2,4-triazol-5-yl.

7. The compound of claim 1, wherein R¹ is selected from 1-methyl-1H-pyrazol-5-yl, 1-methyl-1H-pyrazol-4-yl, tetrahydro-2H-pyran-4-yl, (S)-2-hydroxy-1-methyl-ethyl, (S)-1-hydroxymethyl-propyl and (1S,3S)-3-hydroxycyclopentyl.

8. The compound of claim 1, wherein R¹ is selected from 1-hydroxypropan-2-yl, isopropyl, 1-hydroxybutan-2-yl, 1-cyclopropylethyl, 1-hydroxy-3-methoxypropan-2-yl, 1,3-difluoropropan-2-yl, 1-cyclopropyl-2-hydroxyethyl, oxetan-3-ylmethyl, 4-methoxybutan-2-yl, 4,4,4-trifluoro-1-hydroxybutan-2-yl, 1-aminopropan-2-yl, 1-hydroxy-2,2-dimethylpropan-3-yl, 2-hydroxy-2-methylpropan-1-yl, 1,2-dihydroxypropan-3-yl, 3-hydroxycyclopentyl, 3,3-difluorocyclobutyl, 3-hydroxycyclobutyl, cyclopropylmethyl, 2-methyl-1-morpholinopropan-2-yl, 2-chloro-4-fluorophenyl, 4-fluoro-2-methylphenyl, tetrahydropyran-4-yl, 3-fluorotetrahydropyran-4-yl, tetrahydrodioxothiopyran-4-yl, 1,1-dioxotetrahydrothiophen-3-yl, oxetan-3-yl, 3-methyloxetan-3-yl, tetrahydrofuran-3-yl, 2,2-dimethyltetrahydropyran-4-yl, 2-methyltetrahydropyran-4-yl, pyrrolidin-3-yl, azetidin-3-yl, piperdin-3-yl, 2-(hydroxymethyl)tetrahydropyran-4-yl, 6-oxo-1,6-dihydropyridin-3-yl, 1-methylpyrazol-4-yl, 2-methylpyrimidin-4-yl, 6-methylpyrimidin-4-yl, 6-methoxypyrimidin-4-yl, 2-methylpyridin-4-yl, 1,3-dimethylpyrazol-4-yl, 2-methoxypyridin-4-yl, 1-methylpyrazol-3-yl, 6-methoxypyridin-3-yl, 2-ethylpyrimidin-4-yl, 6-methylpyridin-2-yl, 2-cyclopropylpyrimidin-4-yl, 5-fluoro-6-methylpyridin-2-yl, 5-cyclopropyl-1-methyl-pyrazol-4-yl, 5-bromo-2-methylpyridin-4-yl, 1,5-dimethylpyrazol-4-yl, 1,3-dimethylpyrazol-5-yl, 4-(2-hydroxypropan-2-yl)pyridin-2-yl, 1-ethyl-3-methypyrazol-4-yl, 5-ethoxy-2-methylpyridin-4-yl, 1-isopropylpyrazol-4-yl, 4-methylimidazol-5-yl, 1-methylimidazol-5-yl, 1-ethylpyrazol-4-yl, 2-(2-hydroxypropan-2-yl)pyridin-4-yl, 1-methyl-4-cyanopyrazol-5-yl, 3-methylpyridin-4-yl, 1-ethyl-3-methylpyrazol-5-yl, 1-methylpyrazol-5-yl, 1,4-dimethylpyrazol-5-yl, 1-ethylpyrazol-5-yl, 3-isopropyl-1-methylpyrazol-5-yl, 3-methylpyrazol-4-yl, 3-ethyl-1-methylpyrazol-4-yl, 1,3,5-trimethylpyrazol-4-yl, 3,5-dimethylpyrazol-4-yl, 2-cyclopropyl-5-methoxypyridin-4-yl, 5-ethyl-1-methylpyrazol-4-yl, 4-(2-methoxypyridine 1-oxide), 5-methoxy-2-methylpyridin-4-yl, 5-methyl-1,3,4-oxadizol-2-yl, 3-ethyl-1-methylpyrazol-5-yl, 1-(2-hydroxyethyl)-3-methylpyrazol-4-yl, 1-(2-hydroxyethyl)-5-methylpyrazol-4-yl, 1-methyl-3-(trifluoromethyl)pyrazol-4-yl, 1-methyl-3-(trifluoromethyl)pyrazol-5-yl, 1-methyl-1,2,3-triazol-5-yl, 2-methyl-1,2,3-triazol-4-yl, 1-methyl-1,2,4-triazol-5-yl, 2-methylpyridin-4-yl, 1-(2-hydroxyethyl)pyrazol-5-yl, methyl 4-picolinate, 4-picolinic acid, 1-cyclopropyl-5-methylpyrazol-4-yl, 1-cyclopropyl-3-methylpyrazol-4-yl, 2,3-dimethylpyridin-4-yl, 2,5-dimethylpyridin-4-yl, 1,3,4-oxadizol-2-yl, 3-methylpyridazin-4-yl, pyridazin-4-yl, tetrazol-5-yl, 1-methyltetrazol-5-yl, 3-cyclopropyl-1-methylpyrazol-5-yl, 2-methyltetrazol-5-yl, 5-methyl-1,3,4-thiadiazol-2-yl, 2-methyl-2,4,5,6-tetrahydrocyclopentapyrazol-3-yl, 3-oxo-2-oxabicyclo[2.2.1]heptan-5-yl and 2-oxabicyclo[2.2.1]heptan-5-yl.

9. The compound of claim 1, wherein R¹ is selected from the group consisting of 1-hydroxypropan-2-yl, isopropyl, 1-cyclopropylethyl, cyclopropylmethyl, 4-hydroxycyclohexyl, 1,1,1-trifluoropropan-2-yl, 3-fluoropropyl, tetrahydro-2H-pyran-4-yl, 3-fluorotetrahydropyran-4-yl, 2-(hydroxymethyl)tetrahydropyran-4-yl, (4-tetrahydro-2H-pyran-2-yl)methyl acetate, tetrahydrofuran-3-yl, 3-methyloxetan-3-yl, oxetany-3-ylmethyl, 2-methoxyethyl, 1-methyl-1H-pyrazol-5-yl, 1-methyl-1H-pyrazol-4-yl, 2-methylpyrazol-3-yl, 2,5-dimethylpyrazol-3-yl, 1,3-dimethylpyrazol-4-yl, 2-methyl-2H-1,2,3-triazol-4-yl and 1-methyl-1H-1,2,4-triazol-5-yl.

10. The compound of claim 1, wherein:
R¹ is selected from (a) C₁-C₅ alkyl optionally substituted with one or two groups selected from OH, cyclopropyl, oxetanyl and morpholino; (b) C₃-C₄ cycloalkyl; (c) a 4 to 6 membered heterocyclyl containing one O heteroatom optionally substituted with halogen or methyl; and (d) a 5 membered heteroaryl containing two to four heteroatoms selected from N and S substituted with one to three groups selected from methyl and cyclopropyl;

$R^2$ is selected from (a) $C_1$-$C_6$ alkyl optionally substituted with one or two $R^f$ groups; (b) $C_3$-$C_6$ cycloalkyl optionally substituted with one or two halogens; (c) a 4 to 6 membered heterocyclyl containing one to three heteroatoms selected from N, O and S, wherein the heterocyclyl may be optionally substituted with one to three $R^g$ groups; (d) a 5 to 6 membered heteroaryl containing one to four heteroatoms selected from N, O and S, wherein the heteroaryl may be optionally substituted with one or two groups selected from $C_1$-$C_3$ alkyl and a 5 to 6 membered heteroaryl containing one to four heteroatoms selected from N, O and S; and (e) $C_8$-$C_{10}$ bicyclic cycloalkyl optionally substituted with halogen;

$R^3$ and $R^4$ are hydrogen;

each $R^f$ is independently selected from (a) halogen; (b) hydroxy; (c) $C_1$-$C_3$ alkoxy; (d) $NR^kR^m$; (e) $C_3$-$C_6$ cycloalkyl optionally substituted with one or two $R^h$ groups; (f) a 4 to 6 membered heterocyclyl containing one to three heteroatoms selected from N, O and S, wherein the heterocyclyl may be optionally substituted with one group selected from $C_1$-$C_3$ alkyl optionally substituted with halogen, —C(=O)O($C_1$-$C_6$ alkyl) and phenyl; (g) phenyl optionally substituted with one or two $R^j$ groups; and (h) a 5 to 6 membered heteroaryl containing one to four heteroatoms selected from N, O and S, wherein the heteroaryl may be optionally substituted with one or two $R^j$ groups;

each $R^g$ is selected from (a) halogen; (b) $C_1$-$C_3$ alkyl optionally substituted with phenyl optionally substituted with two groups selected from halogen and $C_1$-$C_3$ alkoxy; (c) $C_1$-$C_3$ alkoxy; (d) phenyl optionally substituted with halogen; and (e) a 5 to 6 membered heteroaryl containing one N heteroatom optionally substituted with one or two groups selected from halogen and $C_1$-$C_3$ alkoxy;

each $R^h$ is selected from halogen, $C_1$-$C_3$ alkyl, $C_1$-$C_3$ alkoxy and phenyl optionally substituted with $C_1$-$C_3$ alkoxy optionally substituted with halogen;

each $R^j$ is selected from halogen, $C_1$-$C_3$ alkyl and $C_1$-$C_3$ alkoxy, wherein the alkyl and alkoxy may be optionally substituted with halogen; and each $R^k$ and $R^m$ are independently $C_1$-$C_3$ alkyl.

11. The compound of claim 1, wherein $R^1$ is selected from isopropyl, 1-hydroxy-2,2-dimethylpropan-3-yl, 2-hydroxy-2-methylpropan-1-yl, 1-hydroxypropan-2-yl, 1,2-dihydroxypropan-3-yl, cyclopropylmethyl, oxetan-3-ylmethyl, 2-methyl-1-morpholinopropan-2-yl, cyclopropyl, cyclobutyl, oxetan-3-yl, 3-methyloxetan-3-yl, tetrahydro-2H-pyran-4-yl, 3-fluorotetrahydro-2H-pyran-4-yl, (3S,4R)-3-fluorotetrahydro-2H-pyran-4-yl, (3S,4S)-3-fluorotetrahydro-2H-pyran-4-yl, 1-methyl-1H-pyrazol-4-yl, 1,3-dimethyl-1H-pyrazol-4-yl, 1,3,5-trimethyl-1H-pyrazol-4-yl, 1-methyl-1H-pyrazol-5-yl, 3-cyclopropyl-1-methyl-1H-pyrazol-5-yl, 2-methyl-2H-1,2,3-triazol-4-yl, 1-methyl-1H-tetrazol-5-yl, 2-methyl-2H-tetrazol-5-yl and 5-methyl-1,3,4-thiadiazol-2-yl.

12. The compound of claim 1, wherein $R^2$ is selected from 2-methylbutyl, 2-ethylbutyl, isobutyl, 2,2-difluoropropyl, 2,2-difluoroethyl, 3-fluoropropyl, 3-hydroxybutyl, 2-methoxyethyl, 3-methoxypropyl, 3-ethoxypropyl, 2-methoxy-2-methylpropyl, 3-methoxy-2,2-dimethylpropyl, 2-hydroxy-2-methylpropyl, 3-isopropoxypropyl, cyclopentylmethyl, (3,3-difluorocyclobutyl)methyl, (1-(ethoxymethyl)cyclopropyl)methyl, (1-(4-(trifluoromethoxy)phenyl)cyclopropyl)methyl, (1-methylcyclobutyl)methyl, (1-methylazetidin-3-yl)methyl, oxetan-3-ylmethyl, azetidin-3-ylmethyl, (1-(tert-butoxycarbonyl)azetidin-3-yl)methyl, (1-(2,2,2-trifluoroethyl)azetidin-3-yl)methyl, (4-phenylpiperidin-4-yl)methyl, (tetrahydro-2H-pyran-2-yl)methyl, 2,3-difluorobenzyl, 3-fluoro-4-methoxybenzyl, 4-(difluoromethoxy)benzyl, 4-chlorobenzyl, 4-methoxybenzyl, 3-fluorobenzyl, 4-chloro-3-fluorobenzyl, 4-fluorobenzyl, 3-chlorobenzyl, 3-chloro-4-fluorobenzyl, 2-(trifluoromethyl)benzyl, 2,4-difluorobenzyl, 4-chlorophenethyl, 2-chlorophenethyl, 3-chlorophenethyl, 1-(4-chloro-3-fluorophenyl)-2-(dimethylamino)ethyl, 1-(4-chloro-3-fluorophenyl)-2-(pyrrolidin-1-yl)ethyl, 2-hydroxy-1-(4-chloro-3-fluorophenyl)ethyl, (S)-2-hydroxy-1-(4-chloro-3-fluorophenyl)ethyl, (R)-2-hydroxy-1-(4-chloro-3-fluorophenyl)ethyl, 2-hydroxy-1-(3-fluoro-4-methoxyphenyl)ethyl, (S)-2-hydroxy-1-(3-fluoro-4-methoxyphenyl)ethyl, 2-(4-chloro-1H-pyrazol-1-yl)ethyl, (1-methyl-1H-pyrazol-3-yl)methyl, (1-methyl-1H-pyrazol-5-yl)methyl, (6-(trifluoromethyl)pyridin-2-yl)methyl, (2-methylpyridin-3-yl)methyl, (2-methoxypyridin-3-yl)methyl, (6-methylpyridin-3-yl)methyl, (6-methylpyridin-2-yl)methyl, (2-chloropyridin-3-yl)methyl, (3-methoxypyridin-2-yl)methyl, (3,5-difluoropyridin-2-yl)methyl, 2-(4-methyl-1H-pyrazol-1-yl)ethyl, 2-(1H-pyrazol-1-yl)ethyl, (3-fluoro-4-methoxyphenyl)(1-methyl-1H-pyrazol-4-yl)methyl, (3-fluoro-4-methoxyphenyl)(1-methyl-1H-1,2,3-triazol-5-yl)methyl, (3-fluoro-4-methoxyphenyl)(1-methyl-1H-imidazol-2-yl)methyl, 4,4-difluorocyclohexyl, piperidin-4-yl, 1-methylazetidin-3-yl, 1-(2-fluoro-6-methoxybenzyl)azetidin-3-yl, 4-(3-fluorophenyl)piperidin-3-yl, 4-(4-fluorophenyl)piperidin-3-yl, 4-(2,4-difluorophenyl)-1-methylpyrrolidin-3-yl, (3S,4R)-4-(2,4-difluorophenyl)-1-methylpyrrolidin-3-yl, 4-(3,4-difluorophenyl)-1-methylpyrrolidin-3-yl, (3S,4R)-4-(3,4-difluorophenyl)-1-methylpyrrolidin-3-yl, 4-(3,5-difluorophenyl)-1-methylpyrrolidin-3-yl, (3S,4R)-4-(3,5-difluorophenyl)-1-methylpyrrolidin-3-yl, 4-(3,4-difluorophenyl)-1-ethylpyrrolidin-3-yl, (3S,4R)-4-(3,4-difluorophenyl)-1-ethylpyrrolidin-3-yl, 4-(3,4-difluorophenyl)pyrrolidin-3-yl, (3S,4R)-4-(3,4-difluorophenyl)pyrrolidin-3-yl, 5,5-difluoropiperidin-3-yl, 4-(3,5-difluorophenyl)-1-isopropylpyrrolidin-3-yl, (3S,4R)-4-(3,5-difluorophenyl)-1-isopropylpyrrolidin-3-yl, 1-(5-fluoro-2-methoxypyridin-3-yl)pyrrolidin-3-yl, 4-(4-fluorophenyl)-1-(2-methoxyethyl)pyrrolidin-3-yl, (3R,4S)-4-(4-fluorophenyl)-1-(2-methoxyethyl)pyrrolidin-3-yl, (3S,4R)-4-(4-fluorophenyl)-1-(2-methoxyethyl)pyrrolidin-3-yl, 1-(2-fluoro-6-methoxybenzyl)piperidin-3-yl, (R)-1-(2-fluoro-6-methoxybenzyl)piperidin-3-yl, 1-(5,5-difluoro-1-(2-fluoro-6-methoxybenzyl)piperidin-3-yl, (R)-1-(5,5-difluoro-1-(2-fluoro-6-methoxybenzyl)piperidin-3-yl, 3-methyl-1-(pyridin-2-yl)-1H-pyrazol-5-yl and 5-chloro-2,3-dihydro-1H-inden-1-yl.

13. The compound of claim 1, wherein $R^2$ is $C_1$-$C_6$ alkyl optionally substituted with one or two $R^f$ groups.

14. The compound of claim 1, wherein the compound has the structure of Formula X:

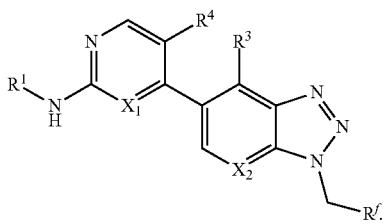

15. The compound of claim 1, wherein $R^2$ is $C_1$-$C_6$ alkyl.
16. The compound of claim 1, wherein the compound is:

4-(1-(2,3-difluorobenzyl)-1H-benzo[d][1,2,3]triazol-5-yl)-N-(1-methyl-1H-pyrazol-5-yl)pyrimidin-2-amine;
4-(1-(3-fluoro-4-methoxybenzyl)-1H-benzo[d][1,2,3]triazol-5-yl)-N-(1-methyl-1H-pyrazol-4-yl)pyrimidin-2-amine;
4-(1-(4-chlorophenethyl)-1H-benzo[d][1,2,3]triazol-5-yl)-N-(1-methyl-1H-pyrazol-5-yl)pyrimidin-2-amine;
4-(1-(2-(4-chloro-1H-pyrazol-1-yl)ethyl)-1H-benzo[d][1,2,3]triazol-5-yl)-N-(1-methyl-1H-pyrazol-5-yl)pyrimidin-2-amine;
4-(3-(3-fluoro-4-methoxybenzyl)-3H-[1,2,3]triazolo[4,5-b]pyridin-6-yl)-N-(1-methyl-1H-pyrazol-5-yl)pyrimidin-2-amine;
4-(1-(3-fluoro-4-methoxybenzyl)-1H-benzo[d][1,2,3]triazol-5-yl)-N-((3 S,4R)-3-fluorotetrahydro-2H-pyran-4-yl)pyrimidin-2-amine;
4-(1-(3-fluoro-4-methoxybenzyl)-1H-benzo[d][1,2,3]triazol-5-yl)-N-((3 S,4S)-3-fluorotetrahydro-2H-pyran-4-yl)pyrimidin-2-amine;
N-(1,3-dimethyl-1H-pyrazol-4-yl)-4-(1-(3-fluoro-4-methoxybenzyl)-1H-benzo[d][1,2,3]triazol-5-yl)pyrimidin-2-amine;
4-(1-(3-fluoro-4-methoxybenzyl)-1H-benzo[d][1,2,3]triazol-5-yl)-N-(2-methyl-2H-1,2,3-triazol-4-yl)pyrimidin-2-amine;
4-(1-(3-fluoro-4-methoxybenzyl)-1H-benzo[d][1,2,3]triazol-5-yl)-N-(oxetan-3-yl)pyrimidin-2-amine;
N-(4-(1-(3-fluoro-4-methoxybenzyl)-1H-benzo[d][1,2,3]triazol-5-yl)pyrimidin-2-yl)-5-methyl-1,3,4-thiadiazol-2-amine;
N-cyclobutyl-4-(1-(3-fluoro-4-methoxybenzyl)-1H-benzo[d][1,2,3]triazol-5-yl)pyrimidin-2-amine;
4-(1-(3-fluoro-4-methoxybenzyl)-1H-benzo[d][1,2,3]triazol-5-yl)-N-isopropylpyrimidin-2-amine;
N-(cyclopropylmethyl)-4-(1-(3-fluoro-4-methoxybenzyl)-1H-benzo[d][1,2,3]triazol-5-yl)pyrimidin-2-amine;
N-cyclopropyl-4-(1-(3-fluoro-4-methoxybenzyl)-1H-benzo[d][1,2,3]triazol-5-yl)pyrimidin-2-amine;
3-((4-(1-(3-fluoro-4-methoxybenzyl)-1H-benzo[d][1,2,3]triazol-5-yl)pyrimidin-2-yl)amino)-2,2-dimethylpropan-1-ol;
4-(1-(3-fluoro-4-methoxybenzyl)-1H-benzo[d][1,2,3]triazol-5-yl)-N-(oxetan-3-ylmethyl)pyrimidin-2-amine;
1-((4-(1-(3-fluoro-4-methoxybenzyl)-1H-benzo[d][1,2,3]triazol-5-yl)pyrimidin-2-yl)amino)-2-methylpropan-2-ol;
(S)-2-((4-(1-(3-fluoro-4-methoxybenzyl)-1H-benzo[d][1,2,3]triazol-5-yl)pyrimidin-2-yl)amino)propan-1-ol;
(R)-3-((4-(1-(3-fluoro-4-methoxybenzyl)-1H-benzo[d][1,2,3]triazol-5-yl)pyrimidin-2-yl)amino)propane-1,2-diol;
4-(1-(3-fluoro-4-methoxybenzyl)-1H-benzo[d][1,2,3]triazol-5-yl)-N-(3-methyloxetan-3-yl)pyrimidin-2-amine;
4-(1-(3-fluoro-4-methoxybenzyl)-1H-benzo[d][1,2,3]triazol-5-yl)-N-(1,3,5-trimethyl-1H-pyrazol-4-yl)pyrimidin-2-amine;
4-(1-(3-fluoro-4-methoxybenzyl)-1H-benzo[d][1,2,3]triazol-5-yl)-N-(2-methyl-1-morpholinopropan-2-yl)pyrimidin-2-amine;
4-(1-(3-fluoro-4-methoxybenzyl)-1H-benzo[d][1,2,3]triazol-5-yl)-N-(1-methyl-1H-tetrazol-5-yl)pyrimidin-2-amine;
N-(3-cyclopropyl-1-methyl-1H-pyrazol-5-yl)-4-(1-(3-fluoro-4-methoxybenzyl)-1H-benzo[d][1,2,3]triazol-5-yl)pyrimidin-2-amine;
4-(1-(3-fluoro-4-methoxybenzyl)-1H-benzo[d][1,2,3]triazol-5-yl)-N-(2-methyl-2H-tetrazol-5-yl)pyrimidin-2-amine;
N-(1-methyl-1H-pyrazol-5-yl)-4-(1-(2-methylbutyl)-1H-benzo[d][1,2,3]triazol-5-yl)pyrimidin-2-amine;
4-(1-(2-ethylbutyl)-1H-benzo[d][1,2,3]triazol-5-yl)-N-(1-methyl-1H-pyrazol-5-yl)pyrimidin-2-amine;
4-(1-(cyclopentylmethyl)-1H-benzo[d][1,2,3]triazol-5-yl)-N-(1-methyl-1H-pyrazol-5-yl)pyrimidin-2-amine;
4-(1-(2-methoxypropyl)-1H-benzo[d][1,2,3]triazol-5-yl)-N-(1-methyl-1H-pyrazol-5-yl)pyrimidin-2-amine;
4-(1-(2,2-difluoropropyl)-1H-benzo[d][1,2,3]triazol-5-yl)-N-(1-methyl-1H-pyrazol-5-yl)pyrimidin-2-amine;
4-(1-((1-methyl-1H-pyrazol-3-yl)methyl)-1H-benzo[d][1,2,3]triazol-5-yl)-N-(1-methyl-1H-pyrazol-5-yl)pyrimidin-2-amine;
4-(1-((4,4-difluorocyclohexyl)methyl)-1H-benzo[d][1,2,3]triazol-5-yl)-N-(1-methyl-1H-pyrazol-5-yl)pyrimidin-2-amine;
4-(1-((3,3-difluorocyclobutyl)methyl)-1H-benzo[1,2,3]triazol-5-yl)-N-(1-methyl-1H-pyrazol-5-yl)pyrimidin-2-amine;
4-(1-(4,4-difluorocyclohexyl)-1H-benzo[d][1,2,3]triazol-5-yl)-N-(1-methyl-1H-pyrazol-5-yl)pyrimidin-2-amine;
N-(1-methyl-1H-pyrazol-5-yl)-4-(1-((1-methylazetidin-3-yl)methyl)-1H-benzo[d][1,2,3]triazol-5-yl)pyrimidin-2-amine;
4-(1-(2,2-difluoroethyl)-1H-benzo[d][1,2,3]triazol-5-yl)-N-(1-methyl-1H-pyrazol-5-yl)pyrimidin-2-amine;
4-(1-isobutyl-1H-benzo[d][1,2,3]triazol-5-yl)-N-(1-methyl-1H-pyrazol-5-yl)pyrimidin-2-amine;
N-(1-methyl-1H-pyrazol-5-yl)-4-(1-((1-methyl-1H-pyrazol-5-yl)methyl)-1H-benzo[d][1,2,3]triazol-5-yl)pyrimidin-2-amine;
4-(1-(3-fluoropropyl)-1H-benzo[d][1,2,3]triazol-5-yl)-N-(1-methyl-1H-pyrazol-5-yl)pyrimidin-2-amine;
4-(5-(2-((1-methyl-1H-pyrazol-5-yl)amino)pyrimidin-4-yl)-1H-benzo[d][1,2,3]triazol-1-yl)butan-2-ol;
4-(1-(3-methoxypropyl)-1H-benzo[d][1,2,3]triazol-5-yl)-N-(1-methyl-1H-pyrazol-5-yl)pyrimidin-2-amine;
4-(1-(3-ethoxypropyl)-1H-benzo[d][1,2,3]triazol-5-yl)-N-(1-methyl-1H-pyrazol-5-yl)pyrimidin-2-amine;
4-(1-(2-methoxy-2-methylpropyl)-1H-benzo[d][1,2,3]triazol-5-yl)-N-(1-methyl-1H-pyrazol-5-yl)pyrimidin-2-amine;
4-(1-((1-(ethoxymethyl)cyclopropyl)methyl)-1H-benzo[d][1,2,3]triazol-5-yl)-N-(1-methyl-1H-pyrazol-5-yl)pyrimidin-2-amine;
4-(1-(3-methoxy-2,2-dimethylpropyl)-1H-benzo[d][1,2,3]triazol-5-yl)-N-(1-methyl-1H-pyrazol-5-yl)pyrimidin-2-amine;

N-(1-methyl-1H-pyrazol-5-yl)-4-(1-((1-(4-(trifluoromethoxy)phenyl)cyclopropyl)methyl)-1H-benzo[d][1,2,3]triazol-5-yl)pyrimidin-2-amine;

N-(1-methyl-1H-pyrazol-5-yl)-4-(1-((1-methylcyclobutyl)methyl)-1H-benzo[d][1,2,3]triazol-5-yl)pyrimidin-2-amine;

4-(1-(2-chlorophenethyl)-1H-benzo[d][1,2,3]triazol-5-yl)-N-(1-methyl-1H-pyrazol-5-yl)pyrimidin-2-amine;

4-(1-(3-chlorophenethyl)-1H-benzo[d][1,2,3]triazol-5-yl)-N-(1-methyl-1H-pyrazol-5-yl)pyrimidin-2-amine;

4-(1-(4-(difluoromethoxy)benzyl)-1H-benzo[d][1,2,3]triazol-5-yl)-N-(1-methyl-1H-pyrazol-5-yl)pyrimidin-2-amine;

N-(1-methyl-1H-pyrazol-5-yl)-4-(1-((6-(trifluoromethyl)pyridin-2-yl)methyl)-1H-benzo[d][1,2,3]triazol-5-yl)pyrimidin-2-amine;

N-(1-methyl-1H-pyrazol-5-yl)-4-(1-((2-methylpyridin-3-yl)methyl)-1H-benzo[d][1,2,3]triazol-5-yl)pyrimidin-2-amine;

N-(1-methyl-1H-pyrazol-5-yl)-4-(1-((6-methylpyridin-2-yl)methyl)-1H-benzo[d][1,2,3]triazol-5-yl)pyrimidin-2-amine;

4-(1-(5-chloro-2,3-dihydro-1H-inden-1-yl)-1H-benzo[d][1,2,3]triazol-5-yl)-N-(1-methyl-1H-pyrazol-5-yl)pyrimidin-2-amine;

2-methyl-1-(5-(2-((1-methyl-1H-pyrazol-5-yl)amino)pyrimidin-4-yl)-1H-benzo[d][1,2,3]triazol-1-yl)propan-2-ol;

N-(1-methyl-1H-pyrazol-5-yl)-4-(1-(oxetan-3-ylmethyl)-1H-benzo[d][1,2,3]triazol-5-yl)pyrimidin-2-amine;

4-(1-(azetidin-3-ylmethyl)-1H-benzo[d][1,2,3]triazol-5-yl)-N-(1-methyl-1H-pyrazol-5-yl)pyrimidin-2-amine;

tert-butyl 3-((5-(2-((1-methyl-1H-pyrazol-5-yl)amino)pyrimidin-4-yl)-1H-benzo[d][1,2,3]triazol-1-yl)methyl)azetidine-1-carboxylate;

N-(1-methyl-1H-pyrazol-5-yl)-4-(1-((1-(2,2,2-trifluoroethyl)azetidin-3-yl)methyl)-1H-benzo[d][1,2,3]triazol-5-yl)pyrimidin-2-amine;

4-(1-(4-methoxybenzyl)-1H-benzo[d][1,2,3]triazol-5-yl)-N-(1-methyl-1H-pyrazol-5-yl)pyrimidin-2-amine;

4-(1-((2-chloropyridin-3-yl)methyl)-1H-benzo[d][1,2,3]triazol-5-yl)-N-(1-methyl-1H-pyrazol-5-yl)pyrimidin-2-amine;

4-(1-((2-methoxypyridin-3-yl)methyl)-1H-benzo[d][1,2,3]triazol-5-yl)-N-(1-methyl-1H-pyrazol-5-yl)pyrimidin-2-amine;

4-(1-((3-methoxypyridin-2-yl)methyl)-1H-benzo[d][1,2,3]triazol-5-yl)-N-(1-methyl-1H-pyrazol-5-yl)pyrimidin-2-amine;

4-(1-((3,5-difluoropyridin-2-yl)methyl)-1H-benzo[d][1,2,3]triazol-5-yl)-N-(1-methyl-1H-pyrazol-5-yl)pyrimidin-2-amine;

(S)-4-(1-((3-fluoro-4-methoxyphenyl)(1-methyl-1H-pyrazol-4-yl)methyl)-1H-benzo[d][1,2,3]triazol-5-yl)-N-(1-methyl-1H-pyrazol-5-yl)pyrimidin-2-amine;

(S)-4-(1-((3-fluoro-4-methoxyphenyl)(1-methyl-1H-1,2,3-triazol-5-yl)methyl)-1H-benzo[d][1,2,3]triazol-5-yl)-N-(1-methyl-1H-pyrazol-5-yl)pyrimidin-2-amine;

(S)-4-(1-((3-fluoro-4-methoxyphenyl)(1-methyl-1H-imidazol-2-yl)methyl)-1H-benzo[d][1,2,3]triazol-5-yl)-N-(1-methyl-1H-pyrazol-5-yl)pyrimidin-2-amine;

4-(1-((3S,4R)-4-(2,4-difluorophenyl)-1-methylpyrrolidin-3-yl)-1H-benzo[d][1,2,3]triazol-5-yl)-N-(1-methyl-1H-pyrazol-5-yl)pyrimidin-2-amine;

4-(1-((3S,4R)-4-(2,4-difluorophenyl)-1-methylpyrrolidin-3-yl)-1H-benzo[d][1,2,3]triazol-5-yl)-N-(1-methyl-1H-pyrazol-5-yl)pyrimidin-2-amine;

4-(1-((3S,4R)-4-(3,4-difluorophenyl)-1-methylpyrrolidin-3-yl)-1H-benzo[d][1,2,3]triazol-5-yl)-N-(1-methyl-1H-pyrazol-5-yl)pyrimidin-2-amine;

4-(1-((3S,4R)-4-(3,5-difluorophenyl)-1-methylpyrrolidin-3-yl)-1H-benzo[d][1,2,3]triazol-5-yl)-N-(1-methyl-1H-pyrazol-5-yl)pyrimidin-2-amine;

4-(1-((3S,4R)-4-(3,4-difluorophenyl)-1-ethylpyrrolidin-3-yl)-1H-benzo[d][1,2,3]triazol-5-yl)-N-(1-methyl-1H-pyrazol-5-yl)pyrimidin-2-amine;

4-(1-((3S,4R)-4-(3,4-difluorophenyl)pyrrolidin-3-yl)-1H-benzo[d][1,2,3]triazol-5-yl)-N-(1-methyl-1H-pyrazol-5-yl)pyrimidin-2-amine;

(R)-4-(1-(5,5-difluoropiperidin-3-yl)-1H-benzo[d][1,2,3]triazol-5-yl)-N-(1-methyl-1H-pyrazol-5-yl)pyrimidin-2-amine;

4-(1-((3S,4R)-4-(3,5-difluorophenyl)-1-isopropylpyrrolidin-3-yl)-1H-benzo[d][1,2,3]triazol-5-yl)-N-(1-methyl-1H-pyrazol-5-yl)pyrimidin-2-amine;

(S)-4-(1-(1-(5-fluoro-2-methoxypyridin-3-yl)pyrrolidin-3-yl)-1H-benzo[d][1,2,3]triazol-5-yl)-N-(1-methyl-1H-pyrazol-5-yl)pyrimidin-2-amine;

4-(1-(3-methyl-1-(pyridin-2-yl)-1H-pyrazol-5-yl)-1H-benzo[d][1,2,3]triazol-5-yl)-N-(1-methyl-1H-pyrazol-5-yl)pyrimidin-2-amine;

4-(1-((3R,4S)-4-(4-fluorophenyl)-1-(2-methoxyethyl)pyrrolidin-3-yl)-1H-benzo[d][1,2,3]triazol-5-yl)-N-(1-methyl-1H-pyrazol-5-yl)pyrimidin-2-amine;

N-(1-methyl-1H-pyrazol-5-yl)-4-(1-((4-phenylpiperidin-4-yl)methyl)-1H-benzo[d][1,2,3]triazol-5-yl)pyrimidin-2-amine;

N-(1-methyl-1H-pyrazol-5-yl)-4-(1-(piperidin-4-yl)-1H-benzo[d][1,2,3]triazol-5-yl)pyrimidin-2-amine;

N-(1-methyl-1H-pyrazol-5-yl)-4-(1-(1-methylazetidin-3-yl)-1H-benzo[d][1,2,3]triazol-5-yl)pyrimidin-2-amine;

4-(1-((3S,4R)-4-(4-fluorophenyl)-1-(2-methoxyethyl)pyrrolidin-3-yl)-1H-benzo[d][1,2,3]triazol-5-yl)-N-(1-methyl-1H-pyrazol-5-yl)pyrimidin-2-amine;

4-(1-(1-(2-fluoro-6-methoxybenzyl)azetidin-3-yl)-1H-benzo[d][1,2,3]triazol-5-yl)-N-(1-methyl-1H-pyrazol-5-yl)pyrimidin-2-amine;

4-(1-(4-(3-fluorophenyl)piperidin-3-yl)-1H-benzo[d][1,2,3]triazol-5-yl)-N-(1-methyl-1H-pyrazol-5-yl)pyrimidin-2-amine;

4-(1-(4-(4-fluorophenyl)piperidin-3-yl)-1H-benzo[d][1,2,3]triazol-5-yl)-N-(1-methyl-1H-pyrazol-5-yl)pyrimidin-2-amine;

4-(1-(1-(4-chloro-3-fluorophenyl)-2-(dimethylamino)ethyl)-1H-benzo[d][1,2,3]triazol-5-yl)-N-(1-methyl-1H-pyrazol-5-yl)pyrimidin-2-amine;

4-(1-(1-(4-chloro-3-fluorophenyl)-2-(pyrrolidin-1-yl)ethyl)-1H-benzo[d][1,2,3]triazol-5-yl)-N-(1-methyl-1H-pyrazol-5-yl)pyrimidin-2-amine;

(S)-2-(4-chloro-3-fluorophenyl)-2-(5-(2-((1-methyl-1H-pyrazol-5-yl)amino)pyrimidin-4-yl)-1H-benzo[d][1,2,3]triazol-1-yl)ethanol;

(R)-2-(4-chloro-3-fluorophenyl)-2-(5-(2-((1-methyl-1H-pyrazol-5-yl)amino)pyrimidin-4-yl)-1H-benzo[d][1,2,3]triazol-1-yl)ethanol;

(S)-2-(3-fluoro-4-methoxyphenyl)-2-(5-(2-((1-methyl-1H-pyrazol-5-yl)amino)pyrimidin-4-yl)-1H-benzo[d][1,2,3]triazol-1-yl)ethanol;

N-(1-methyl-1H-pyrazol-4-yl)-4-(1-(2-methylbutyl)-1H-benzo[d][1,2,3]triazol-5-yl)pyrimidin-2-amine;

4-(1-isobutyl-1H-benzo[d][1,2,3]triazol-5-yl)-N-(1-methyl-H-pyrazol-4-yl)pyrimidin-2-amine;

(2S)-2-((4-(1-(2-methylbutyl)-1H-benzo[d][1,2,3]triazol-5-yl)pyrimidin-2-yl)amino)propan-1-ol;

4-(1-isobutyl-H-benzo[d][1,2,3]triazol-5-yl)-N-(2-methyl-2H-1,2,3-triazol-4-yl)pyrimidin-2-amine;

N-(2-methyl-2H-1,2,3-triazol-4-yl)-4-(1-(2-methylbutyl)-1H-benzo[d][1,2,3]triazol-5-yl)pyrimidin-2-amine;

N-(1-methyl-1H-pyrazol-5-yl)-4-(1-((tetrahydro-2H-pyran-2-yl)methyl)-1H-benzo[d][1,2,3]triazol-5-yl)pyrimidin-2-amine;

4-(1-(3-isopropoxypropyl)-1H-benzo[d][1,2,3]triazol-5-yl)-N-(1-methyl-1H-pyrazol-5-yl)pyrimidin-2-amine;

4-(1-(2-(4-methyl-1H-pyrazol-1-yl)ethyl)-1H-benzo[d][1,2,3]triazol-5-yl)-N-(1-methyl-1H-pyrazol-5-yl)pyrimidin-2-amine;

4-(1-(2-(1H-pyrazol-1-yl)ethyl)-1H-benzo[d][1,2,3]triazol-5-yl)-N-(1-methyl-1H-pyrazol-5-yl)pyrimidin-2-amine;

(R)-4-(1-(1-(2-fluoro-6-methoxybenzyl)piperidin-3-yl)-1H-benzo[d][1,2,3]triazol-5-yl)-N-(1-methyl-1H-pyrazol-5-yl)pyrimidin-2-amine;

(R)-4-(1-(5,5-difluoro-1-(2-fluoro-6-methoxybenzyl)piperidin-3-yl)-1H-benzo[d][1,2,3]triazol-5-yl)-N-(1-methyl-1H-pyrazol-5-yl)pyrimidin-2-amine;

4-(1-(3-fluorobenzyl)-1H-benzo[d][1,2,3]triazol-5-yl)-N-(tetrahydro-2H-pyran-4-yl)pyrimidin-2-amine;

4-(1-(4-chloro-3-fluorobenzyl)-1H-benzo[d][1,2,3]triazol-5-yl)-N-(1-methyl-H-pyrazol-5-yl)pyrimidin-2-amine;

4-(1-(4-chloro-3-fluorobenzyl)-1H-benzo[d][1,2,3]triazol-5-yl)-N-(tetrahydro-2H-pyran-4-yl)pyrimidin-2-amine;

4-(1-(3-fluoro-4-methoxybenzyl)-1H-benzo[d][1,2,3]triazol-5-yl)-N-(tetrahydro-2H-pyran-4-yl)pyrimidin-2-amine;

4-(1-(4-fluorobenzyl)-1H-benzo[d][1,2,3]triazol-5-yl)-N-(tetrahydro-2H-pyran-4-yl)pyrimidin-2-amine;

4-(1-(4-chlorobenzyl)-1H-benzo[d][1,2,3]triazol-5-yl)-N-(tetrahydro-2H-pyran-4-yl)pyrimidin-2-amine;

4-(1-(3-fluoro-4-methoxybenzyl)-1H-benzo[d][1,2,3]triazol-5-yl)-N-(1-methyl-1H-pyrazol-5-yl)pyrimidin-2-amine;

4-(3-isobutyl-3H-[1,2,3]triazolo[4,5-b]pyridin-6-yl)-N-(1-methyl-1H-pyrazol-5-yl)pyrimidin-2-amine;

4-(3-(4-chlorobenzyl)-3H-[1,2,3]triazolo[4,5-b]pyridin-6-yl)-N-(1-methyl-1H-pyrazol-5-yl)pyrimidin-2-amine;

4-(1-(3-chlorobenzyl)-1H-benzo[d][1,2,3]triazol-5-yl)-N-(1-methyl-1H-pyrazol-5-yl)pyrimidin-2-amine;

4-(3-(3-chlorophenethyl)-3H-[1,2,3]triazolo[4, 5-b]pyridin-6-yl)-N-(1-methyl-1H-pyrazol-5-yl)pyrimidin-2-amine;

4-(3-(4-chloro-3-fluorobenzyl)-3H-[1,2,3]triazolo[4,5-b]pyridin-6-yl)-N-(1-methyl-1H-pyrazol-5-yl)pyrimidin-2-amine;

4-(1-(3-fluorobenzyl)-1H-benzo[d][1,2,3]triazol-5-yl)-N-(1-methyl-1H-pyrazol-5-yl)pyrimidin-2-amine;

4-(3-(3-chloro-4-fluorobenzyl)-3H-[1,2,3]triazolo[4,5-b]pyridin-6-yl)-N-(1-methyl-1H-pyrazol-5-yl)pyrimidin-2-amine;

N-(1-methyl-1H-pyrazol-5-yl)-4-(1-(2-(trifluoromethyl)benzyl)-1H-benzo[d][1,2,3]triazol-5-yl)pyrimidin-2-amine;

4-(1-(2,4-difluorobenzyl)-1H-benzo[d][1,2,3]triazol-5-yl)-N-(1-methyl-1H-pyrazol-5-yl)pyrimidin-2-amine;

4-(3-(3-chlorobenzyl)-3H-[1,2,3]triazolo[4, 5-b]pyridin-6-yl)-N-(1-methyl-1H-pyrazol-5-yl)pyrimidin-2-amine;

4-(1-(3-chloro-4-fluorobenzyl)-1H-benzo[d][1,2,3]triazol-5-yl)-N-(1-methyl-1H-pyrazol-5-yl)pyrimidin-2-amine; or 4-(3-((2-methoxypyridin-3-yl)methyl)-3H-[1,2,3]triazolo[4,5-b]pyridin-6-yl)-N-(1-methyl-1H-pyrazol-5-yl)pyrimidin-2-amine;

or a pharmaceutically acceptable salt thereof.

17. A pharmaceutical composition comprising a compound of claim 1 or a stereoisomer, tautomer or pharmaceutically acceptable salt thereof.

18. A pharmaceutical composition comprising a compound of claim 1 or a stereoisomer, tautomer or pharmaceutically acceptable salt thereof and at least one pharmaceutically acceptable excipient.

* * * * *

UNITED STATES PATENT AND TRADEMARK OFFICE
CERTIFICATE OF CORRECTION

PATENT NO. : 9,763,942 B2
APPLICATION NO. : 15/197479
DATED : September 19, 2017
INVENTOR(S) : James F. Blake et al.

Page 1 of 1

It is certified that error appears in the above-identified patent and that said Letters Patent is hereby corrected as shown below:

On the Title Page

Item (72), Line 9, Inventor, Brad Newhouse, please delete "Boulder, CA" and insert -- Boulder, CO --;

In the Claims

Column 98, Line 11, Claim 1, please delete "$R^b$," and insert -- $R^b$, $R^c$, --;

Column 99, Lines 45-46, Claim 5, please delete "3-methyloxyetan-3-yl" and insert -- 3-methyloxetan-3-yl --;

Column 104, Line 35, Claim 16, please delete "-1H-benzo [1,2,3]" and insert -- -1H-benzo [d] [1,2,3] --;

Column 106, Line 65, Claim 16, please delete "H" and insert -- 1H --;

Column 107, Line 1, Claim 16, please delete "H" and insert -- 1H --;

Column 107, Line 26, Claim 16, please delete "1-methyl-H" and insert -- 1-methyl-1H -- therefor.

Signed and Sealed this
Fifteenth Day of May, 2018

Andrei Iancu
*Director of the United States Patent and Trademark Office*